US007741077B2

(12) United States Patent
Grawunder et al.

(10) Patent No.: US 7,741,077 B2
(45) Date of Patent: Jun. 22, 2010

(54) METHOD FOR THE GENERATION OF GENETICALLY MODIFIED VERTEBRATE PRECURSOR LYMPHOCYTES AND USE THEREOF FOR THE PRODUCTION OF HETEROLOGOUS BINDING PROTEINS

(75) Inventors: Ulf Grawunder, Basel (CH); Georg Friedrich Melchers, Grenzach-Wyhlen (DE)

(73) Assignee: 4-Antibody AG, Basel (CH)

( * ) Notice: Subject to any disclaimer, the term of this patent is extended or adjusted under 35 U.S.C. 154(b) by 891 days.

(21) Appl. No.: 10/499,631

(22) PCT Filed: Dec. 22, 2001

(86) PCT No.: PCT/EP01/15303

§ 371 (c)(1),
(2), (4) Date: Sep. 12, 2005

(87) PCT Pub. No.: WO03/068819

PCT Pub. Date: Aug. 21, 2003

(65) Prior Publication Data

US 2006/0052585 A1 Mar. 9, 2006

(51) Int. Cl.

| | |
|---|---|
| ***C12N 15/13*** | (2006.01) |
| ***C12N 15/85*** | (2006.01) |
| ***C12N 15/87*** | (2006.01) |
| *C12N 15/00* | (2006.01) |

(52) U.S. Cl. ...................... 435/69.6; 435/455; 435/462; 435/463; 435/467

(58) Field of Classification Search ....................... None
See application file for complete search history.

(56) References Cited

U.S. PATENT DOCUMENTS

| | | | | |
|---|---|---|---|---|
| 5,169,939 | A * | 12/1992 | Gefter et al. | 530/387.3 |
| 5,583,033 | A | 12/1996 | Terstappen et al. | |
| 5,874,299 | A | 2/1999 | Lonberg | |
| 6,051,225 | A * | 4/2000 | Mezes et al. | 424/133.1 |
| 6,300,129 | B1 | 10/2001 | Lonberg et al. | |
| 2005/0196755 | A1 | 9/2005 | Zauderer et al. | |

FOREIGN PATENT DOCUMENTS

| | | | |
|---|---|---|---|
| EP | 0546073 | B1 | 9/1997 |
| EP | 0605522 | B1 | 6/1999 |
| EP | 0585287 | B1 | 10/1999 |
| JP | 05-184386 | | 7/1993 |
| JP | 10-146194 | | 6/1998 |
| NZ | 295418 | | 2/2000 |
| WO | WO 92/03918 | | 3/1992 |
| WO | WO 01/87058 | A1 | 11/2001 |

OTHER PUBLICATIONS

Green (Journal of Immunological Methods, 1999. 23:11-23).*
Zan et al (Immunity, May 2001, vol. 14, pp. 643-653).*
Roitt et al, Immunology (text book), 5th Edition, 1998, p. 106.*
Austin et al (Human Gene Therapy, Jul. 1, 2001, vol. 12, pp. 1239-1249).*
Kawaichi et al (Journal of Biological Chemistry, 1991, vol. 266, pp. 18387-1394).*
Abstract of Kim et al (FASEB, 2002, vol. 16, p. A315).*
International Search Report, completed Jun. 20, 2002.
Dong Sung An et al, "Lentivirus Vector-Mediated Hematopoietic Stem Cell Gene Transfer of Common Gamma-Chain Cytokine Receptor in Rhesus Macaques", Journal of Virology, Apr. 2001, pp. 3547-3555.
Anne-Catherine Fluckiger et al, "In Vitro Reconstitution of Human B-Cell Ontogeny: From CD 34+ Multipotent Progenitors to Ig-Secreting Cells". Blood, vol. 92, No. 12, Dec. 15. 1998, pp. 4509-4520.
Paola Ghia et al, "Ordering of Human Bone Marrow B Lymphocyte Precursors by Single-Cell Polymerase Chain Reaction Analyses of the Rearrangement Status of the Immunoglobulin H and L Chain Gene Loci", Journal Exp. Med., vol. 184, Dec. 1996, pp. 2217-2229.
M. Duenas et al, "In vitro immunization of naive human B cells yields high affinity immunoglobulin G antibodies as illustrated by phage display", 1996, Blackwell Science Ltd., Immunology 89, pp. 1-7.
Frederick W. Alt et al, "Ordered rearrangement of immunoglobulin heavy chain variable region segments", The EMBO Journal, 1984, vol. 3, No. 6, pp. 1209-1219.
Jianzhu Chen et al, "Immunoglobulin gene rearrangement in B cell deficient mice generated by targeted deletion of the JH locus", International Immunology, 1993, vol. 5, No. 6, pp. 647-656.
Jianzhu Chen et al, "B cell development in mice that lack one or both immunoglobulin light chain genes", The EMBO Journal, 1993, vol. 12, No. 3, pp. 821-830.
Mike Clark, "Antibody humanization: a case of the 'Emperor's new clothes'?", Immunology Today, Aug. 2000, vol. 21, No. 8, pp. 397-402.
Simona Fiorentini et al, "Humanization of an antibody recognizing a breast cancer specific epitope by CDR-grafting", Immunotechnology 3 (1997) pp. 45-59.
Dianne M. Fishwild et al, "High-avidity human IgGk monoclonal antibodies from a novel strain of minilocus transgenic mice". Nature Biotechnology. vol. 14, Jul. 1996. pp. 845-851.
J. Kimble Frazer et al, "Immunoglobulins: Structure and Function", Fundamental Immunology, Fourth Edition, 1999, pp. 37-74.
Michael L. Gallo, et al, "The human immunoglobulin loci introduced into mice: V (D) and J gene segment usage similar to that of adult humans", Eur. J. lmmunol. 2000, 30: 534-540.
Martin J. Glennie et al, "Clinical trials of antibody therapy", Immunology Today, Aug. 2000. vol. 21, No. 8, pp. 403-410.
Ulf Grawunder et al, "Induction of sterile transcription from the kl chain gene locus in V (D) J recombinase-deficient progenitor B cells", International Immunology, Jul. 1995, vol. 7, No. 12, pp. 1915-1925.

(Continued)

*Primary Examiner*—Karen A Canella
(74) *Attorney, Agent, or Firm*—Sterne, Kessler, Goldstein & Fox P.L.L.C.

(57) ABSTRACT

The present invention generally relates to the fields of genetic engineering and antibody production. In particular, it relates to the generation of genetically modified vertebrate precursor lymphocytes that have the potential to differentiate into more mature lymphoid lineage cells, and to the use thereof for the production of any heterologous antibody or binding protein.

25 Claims, 26 Drawing Sheets

OTHER PUBLICATIONS

Ulf Grawunder et al, "Antigen receptor gene rearrangement", Current Opinion in Immunology, 1998, 10: pp. 172-180.
Ulf Grawunder et al, "DNA Ligase IV Is Essential for V(D)J Recombination and DNA Double-Strand Break Repair in Human Precursor Lymphocytes", Molecular Cell, Oct. 1998. vol. 2. pp. 477-484.
L.L. Green et al, "Antigen-specific human monoclonal antibodies from mice engineered with human Ig heavy and light chain YACs". Nature Genetics, vol. 7, May 1994, pp. 13-21.
Ed Harlow et al, "Chapter 6—Monoclonal Antibodies", Antibodies, A Laboratory Manual, Cold Spring Harbor Laboratory 1988, pp. 150-173.
Hennie R. Hoogenboom et al, "Natural and designer binding sites made by phage display technology", Immunology Today, Aug. 2000, vol. 21, No. 8, pp. 371-378.
Hennie R. Hoogenboom et al, "By-passing Immunisation Human Antibodies from Synthetic Repertoires of Germline Vh Gene Segments Rearranged in Vitro", Journal Molecular Biology, 1992, vol. 227, pp. 381-388.
N. N. Iscove et al, "Complete Replacement of Serum by Albumin, Transferrin, and Soybean Lipid in Cultures of Lipopolysaccharide-Reactive B Lymphocytes", The Journal of Experimental Medicine, vol. 147, 1978, pp. 923-933.
Aya Jakobovits, "Production of fully human antibodies by transgenic mice", Cell Genesys Inc., Foster City, USA, Current Opinion in Biotechnology 1995, 6:561-566.
Aya Jakobovits et al, "Production of Antigen-Specific Human Antibodies from Mice Engineered with Human Heavy and Light Chain YACs" Cell Genesys, Inc., Foster City, CA, Annals New York Academy of Sciences, pp. 525-535, 1995, vol. 764.
Matti Kaartinen et al, "Reading of D genes in variable frames as a source of antibody diversity", Immunology Today, vol. 6, No. 11, 1985, pp. 324-327.
Hajime Karasuyama et al, "Surrogate Light Chain in B Cell Development", Advances in Immunology, Jan. 1996, vol. 63, pp. 1-41.
John F. Kearney et al, "A New Mouse Myeloma Cell Line That Has Lost Immunoglobulin Expression But Permits the Construction of Antibody-Secreting Hybrid Cell Lines", The Journal of Immunology, vol. 123, No. 4, Oct. 1979, pp. 1548-1550.
Daisuke Kitamura et al, "Targeted disruption of u chain membrane exon causes loss of heavy-chain allelic exclusion", Nature, vol. 356, Mar. 12, 1992, pp. 154-156.
Achim Knappik et al, "Fully Synthetic Human Combinatorial Antibody Libraries (HuCAL) Based on Modular Consensus Frameworks and CDRs Randomized with Trinucleotides", Journal Molecular Biology, 2000, 296, pp. 57-86.
Hiro-Aki Kodama et al, "In Vitro Hemopoiesis Within a Microenvironment Created by MC3T3-G2/PA6 Preadipocytes", Journal of Cellular Physiology 118:233-240 (1984).
G. Kohler et al, "Derivation of specific antibody-producing tissue culture and tumor lines by cell fusion", Eur. J. Immunol. 1976. 6:511-519.
Ralf Kuhn et al, "Advances in gene targeting methods", Current Opinion in Immunology, 1997, 9: pp. 183-188.
Nils Lonberg et al, "Human Antibodies from Transgenic Mice", Intern. Rev. Immunol., vol. 13, 1995, pp. 65-93.
Dina Markowitz et al, "A Safe Packaging Line for Gene Transfer: Separating Viral Genes on Two Different Plasmids", Journal of Virology, Apr. 1988, vol. 62, No. 4, pp. 1120-1124.
Francoise Maxwell et al, "Cloning, Sequence Determination, and Expression in Transfected Cells of the Coding Sequence for the tox 176 Attenuated Diphtheria Toxin A Chain", Molecular and Cellular Biology, Apr. 1987, vol. 7, No. 4, pp. 1576-1579.
John McCafferty et al, "Phage antibodies: filamentous phage displaying antibody variable domains", Nature, vol. 348, Dec. 6, 1990, pp. 552-554.
James W. McCarrick III et al, "Positive-negative selection gene targeting with the diphtheria toxin A-chain gene in mouse embryonic stem cells", Transgenic Research 2, 1993, pp. 183-190.
Fritz Melchers et al, "Roles of IgH and L Chains and of Surrogate H and L Chains in the Development of Cells of the B Lymphocyte Lineage", Annu. Rev. Immunol., 1994, 12:209-25.
Fritz Melchers et al, "Positive and negative selection events during B lymphopoiesis", Current Opinion in Immunology 1995, 7:214-227.
Peter Mombaerts et al, "RAG-1-Deficient Mice Have No Mature B and T Lymphocytes", Cell, vol. 68, Mar. 6, 1992, pp. 869-877.
Minetaro Ogawa et al, "B cell ontogeny in murine embryo studied by a culture system with the monolayer of a stromal cell clone, ST2:B cell progenitor develops first in the embryonal body rather than in the yolk sac", The EMBO Journal, 1988, vol. 7, No. 5, pp. 1337-1343.
Antonius Rolink et al, "Immature Surface Ig+ B Cells Can Continue to Rearrange k and L Chain Gene Loci", J. Exp. Med., vol. 178, Oct. 1993, pp. 1263-1270.
A. Rolink et al, "Changes in Frequencies of Clonable Pre B Cells During Life in Different Lymphoid Organs of Mice", Blood, vol. 81. No. 9, May 1, 1993, pp. 2290-2300.
Antonius Rolink et al, "Long-term proliferating early pre B cell lines and clones with the potential to develop to surface Ig-positive, mitogen reactive B cells in vitro and in vivo", The EMBO Journal, 1991, vol. 10, No. 2, pp. 327-336.
Antonius Rolink et al, "The SCID but Not the RAG-2 Gene Product Is Required for Su-Se Heavy Chain Class Switching", Immunity, vol. 5, Oct. 1996, pp. 319-330.
Yoichi Shinkai et al. "RAG-2-Deficient Mice Lack Mature Lymphocytes Owing to Inability to Initiate V(D)J Rearrangement", Cell, vol. 68, Mar. 6, 1992, pp. 855-867.
A. Strasser et al, "Abnormalties of the Immune System Induced by Dysregulated bcl-2 Expression in Transgenic Mice", Current Topics in Microbiology and Immunology, vol. 166, Springer-Verlag Berlin-Heidelberg 1990, pp. 175-181.
Kazuma Tomizuka et al, "Double trans-chromosomic mice: Maintenance of two individual human chromosome fragments containing Ig heavy and k loci and expression of fully human antibodies", PNAS, Jan. 18, 2000, vol. 97, No. 2, pp. 722-727.
Susumu Tonegawa, "Somatic generation of antibody diversity", Nature, vol. 302, Apr. 14, 1983, pp. 575-581.
Thomas H. Winkler et al, "Interleukin-3 and Interleukin-7 Are Alternative Growth Factors for the Same B-Cell Precursors in the Mouse", Blood, vol. 85, No. 8, Apr. 15, 1995, pp. 2045-2051.
Alt, F.W., et al., "Multiple Immunoglobulin Heavy-Chain Gene Transcripts in Abelson Murine Leukemia Virus-Transformed Lymphoid Cell Lines," *Mol. Cell. Biol. 2*:386-400, American Society for Microbiology (1982).
Blaese, R.M., "Lymphocytes for gene therapy," *Hum. Gene Transf. 219*:137-145, John Libbey Eurotext (1991).
Geraghty, P.J., and Mule, J.J., "Chapter 7: Genetically modified lymphocytes and hematopoietic stem cells as therapeutic vehicles," in *Gene Therapy in the Treatment of Cancer*, Huber, B.E., and Magrath, I., eds., Cambridge University Press, London, England, pp. 137-148 (1998).
Ochi, A., and Hozumi, N., "Introduction of antibody genes into lymphoid cells," *Metabolism 21*:1563-1569, W.B. Saunders (1984).
Persiani, D.M., et al., "Active λ And κ Antibody Gene Rearrangement In Abelson Murine Leukemia Virus-Transformed Pre-B Cell Lines," *J. Exp. Med. 165*:1655-1674, Rockefeller University Press (1987).
Potter, H., et al., "Enhancer-dependent expression of human κ immunoglobulin genes introduced into mouse pre-B lymphocytes by electroporation," *Proc. Natl. Acad. Sci. U.S.A. 81*:7161-7165, National Academy of Sciences (1984).
Roberts, M.R., et al., "Antigen-Specific Cytolysis by Neutrophils and NK Cells Expressing Chimeric Immune Receptors Bearing ζ or γ Signaling Domains," *J. Immunol. 161*:375-384, The American Association of Immunologists (1998).
Spanopoulou, E., et al., "Functional immunoglobulin transgenes guide ordered B-cell differentiation in Rag-1-deficient mice," *Genes Dev. 8*:1030-1042, Cold Spring Harbor Laboratory Press (1994).
Partial English Translation of Ochi, A., and Hozumi, N., "Introduction of antibody genes into lymphoid cells," *Metabolism 21*:1563-1569, W.B. Saunders (1984).
Patent Abstracts of Japan, English Abstract of JP 05-184386 (Cited as Document FP1), 1993.
Patent Abstracts of Japan, English Abstract of JP 10-146194 (Cited as Document FP2), 1998.

* cited by examiner

SEQUENCE LISTING

```
<160> NUMBER OF SEQ ID NOS: 98

<210> SEQ ID NO 1
<211> LENGTH: 4953
<212> TYPE: DNA
```

-continued

<213> ORGANISM: Artificial Sequence
<220> FEATURE:
<223> OTHER INFORMATION: Description of Artificial Sequence: pPGK-hygro; Template for amplification of hygromycin B

<400> SEQUENCE: 1

```
aaattgtaaa cgttaatatt ttgttaaaat tcgcgttaaa tttttgttaa atcagctcat     60

tttttaacca ataggccgaa atcggcaaaa tcccttataa atcaaaagaa tagaccgaga    120

tagggttgag tgttgttcca gtttggaaca agagtccact attaaagaac gtggactcca    180

acgtcaaagg gcgaaaaacc gtctatcagg gcgatggccc actacgtgaa ccatcaccct    240

aatcaagttt tttggggtcg aggtgccgta aagcactaaa tcggaaccct aaagggagcc    300

cccgatttag agcttgacgg ggaaagccgg cgaacgtggc gagaaaggaa gggaagaaag    360

cgaaaggagc gggcgctagg gcgctggcaa gtgtagcggt cacgctgcgc gtaaccacca    420

cacccgccgc gcttaatgcg ccgctacagg gcgcgtccca ttcgccattc aggctacgca    480

actgttggga agggcgatcg gtgcgggcct cttcgctatt acgccagctg gcgaaggggg    540

gatgtgctgc aaggcgatta agttgggtaa cgccagggtt ttcccagtca cgacgttgta    600

aaacgacggc cagtgaattg taatacgact cactataggg cgaattgggt accgggcccc    660

ccctcgaggt cgacggtatc gataagcttc tgatggaatt agaacttggc aaaacaatac    720

tgagaatgaa gtgtatgtgg aacagaggct gctgatctcg ttcttcaggc tatgaaactg    780

acacatttgg aaaccacagt acttagaacc acaaagtggg aatcaagaga aaaacaatga    840

tcccacgaga atttatagat ctatagatca tgagtgggag gaatgagctg gcccttaatt    900

tggttttgct tgtttaaatt atgatatcca actatgaaac attatcataa agcaatagta    960

aagagccttc agtaaagagc aggcatttat ctaatcccac cccacccca cccccgtagc    1020

tccatccttc cttcaaaatg taggtactct gttctcaccc ttcttaacaa agtatgacag   1080

gaaaaacttc cattttagtg gacatcttta ttgtttaata gatcatcaat ttctgcatac   1140

tctattcctt tgccctcgga cgagtgctgg ggcgtcggtt tccactatcg gcgagtactt   1200

ctacacagcc atcggtccag acggccgcgc ttctgcgggc gatttgtgta cgcccgacag   1260

tcccggctcc ggatcggacg attgcgtcgc atcgaccctg cgcccaagct gcatcatcga   1320

aattgccgtc aaccaagctc tgatagagtt ggtcaagacc aatgcggagc atatacgccc   1380

ggagccgcgg cgatcctgca agctccggat gcctccgctc gaagtagcgc gtctgctgct   1440

ccatacaagc caaccacggc ctccagaaga agatgttggc gacctcgtat tgggaatccc   1500

cgaacatcgc ctcgctccag tcaatgaccg ctgttatgcg gccattgtcc gtcaggacat   1560

tgttggagcc gaaatccgcg tgcacgaggt gccggacttc ggggcagtcc tcggcccaaa   1620

gcatcagctc atcgagagcc tgcgcgacgg acgcactgac ggtgtcgtcc atcacagttt   1680

gccagtgata cacatgggga tcagcaatcg cgcatatgaa atcacgccat gtagtgtatt   1740

gaccgattcc ttgcggtccg aatgggccga acccgctcgt ctggctaaga tcggccgcag   1800

cgatcgcatc catggcctcc gcgaccggct gcagaacagc gggcagttcg gtttcaggca   1860

ggtcttgcaa cgtgacaccc tgtgcacggc gggagatgca ataggtcagg ctctcgctga   1920

attccccaat gtcaagcact tccggaatcg ggagcgcggc cgatgcaaag tgccgataaa   1980

cataacgatc tttgtagaaa ccatcggcgc agctatttac ccgcaggaca tatccacgcc   2040

ctcctacatc gaagctgaaa gcacgagatt cttcgccctc cgagagctgc atcaggtcgg   2100

agacgctgtc gaacttttcg atcagaaact tctcgacaga cgtcgcggtg agttcaggct   2160
```

-continued

```
ttttcatggt ggcgggatgc aggtcgaaag gcccggagat gaggaagagg agaacagcgc   2220
ggcagacgtg cgcttttgaa gcgtgcagaa tgccgggcct ccggaggacc ttcgggcgcc   2280
cgccccgccc ctgagcccgc ccctgagccc gcccccggac ccacccccttc ccagcctctg   2340
agcccagaaa gcgaaggagc aaagctgcta ttggccgttg ccccaaaggc ctacccgctt   2400
ccattgctca gcggtgctgt ccatctgcac gagactagtg agacgtgcta cttccatttg   2460
tcacgtcctg ctcgacgcga gctgcggggc gggggggaaa cttcctgact aggggaggag   2520
tagaaggtgg cgcgaagggg ccaccaaaga acggagccgg ttggcgccta ccggtggatg   2580
tggaatgtgt gcgaggccag aggccacttg tgtagcgcca agtgcccagc ggggctgcta   2640
aagcgcatgc tccagactgc cttgggaaaa gcgcctcccc tacccggtag aattcctgca   2700
gcccggggga tccactagtt ctagagcggc cgccaccgcg gtggagctcc agcttttgtt   2760
ccctttagtg agggttaatt ccgagcttgg cgtaatcatg gtcatagctg tttcctgtgt   2820
gaaattgtta tccgctcaca attccacaca acataggagc cggaagcata aagtgtaaag   2880
cctggggtgc ctaatgagtg aggtaactca cattaattgc gttgcgctca ctgcccgctt   2940
tccagtcggg aaacctgtcg tgccagctgc attaatgaat cggccaacgc gcggggagag   3000
gcggtttgcg tattgggcgc tcttccgctt cctcgctcac tgactcgctg cgctcggtcg   3060
ttcggctgcg gcgagcggta tcagctcact caaaggcggt aatacggtta tccacagaat   3120
caggggataa cgcaggaaag aacatgtgag caaaaggcca gcaaaaggcc aggaaccgta   3180
aaaaggccgc gttgctggcg tttttccata ggctcggccc ccctgacgag catcacaaaa   3240
atcgacgctc aagtcagagg tggcgaaacc cgacaggact ataaagatac caggcgttcc   3300
ccctggaag ctccctcgtg cgctctcctg ttccgaccct gccgcttacc ggatacctgt   3360
ccgcctttct cccttcggga agcgtggcgc tttctcaatg ctcacgctgt aggtatctca   3420
gttcggtgta ggtcgttcgc tccaagctgg gctgtgtgca cgaacccccc gttcagcccg   3480
accgctgcgc cttatccggt aactatcgtc ttgagtccaa cccggtaaga cacgacttat   3540
cgccactggc agcagccact ggtaacagga ttagcagagc gaggtatgta ggcggtgcta   3600
cagagttctt gaagtggtgg cctaactacg gctacactag aaggacagta tttggtatct   3660
gcgctctgct gaagccagtt accttcggaa aaagagttgg tagctcttga tccggcaaac   3720
aaaccaccgc tggtagcggt ggtttttttg tttgcaagca gcagattacg cgcagaaaaa   3780
aaggatctca agaagatcct ttgatctttt ctacggggtc tgacgctcag tggaacgaaa   3840
actcacgtta agggattttg gtcatgagat tatcaaaaag gatcttcacc tagatccttt   3900
taaattaaaa atgaagtttt aaatcaatct aaagtatata tgagtaaact tggtctgaca   3960
gttaccaatg cttaatcagt gaggcaccta tctcagcgat ctgtctattt cgttcatcca   4020
tagttgcctg actgcccgtc gtgtagataa ctacgatacg ggagggctta ccatctggcc   4080
ccagtgctgc aatgataccg cgagacccac gctcaccggc tccagattta tcagcaataa   4140
accagccagc cggaagggcc gagcgcagaa gtggtcctgc aactttatcc gcctccatcc   4200
agtctattaa ttgttgccgg gaagctagag taagtagttc gccagttaat agtttgcgca   4260
acgttgttgc cattgctaca ggcatcgtgg tgtcacgctc gtcgtttggt atggcttcat   4320
tcagctccgg ttcccaacga tcaaggcgag ttacatgatc ccccatgttg tgaaaaaaag   4380
cggttagctc cttcggtcct ccgatcgttg tcagaagtaa gttggccgca gtgttatcac   4440
tcatgcttat ggcagcactg cataattctc ttactgtcat gccatccgta agatgctttt   4500
ctgtgactgg tgagtactca accaagtcat tctgagaata gtgtatgcgg cgaccgagtt   4560
```

-continued gctcttgccc ggcgtcaata cgggataata ccgcgccaca tagcagaact ttaaaagtgc 4620
tcatcattgg aaaacgttct tcggggcgaa aactctcaag gatcttaccg ctgttgagat 4680
ccagttcgat gtaacccact cgtgcaccca actgatcttc agcatctttt actttcacca 4740
gcgtttctgg gtgagcaaaa acaggaaggc aaaatgccgc aaaaaaggga ataagggcga 4800
cacggaaatg ttgaatactc atactcttcc tttttcaata ttattgaagc atttatcagg 4860
gttattgtct catgagcgga tacatatttg aatgtattta gaaaaataaa caaatagggg 4920
ttccgcgcac atttccccga aaagtgccac ctg 4953

<210> SEQ ID NO 2
<211> LENGTH: 5130
<212> TYPE: DNA
<213> ORGANISM: Artificial Sequence
<220> FEATURE:
<223> OTHER INFORMATION: Description of Artificial Sequence: pBS-DT4;
Template for amplification of wt diphteria toxin A

<400> SEQUENCE: 2
aaattgtaaa cgttaatatt ttgttaaaat tcgcgttaaa tttttgttaa atcagctcat 60
tttttaacca ataggccgaa atcggcaaaa tcccttataa atcaaaagaa tagaccgaga 120
tagggttgag tgttgttcca gtttggaaca agagtccact attaaagaac gtggactcca 180
acgtcaaagg gcgaaaaacc gtctatcagg gcgatggccc actacgtgaa ccatcaccct 240
aatcaagttt tttggggtcg aggtgccgta aagcactaaa tcggaaccct aaagggagcc 300
cccgatttag agcttgacgg ggaaagccgg cgaacgtggc gagaaaggaa gggaagaaag 360
cgaaaggagc gggcgctagg gcgctggcaa gtgtagcggt cacgctgcgc gtaaccacca 420
cacccgccgc gcttaatgcg ccgctacagg gcgcgtccca ttcgccattc aggctacgca 480
actgttggga agggcgatcg gtgcgggcct cttcgctatt acgccagctg gcgaaggggg 540
gatgtgctgc aaggcgatta agttgggtaa cgccagggtt ttcccagtca cgacgttgta 600
aaacgacggc cagtgaattg taatacgact cactataggg cgaattgggt accgggcccc 660
ccctcgaggt cgacggtatc gataagcttg atatcgaatt cctgcagccc gggggatcca 720
ctagttctag agcttgcaga tctgcattcc accactgctc ccattcatca gttccatagg 780
ttggaatcta aaatacacaa acaattagaa tcagtagttt aacacattat acacttaaaa 840
attttatatt taccttagag ctttaaatct ctgtaggtag tttgtccaat tatgtcacac 900
cacagaagta aggttccttc acaaagagat cgcctgacac gatttcctgc acaggcttga 960
gccatatact catacatcgc atcttggcca cgttttccac gggtttcaaa attaatctca 1020
agttctacgc ttaacgcttt cgcctgttcc cagttattaa tatattcaac gctagaactc 1080
ccctcagcga agggaaggct gagcactaca cgcgaagcac catcaccgaa ccttttgata 1140
aactcttccg ttccgacttg ctccatcaac ggttcagtga gacttaaacc taactctttc 1200
ttaatagttt cggcattatc cacttttagt gcgagaacct tcgtcagtcc tggatacgtc 1260
actttgacca cgcctccagc ttttccagag agcgggtttt cattatctac agagtatccc 1320
gcagcgtcgt atttattgtc ggtactataa aaccctttcc aatcatcgtc ataatttcct 1380
tgtgtaccag attttggctt ttgtatacct ttttgaatgg aatctacata accaggttta 1440
gtcccgtggt acgaagaaaa gttttccatc acaaaagatt tagaagaatc aacaacatca 1500
tcaggatcca tggcgaacta tcaagacaca aaagaaggct atagtcacct cggggccgcc 1560
aagagcagcc gctgccgccc tgcccacttc cggcaagccg cgggctcgag ccgccagggg 1620

-continued

```
gcgcgcgccc aagctcaggg gacaaaggaa gcgcagaccg gccgcattat taccataaaa   1680
ggcaaacgct ggcccggagg cggacctagg gcaggaagcc agacctccgc cccctcccca   1740
aacgggcgca agctccgcct acactgcgcc gacgggcggc ttgtgcgcgc gcgggaggcg   1800
accacaccca gcaggaagcg caaacaaggc gcccgtgcca ctgtgacccc gccccttccg   1860
gacaacggcc ccgccctcgc ccaaccccgg gcagccgcgc tcccagcctc aatacgcacg   1920
cgcagctaac taggaagagg gggagagaag agctccctcc ctagcgcaca cgcgcctcga   1980
tgcccagtga tagagagcgc acgcgcagtg gcatcccagc cccacccgg ccgagccggc    2040
cctgccgcgc ccgcccgccc gcccgcccgc ccggcaagcc gaataggcaa accggtttgg   2100
acaaagaccc agaggccatt gaggcgtgat cgtagcgtct ggttcccaat actgtgtact   2160
ctcaagatgg acctaatacg gcttttaaca cccgcaagcc gcaccggctc atcaaatgcc   2220
cacaccgcga ccctagtgtg tccccaagcc ccacgcaccg agcgggagcg ggcccacgag   2280
tgtctacacc gcgggaatgt ggctgcaaag agtctacacg ctaggcgtaa agttggctgt   2340
gccagtgtcc gctccgcggc ccggcaccac cctccacccg cccatggtgt ccgttctgag   2400
tgatcctcag gaccctgcag tgaggtacta gccacgagag agcgaaggcc cgctgggccc   2460
ggcgtccctg cttacctggt ggcgggtgtg gaccggcaac gaaggagctg caaagaagct   2520
gtgctcgcgg gtggacgcga ctcgacagtg gctgcgcgtt gcgccgccgg gttttatagg   2580
acgccacagc ggccactcga gccataaaag gcaactttcg gaacggcggg cgctgattgg   2640
ctccgcgtcg ctcactcacc ggcctcgccg cacagtgcag cattttttta cccctctcc    2700
cctccttttg aaaaaaaaaa aaaaaaagaa gaagaaaaaa aaaaaaagcg agagagaaag   2760
cgagattgag gaagaggatg aagagttttg gcgatgggtg ctggctccgt aggcccagat   2820
gtacaggaat agcctccgcc cttgtggaca ctgccccatt caatgtctcg gttactaggg   2880
ggtaccgagc tcgaattcta gagcggccgc caccgcggtg gagctccagc ttttgttccc   2940
tttagtgagg gttaattccg agcttggcgt aatcatggtc atagctgttt cctgtgtgaa   3000
attgttatcc gctcacaatt ccacacaaca taggagccgg aagcataaag tgtaaagcct   3060
ggggtgccta atgagtgagg taactcacat taattgcgtt gcgctcactg cccgctttcc   3120
agtcgggaaa cctgtcgtgc cagctgcatt aatgaatcgg ccaacgcgcg gggagaggcg   3180
gtttgcgtat tgggcgctct tccgcttcct cgctcactga ctcgctgcgc tcggtcgttc   3240
ggctgcggcg agcggtatca gctcactcaa aggcggtaat acggttatcc acagaatcag   3300
gggataacgc aggaaagaac atgtgagcaa aaggccagca aaaggccagg aaccgtaaaa   3360
aggccgcgtt gctggcgttt ttccataggc tcggcccccc tgacgagcat cacaaaaatc   3420
gacgctcaag tcagaggtgg cgaaacccga caggactata aagataccag gcgttccccc   3480
ctggaagctc cctcgtgcgc tctcctgttc cgaccctgcc gcttaccgga tacctgtccg   3540
cctttctccc ttcgggaagc gtggcgcttt ctcaatgctc acgctgtagg tatctcagtt   3600
cggtgtaggt cgttcgctcc aagctgggct gtgtgcacga accccccgtt cagcccgacc   3660
gctgcgcctt atccggtaac tatcgtcttg agtccaaccc ggtaagacac gacttatcgc   3720
cactggcagc agccactggt aacaggatta gcagagcgag gtatgtaggc ggtgctacag   3780
agttcttgaa gtggtggcct aactacggct acactagaag gacagtattt ggtatctgcg   3840
ctctgctgaa gccagttacc ttcggaaaaa gagttggtag ctcttgatcc ggcaaacaaa   3900
ccaccgctgg tagcggtggt ttttttgttt gcaagcagca gattacgcgc agaaaaaaag   3960
```

-continued

```
gatctcaaga agatcctttg atcttttcta cggggtctga cgctcagtgg aacgaaaact   4020

cacgttaagg gattttggtc atgagattat caaaaaggat cttcacctag atccttttaa   4080

attaaaaatg aagttttaaa tcaatctaaa gtatatatga gtaaacttgg tctgacagtt   4140

accaatgctt aatcagtgag gcacctatct cagcgatctg tctatttcgt tcatccatag   4200

ttgcctgact gcccgtcgtg tagataacta cgatacggga gggcttacca tctggcccca   4260

gtgctgcaat gataccgcga gacccacgct caccggctcc agatttatca gcaataaacc   4320

agccagccgg aagggccgag cgcagaagtg gtcctgcaac tttatccgcc tccatccagt   4380

ctattaattg ttgccgggaa gctagagtaa gtagttcgcc agttaatagt ttgcgcaacg   4440

ttgttgccat tgctacaggc atcgtggtgt cacgctcgtc gtttggtatg gcttcattca   4500

gctccggttc ccaacgatca aggcgagtta catgatcccc catgttgtga aaaaaagcgg   4560

ttagctcctt cggtcctccg atcgttgtca gaagtaagtt ggccgcagtg ttatcactca   4620

tgcttatggc agcactgcat aattctctta ctgtcatgcc atccgtaaga tgcttttctg   4680

tgactggtga gtactcaacc aagtcattct gagaatagtg tatgcggcga ccgagttgct   4740

cttgcccggc gtcaatacgg gataataccg cgccacatag cagaacttta aaagtgctca   4800

tcattggaaa acgttcttcg gggcgaaaac tctcaaggat cttaccgctg ttgagatcca   4860

gttcgatgta acccactcgt gcacccaact gatcttcagc atcttttact ttcaccagcg   4920

tttctgggtg agcaaaaaca ggaaggcaaa atgccgcaaa aaagggaata agggcgacac   4980

ggaaatgttg aatactcata ctcttccttt ttcaatatta ttgaagcatt tatcagggtt   5040

attgtctcat gagcggatac atatttgaat gtatttagaa aaataaacaa ataggggttc   5100

cgcgcacatt tccccgaaaa gtgccacctg                                     5130
```

<210> SEQ ID NO 3
<211> LENGTH: 5130
<212> TYPE: DNA
<213> ORGANISM: Artificial Sequence
<220> FEATURE:
<223> OTHER INFORMATION: Description of Artificial Sequence: pBS-DT4tox176; Template for amplification of attenuated diphteria toxin A

<400> SEQUENCE: 3

```
aaattgtaaa cgttaatatt ttgttaaaat tcgcgttaaa tttttgttaa atcagctcat     60

tttttaacca ataggccgaa atcggcaaaa tcccttataa atcaaaagaa tagaccgaga    120

tagggttgag tgttgttcca gtttggaaca agagtccact attaaagaac gtggactcca    180

acgtcaaagg gcgaaaaacc gtctatcagg gcgatggccc actacgtgaa ccatcaccct    240

aatcaagttt tttggggtcg aggtgccgta aagcactaaa tcggaaccct aaagggagcc    300

cccgatttag agcttgacgg ggaaagccgg cgaacgtggc gagaaaggaa gggaagaaag    360

cgaaaggagc gggcgctagg gcgctggcaa gtgtagcggt cacgctgcgc gtaaccacca    420

cacccgccgc gcttaatgcg ccgctacagg gcgcgtccca ttcgccattc aggctacgca    480

actgttggga agggcgatcg gtgcgggcct cttcgctatt acgccagctg gcgaaggggg    540

gatgtgctgc aaggcgatta agttgggtaa cgccagggtt ttcccagtca cgacgttgta    600

aaacgacggc cagtgaattg taatacgact cactataggg cgaattgggt accgggcccc    660

ccctcgaggt cgacggtatc gataagcttg atatcgaatt cctgcagccc gggggatcca    720

ctagttctag agcttgcaga tctgcattcc accactgctc ccattcatca gttccatagg    780

ttggaatcta aaatacacaa acaattagaa tcagtagttt aacacattat acacttaaaa    840
```

-continued

```
attttatatt taccttagag ctttaaatct ctgtaggtag tttgtccaat tatgtcacac    900
cacagaagta aggttccttc acaaagagat cgcctgacac gatttcctgc acaggcttga    960
gccatatact catacatcgc atcttggcca cgttttccac gggtttcaaa attaatctca   1020
agttctacgc ttaacgcttt cgcctgttcc cagttattaa tatattcaac gctagaactc   1080
ccctcagcga agggaaggct gagcactaca cggctagcac catcatcgaa ccttttgata   1140
aactcttccg ttccgacttg ctccatcaac ggttcagtga gacttaaacc taactctttc   1200
ttaatagttt cggcattatc cacttttagt gcgagaacct tcgtcagtcc tggatacgtc   1260
actttgacca cgcctccagc ttttccagag agcgggtttt cattatctac agagtatccc   1320
gcagcgtcgt atttattgtc ggtactataa aaccctttcc aatcatcgtc ataatttcct   1380
tgtgtaccag attttggctt ttgtatacct ttttgaatgg aatctacata accaggttta   1440
gtcccgtggt acgaagaaaa gttttccatc acaaaagatt tagaagaatc aacaacatca   1500
tcaggatcca tggcgaacta tcaagacaca aaagaaggct atagtcacct cggggccgcc   1560
aagagcagcc gctgccgccc tgcccacttc cggcaagccg cgggctcgag ccgccagggg   1620
gcgcgcgccc aagctcaggg gacaaaggaa gcgcagaccg gccgcattat taccataaaa   1680
ggcaaacgct ggcccggagg cggacctagg gcaggaagcc agacctccgc cccctcccca   1740
aacgggcgca agctccgcct acactgcgcc gacgggcggc ttgtgcgcgc gcgggaggcg   1800
accacaccca gcaggaagcg caaacaaggc gcccgtgcca ctgtgacccc gccccttccg   1860
gacaacggcc ccgccctcgc ccaaccccgg gcagccgcgc tcccagcctc aatacgcacg   1920
cgcagctaac taggaagagg gggagagaag agctccctcc ctagcgcaca cgcgcctcga   1980
tgcccagtga tagagagcgc acgcgcagtg gcatcccagc ccccacccgg ccgagccggc   2040
cctgccgcgc ccgcccgccc gcccgcccgc ccggcaagcc gaataggcaa accggtttgg   2100
acaaagaccc agaggccatt gaggcgtgat cgtagcgtct ggttcccaat actgtgtact   2160
ctcaagatgg acctaatacg gcttttaaca cccgcaagcc gcaccggctc atcaaatgcc   2220
cacaccgcga ccctagtgtg tccccaagcc ccacgcaccg agcgggagcg ggcccacgag   2280
tgtctacacc gcgggaatgt ggctgcaaag agtctacacg ctaggcgtaa agttggctgt   2340
gccagtgtcc gctccgcggc ccggcaccac cctccacccg cccatggtgt ccgttctgag   2400
tgatcctcag gaccctgcag tgaggtacta gccacgagag agcgaaggcc cgctgggccc   2460
ggcgtccctg cttacctggt ggcgggtgtg gaccggcaac gaaggagctg caaagaagct   2520
gtgctcgcgg gtggacgcga ctcgacagtg gctgcgcgtt gcgccgccgg gttttatagg   2580
acgccacagc ggccactcga gccataaaag gcaactttcg gaacggcggg cgctgattgg   2640
ctccgcgtcg ctcactcacc ggcctcgccg cacagtgcag catttttta cccccctctcc   2700
cctccttttg aaaaaaaaaa aaaaaaagaa gaagaaaaaa aaaaaaagcg agagagaaag   2760
cgagattgag gaagaggatg aagagttttg gcgatgggtg ctggctccgt aggcccagat   2820
gtacaggaat agcctccgcc cttgtggaca ctgccccatt caatgtctcg gttactaggg   2880
ggtaccgagc tcgaattcta gagcggccgc caccgcggtg gagctccagc ttttgttccc   2940
tttagtgagg gttaattccg agcttggcgt aatcatggtc atagctgttt cctgtgtgaa   3000
attgttatcc gctcacaatt ccacacaaca taggagccgg aagcataaag tgtaaagcct   3060
ggggtgccta atgagtgagg taactcacat taattgcgtt gcgctcactg cccgctttcc   3120
agtcgggaaa cctgtcgtgc cagctgcatt aatgaatcgg ccaacgcgcg gggagaggcg   3180
```

-continued

```
gtttgcgtat tgggcgctct tccgcttcct cgctcactga ctcgctgcgc tcggtcgttc   3240
ggctgcggcg agcggtatca gctcactcaa aggcggtaat acggttatcc acagaatcag   3300
gggataacgc aggaaagaac atgtgagcaa aaggccagca aaaggccagg aaccgtaaaa   3360
aggccgcgtt gctggcgttt ttccataggc tcggcccccc tgacgagcat cacaaaaatc   3420
gacgctcaag tcagaggtgg cgaaacccga caggactata aagataccag gcgttccccc   3480
ctggaagctc cctcgtgcgc tctcctgttc cgaccctgcc gcttaccgga tacctgtccg   3540
cctttctccc ttcgggaagc gtggcgcttt ctcaatgctc acgctgtagg tatctcagtt   3600
cggtgtaggt cgttcgctcc aagctgggct gtgtgcacga accccccgtt cagcccgacc   3660
gctgcgcctt atccggtaac tatcgtcttg agtccaaccc ggtaagacac gacttatcgc   3720
cactggcagc agccactggt aacaggatta gcagagcgag gtatgtaggc ggtgctacag   3780
agttcttgaa gtggtggcct aactacggct acactagaag gacagtattt ggtatctgcg   3840
ctctgctgaa gccagttacc ttcggaaaaa gagttggtag ctcttgatcc ggcaaacaaa   3900
ccaccgctgg tagcggtggt ttttttgttt gcaagcagca gattacgcgc agaaaaaaag   3960
gatctcaaga agatcctttg atcttttcta cggggtctga cgctcagtgg aacgaaaact   4020
cacgttaagg gattttggtc atgagattat caaaaaggat cttcacctag atccttttaa   4080
attaaaaatg aagttttaaa tcaatctaaa gtatatatga gtaaacttgg tctgacagtt   4140
accaatgctt aatcagtgag gcacctatct cagcgatctg tctatttcgt tcatccatag   4200
ttgcctgact gcccgtcgtg tagataacta cgatacggga gggcttacca tctggcccca   4260
gtgctgcaat gataccgcga gacccacgct caccggctcc agatttatca gcaataaacc   4320
agccagccgg aagggccgag cgcagaagtg gtcctgcaac tttatccgcc tccatccagt   4380
ctattaattg ttgccgggaa gctagagtaa gtagttcgcc agttaatagt ttgcgcaacg   4440
ttgttgccat tgctacaggc atcgtggtgt cacgctcgtc gtttggtatg gcttcattca   4500
gctccggttc ccaacgatca aggcgagtta catgatcccc catgttgtga aaaaaagcgg   4560
ttagctcctt cggtcctccg atcgttgtca gaagtaagtt ggccgcagtg ttatcactca   4620
tgcttatggc agcactgcat aattctctta ctgtcatgcc atccgtaaga tgcttttctg   4680
tgactggtga gtactcaacc aagtcattct gagaatagtg tatgcggcga ccgagttgct   4740
cttgcccggc gtcaatacgg gataataccg cgccacatag cagaacttta aaagtgctca   4800
tcattggaaa acgttcttcg gggcgaaaac tctcaaggat cttaccgctg ttgagatcca   4860
gttcgatgta acccactcgt gcacccaact gatcttcagc atcttttact ttcaccagcg   4920
tttctgggtg agcaaaaaca ggaaggcaaa atgccgcaaa aaagggaata agggcgacac   4980
ggaaatgttg aatactcata ctcttccttt ttcaatatta ttgaagcatt tatcagggtt   5040
attgtctcat gagcggatac atatttgaat gtatttagaa aaataaacaa ataggggttc   5100
cgcgcacatt tccccgaaaa gtgccacctg                                     5130
```

```
<210> SEQ ID NO 4
<211> LENGTH: 4514
<212> TYPE: DNA
<213> ORGANISM: Artificial Sequence
<220> FEATURE:
<223> OTHER INFORMATION: Description of Artificial Sequence: pGL2neo(+);
      Template for amplification of loxP site flanked
      neomycin

<400> SEQUENCE: 4

cgacgtcgca tgctcccggc cgccatggcc gcgggatatc actagtgcgg ccgcctgcag     60
```

-continued

```
gtcgaccata tgggagagct cgaattcgag ctcggtaccc tcgacctgca gccaagctag    120
cttggctgga cgtaaactcc tcttcagacc taataacttc gtatagcata cattatacga    180
agttatatta agggttattg aatatgatcg gaattcctcg agatccgaac aaacgaccca    240
acacccgtgc gttttattct gtctttttat tgccgatccc ctcagaagaa ctcgtcaaga    300
aggcgataga aggcgatgcg ctgcgaatcg ggagcggcga taccgtaaag cacgaggaag    360
cggtcagccc attcgccgcc aagctcttca gcaatatcac gggtagccaa cgctatgtcc    420
tgatagcggt ccgccacacc cagccggcca cagtcgatga atccagaaaa gcggccattt    480
tccaccatga tattcggcaa gcaggcatcg ccatgggtca cgacgagatc ctcgccgtcg    540
ggcatgcgcg ccttgagcct ggcgaacagt tcggctggcg cgagcccctg atgctcttcg    600
tccagatcat cctgatcgac aagaccggct tccatccgag tacgtgctcg ctcgatgcga    660
tgtttcgctt ggtggtcgaa tgggcaggta gccggatcaa gcgtatgcag ccgccgcatt    720
gcatcagcca tgatggatac tttctcggca ggagcaaggt gagatgacag gagatcctgc    780
cccggcactt cgcccaatag cagccagtcc cttcccgctt cagtgacaac gtcgagcaca    840
gctgcgcaag gaacgcccgt cgtggccagc cacgatagcc gcgctgcctc gtcctgcagt    900
tcattcaggg caccggacag gtcggtcttg acaaaaagaa ccgggcgccc ctgcgctgac    960
agccggaaca cggcggcatc agagcagccg attgtctgtt gtgcccagtc atagccgaat   1020
agcctctcca cccaagcggc cggagaacct gcgtgcaatc catcttgttc aatggccgat   1080
cccatattgg ctgcagggtc gctcgctcgg tgttcgaggc cacacgcgtc accttaatat   1140
gcgaagtgga cctgggaccg cgccgccccg actgcatctg cgtgttcgaa ttcgccaatg   1200
acaagacgct gggcggggtt tgctcgacat tgggtggaaa cattccaggc ctgggtggag   1260
aggctttttg cttcctcttg caaaaccaca ctgctcgaca ttgggtggaa acattccagg   1320
cctgggtgga gaggcttttt gcttcctctt gcaaaaccac actgctcgac ctgcagccaa   1380
gctagcttgg ctggacgtaa actcctcttc agacctaata acttcgtata gcatacatta   1440
tacgaagtta tattaagggt tattgaatat gatcggaatt cctcgagtct agggggatcc   1500
tctagagtcg acctgcaggc atgctcccgg ccgccatggc cgcgggatat cactagtgcg   1560
gccgcctgca ggtcgaccat atgggagagc tcccaacgcg ttggatgcat agcttgagta   1620
ttctatagtg tcacctaaat agcttggcgt aatcatggtc atagctgttt cctgtgtgaa   1680
attgttatcc gctcacaatt ccacacaaca tacgagccgg aagcataaag tgtaaagcct   1740
ggggtgccta atgagtgagc taactcacat taattgcgtt gcgctcactg cccgctttcc   1800
agtcgggaaa cctgtcgtgc cagctgcatt aatgaatcgg ccaacgcgcg gggagaggcg   1860
gtttgcgtat tgggcgctct tccgcttcct cgctcactga ctcgctgcgc tcggtcgttc   1920
ggctgcggcg agcggtatca gctcactcaa aggcggtaat acggttatcc acagaatcag   1980
gggataacgc aggaaagaac atgtgagcaa aaggccagca aaaggccagg aaccgtaaaa   2040
aggccgcgtt gctggcgttt ttcgataggc tccgcccccc tgacgagcat cacaaaaatc   2100
gacgctcaag tcagaggtgg cgaaacccga caggactata aagataccag gcgtttcccc   2160
ctggaagctc cctcgtgcgc tctcctgttc cgaccctgcc gcttaccgga tacctgtccg   2220
cctttctccc ttcgggaagc gtggcgcttt ctcatagctc acgctgtagg tatctcagtt   2280
cggtgtaggt cgttcgctcc aagctgggct gtgtgcacga accccccgtt cagcccgacc   2340
gctgcgcctt atccggtaac tatcgtcttg agtccaaccc ggtaagacac gacttatcgc   2400
```

-continued

```
cactggcagc agccactggt aacaggatta gcagagcgag gtatgtaggc ggtgctacag   2460

agttcttgaa gtggtggcct aactacggct acactagaag gacagtattt ggtatctgcg   2520

ctctgctgaa gccagttacc ttcggaaaaa gagttggtag ctcttgatcc ggcaaacaaa   2580

ccaccgctgg tagcggtggt ttttttgttt gcaagcagca gattacgcgc agaaaaaaag   2640

gatctcaaga agatcctttg atcttttcta cggggtctga cgctcagtgg aacgaaaact   2700

cacgttaagg gattttggtc atgagattat caaaaaggat cttcacctag atccttttaa   2760

attaaaaatg aagttttaaa tcaatctaaa gtatatatga gtaaacttgg tctgacagtt   2820

accaatgctt aatcagtgag gcacctatct cagcgatctg tctatttcgt tcatccatag   2880

ttgcctgact ccccgtcgtg tagataacta cgatacggga gggcttacca tctggcccca   2940

gtgctgcaat gataccgcga gacccacgct caccggctcc agatttatca gcaataaacc   3000

agccagccgg aagggccgag cgcagaagtg gtcctgcaac tttatccgcc tccatccagt   3060

ctattaattg ttgccgggaa gctagagtaa gtagttcgcc agttaatagt ttgcgcaacg   3120

ttgttggcat tgctacaggc atcgtggtgt cacgctcgtc gtttggtatg gcttcattca   3180

gctccggttc ccaacgatca aggcgagtta catgatcccc catgttgtgc aaaaaagcgg   3240

ttagctcctt cggtcctccg atcgttgtca gaagtaagtt ggccgcagtg ttatcactca   3300

tggttatggc agcactgcat aattctctta ctgtcatgcc atccgtaaga tgcttttctg   3360

tgactggtga gtactcaacc aagtcattct gagaataccg cgcccggcga ccgagttgct   3420

cttgcccggc gtcaatacgg gataatagtg tatgacatag cagaacttta aaagtgctca   3480

tcattggaaa acgttcttcg gggcgaaaac tctcaaggat cttaccgctg ttgagatcca   3540

gttcgatgta acccactcgt gcacccaact gatcttcagc atcttttact ttcaccagcg   3600

tttctgggtg agcaaaaaca ggaaggcaaa atgccgcaaa aaagggaata agggcgacac   3660

ggaaatgttg aatactcata ctcttccttt ttcaatatta ttgaagcatt tatcagggtt   3720

attgtctcat gagcggatac atatttgaat gtatttagaa aaataaacaa ataggggttc   3780

cgcgcacatt tccccgaaaa gtgccacctg tatgcggtgt gaaataccgc acagatgcgt   3840

aaggagaaaa taccgcatca ggcgaaattg taaacgttaa tattttgtta aaattcgcgt   3900

taaatatttg ttaaatcagc tcatttttta accaataggc cgaaatcggc aaaatccctt   3960

ataaatcaaa agaatagacc gagatagggt tgagtgttgt tccagtttgg aacaagagtc   4020

cactattaaa gaacgtggac tccaacgtca aagggcgaaa aaccgtctat cagggcgatg   4080

gcccactacg tgaaccatca cccaaatcaa gttttttgcg gtcgaggtgc cgtaaagctc   4140

taaatcggaa ccctaaaggg agcccccgat ttagagcttg acggggaaag ccggcgaacg   4200

tggcgagaaa ggaagggaag aaagcgaaag gagcgggcgc tagggcgctg gcaagtgtag   4260

cggtcacgct gcgcgtaacc accacacccg ccgcgcttaa tgcgccgcta cagggcgcgt   4320

ccattcgcca ttcaggctgc gcaactgttg ggaagggcga tcggtgcggg cctcttcgct   4380

attacgccag ctggcgaaag ggggatgtgc tgcaaggcga ttaagttggg taacgccagg   4440

gttttcccag tcacgacgtt gtaaaacgac ggccagtgaa ttgtaatacg actcactata   4500

gggcgaattg ggcc                                                     4514
```

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Primer 001

-continued

<400> SEQUENCE: 5
cgtctagacc atgaaaaagc ctgaactcac cgcgacgtct g 41

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Primer 002

<400> SEQUENCE: 6
catgcggccg ctattccttt gccctcggac gagtgctggg g 41

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Primer 003

<400> SEQUENCE: 7
attgctagca tggcgcaagc cgggagaaca gggtatgata ac 42

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Primer 004

<400> SEQUENCE: 8
cgcacgcgtc acttgtggcc caggtatgca cccagagtg 39

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Primer 005

<400> SEQUENCE: 9
atatgtcgac tcaatattgg ccattagcca tattattcat tg 42

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Primer 006

<400> SEQUENCE: 10
ccggatcgat ccttatcgga ttttaccac 29

<210> SEQ ID NO 11
<211> LENGTH: 55
<212> TYPE: DNA
<213> ORGANISM: Artificial Sequence
<220> FEATURE:
<223> OTHER INFORMATION: Description of Artificial Sequence: Primer 007

<400> SEQUENCE: 11
tcgaccggta cctaggcgcg ccatcgatat cgctagctcg agctcagatc tgtac 55

<210> SEQ ID NO 12

-continued

<211> LENGTH: 47
<212> TYPE: DNA
<213> ORGANISM: Artificial Sequence
<220> FEATURE:
<223> OTHER INFORMATION: Description of Artificial Sequence: Primer 008

<400> SEQUENCE: 12
agatctgagc tcgagctagc gatatcgatg gcgcgcctag gtaccgg 47

<210> SEQ ID NO 13
<211> LENGTH: 78
<212> TYPE: DNA
<213> ORGANISM: Artificial Sequence
<220> FEATURE:
<223> OTHER INFORMATION: Description of Artificial Sequence: Primer 009

<400> SEQUENCE: 13
ctagataact tcgtatagca tacattatac gaagttatac gcgtataact tcgtatagca 60
tacattatac gaagttat 78

<210> SEQ ID NO 14
<211> LENGTH: 78
<212> TYPE: DNA
<213> ORGANISM: Artificial Sequence
<220> FEATURE:
<223> OTHER INFORMATION: Description of Artificial Sequence: Primer 010

<400> SEQUENCE: 14
ctagataact tcgtataatg tatgctatac gaagttatac gcgtataact tcgtataatg 60
tatgctatac gaagttat 78

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Primer 011

<400> SEQUENCE: 15
tcgacgcgtg gaatgtgtgt cagttagggt gtggaaag 38

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Primer 012

<400> SEQUENCE: 16
tcgacgcgtt tggacaaacc acaactagaa tgcagtg 37

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Primer 013

<400> SEQUENCE: 17
tcgacgcgtg aattctaccg ggtaggggag gcgcttttc 39

<210> SEQ ID NO 18
<211> LENGTH: 39
<212> TYPE: DNA
<213> ORGANISM: Artificial Sequence -continued
<220> FEATURE:
<223> OTHER INFORMATION: Description of Artificial Sequence: Primer 014

<400> SEQUENCE: 18
tcgacgcgtg gaattagaac ttggcaaaac aatactgag 39

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Primer 015

<400> SEQUENCE: 19
aatgcggccg cgaacctcct gtgttgcaag cacaaatggg 40

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Primer 016

<400> SEQUENCE: 20
aatgcggccg aggcagcacg gttgagtttc agttgtcatc 40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Primer 017

<400> SEQUENCE: 21
ttggcgcgcc gtaagaatgg cctctccagg tctttatttt 40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Primer 018

<400> SEQUENCE: 22
ttggcgcgcc agctcagctc agctcacccc agctcagctc 40

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Primer 019

<400> SEQUENCE: 23
tatgcggccg cttatctttc tcctttatta acggttgctg 40

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Primer 020

<400> SEQUENCE: 24
tatgcggccg cacagtggta gtactccact gtctggctg 39

-continued

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Primer 021

<400> SEQUENCE: 25
ttggcgcgcc tgtgtaagac acaggttttc atgttaggag 40

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Primer 022

<400> SEQUENCE: 26
ttggcgcgcc tgcttcgcca agtttactgg gtaggttg 38

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: Primer 023

<400> SEQUENCE: 27
tatagcggcc gcttctgctc ctcttcttta gtactggatt c 41

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Primer 024

<400> SEQUENCE: 28
tatagcggcc gcgttggcta agctacctgg gaacaatggg gg 42

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Primer 025

<400> SEQUENCE: 29
ttggcgcgcc ataggatctc cacatagaag ttggtatttg cc 42

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Primer 026

<400> SEQUENCE: 30
ttggcgcgcc gtgggcacac atatgtcatc ccagttaccc 40

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Primer 027

-continued

<400> SEQUENCE: 31
ccatcgattg actggatgct tgttaattct aataag 36

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Primer 028

<400> SEQUENCE: 32
ccatcgatgg atcctgtgtg ccagtaactg tagagagaac 40

<210> SEQ ID NO 33
<211> LENGTH: 44
<212> TYPE: DNA
<213> ORGANISM: Artificial Sequence
<220> FEATURE:
<223> OTHER INFORMATION: Description of Artificial Sequence: Primer 029

<400> SEQUENCE: 33
cgggatccaa gcttagagag gtctggtgga gcctgcaaaa gtcc 44

<210> SEQ ID NO 34
<211> LENGTH: 49
<212> TYPE: DNA
<213> ORGANISM: Artificial Sequence
<220> FEATURE:
<223> OTHER INFORMATION: Description of Artificial Sequence: Primer 030

<400> SEQUENCE: 34
gatcgcggcc gctctagata attgcattca tttaaaaaaa aaatatttc 49

<210> SEQ ID NO 35
<211> LENGTH: 47
<212> TYPE: DNA
<213> ORGANISM: Artificial Sequence
<220> FEATURE:
<223> OTHER INFORMATION: Description of Artificial Sequence: Primer 031

<400> SEQUENCE: 35
gcatgtcgac acgcgtgggg gctcagatat cagtaccaga aacaagg 47

<210> SEQ ID NO 36
<211> LENGTH: 44
<212> TYPE: DNA
<213> ORGANISM: Artificial Sequence
<220> FEATURE:
<223> OTHER INFORMATION: Description of Artificial Sequence: Primer 032

<400> SEQUENCE: 36
cgatgtcgac ctcgagttgg agtcacaggc ctgtctccat gtgg 44

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: Primer 033

<400> SEQUENCE: 37
gcactcgagg ggtagatgca gcctgtgttc cgtttactg 39

<210> SEQ ID NO 38

-continued

<211> LENGTH: 40
<212> TYPE: DNA
<213> ORGANISM: Artificial Sequence
<220> FEATURE:
<223> OTHER INFORMATION: Description of Artificial Sequence: Primer 034

<400> SEQUENCE: 38
gctctcgagc atgcctgagc ccaccaggaa gtcctctgtg 40

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Primer 035

<400> SEQUENCE: 39
ttaagcatgc aaccacatgc gatctaaggg atattgggg 39

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence: Primer 036

<400> SEQUENCE: 40
ttaagcatgc gatcattgag ctccggctct aacaactggg 40

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Primer 037

<400> SEQUENCE: 41
catacgcgtc gctgcatcag gctttcaggg gcccagccc 39

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Primer 038

<400> SEQUENCE: 42
catacgcgtc cctcaccaga aagcagtttc atggataaaa tg 42

<210> SEQ ID NO 43
<211> LENGTH: 41
<212> TYPE: DNA
<213> ORGANISM: Artificial Sequence
<220> FEATURE:
<223> OTHER INFORMATION: Description of Artificial Sequence: Primer 039

<400> SEQUENCE: 43
catacgcgta cagagggaat cacccccaga ggcccaagcc c 41

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Primer 040

<400> SEQUENCE: 44

-continued gacagcgtca gggacaggtg gggacagc 28

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Primer 041

<400> SEQUENCE: 45
gctgtcccca cctgtccctg acgctgtc 28

<210> SEQ ID NO 46
<211> LENGTH: 46
<212> TYPE: DNA
<213> ORGANISM: Artificial Sequence
<220> FEATURE:
<223> OTHER INFORMATION: Description of Artificial Sequence: Primer 042

<400> SEQUENCE: 46
catacgcgtt tatttggaag gggggcgtgt caggtgtgtc agggtc 46

<210> SEQ ID NO 47
<211> LENGTH: 37
<212> TYPE: DNA
<213> ORGANISM: Artificial Sequence
<220> FEATURE:
<223> OTHER INFORMATION: Description of Artificial Sequence: Primer 043

<400> SEQUENCE: 47
atcacgcgtc tcaggcctta gatggggacc cagaccc 37

<210> SEQ ID NO 48
<211> LENGTH: 38
<212> TYPE: DNA
<213> ORGANISM: Artificial Sequence
<220> FEATURE:
<223> OTHER INFORMATION: Description of Artificial Sequence: Primer 044

<400> SEQUENCE: 48
attacgcgtg acccccgtct cctcattcag agtctgtg 38

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: Primer 045

<400> SEQUENCE: 49
catacgcgtc gggacctggg tgcccaccct cagggctgg 39

<210> SEQ ID NO 50
<211> LENGTH: 47
<212> TYPE: DNA
<213> ORGANISM: Artificial Sequence
<220> FEATURE:
<223> OTHER INFORMATION: Description of Artificial Sequence: Primer 046

<400> SEQUENCE: 50
aatacgcgtt tatttgtgcc ctgggctggg tgccgggccc tccttgg 47

<210> SEQ ID NO 51
<211> LENGTH: 37
<212> TYPE: DNA

-continued

<213> ORGANISM: Artificial Sequence
<220> FEATURE:
<223> OTHER INFORMATION: Description of Artificial Sequence: Primer 047

<400> SEQUENCE: 51
gcatgcggcc gccctgggcc cagctctgtc ccacacc 37

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence: Primer 048

<400> SEQUENCE: 52
gcatgcggcc gctgggtgct ttatttccat gctgggtg 38

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: Primer 049

<400> SEQUENCE: 53
tatagcggcc gcagggagtg ggctaaggtg aggcaggtgg 40

<210> SEQ ID NO 54
<211> LENGTH: 42
<212> TYPE: DNA
<213> ORGANISM: Artificial Sequence
<220> FEATURE:
<223> OTHER INFORMATION: Description of Artificial Sequence: Primer 050

<400> SEQUENCE: 54
attagcggcc gcctcagact cggcctgacc cacggaaaga ac 42

<210> SEQ ID NO 55
<211> LENGTH: 42
<212> TYPE: DNA
<213> ORGANISM: Artificial Sequence
<220> FEATURE:
<223> OTHER INFORMATION: Description of Artificial Sequence: Primer 051

<400> SEQUENCE: 55
gcatgcggcc gcccagctct gtcccacacc gcagtcacat gg 42

<210> SEQ ID NO 56
<211> LENGTH: 43
<212> TYPE: DNA
<213> ORGANISM: Artificial Sequence
<220> FEATURE:
<223> OTHER INFORMATION: Description of Artificial Sequence: Primer 052

<400> SEQUENCE: 56
gctagcggcc gctcgcaggg gcccagggca gcgctgggtg ctt 43

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: Primer 053

<400> SEQUENCE: 57
attagcggcc gcggatagac aagaaccgag gggcctctg 39

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Primer 054

<400> SEQUENCE: 58
taatgcggcc gcccagggca gtggtgggtg ctttatttcc 40

<210> SEQ ID NO 59
<211> LENGTH: 40
<212> TYPE: DNA
<213> ORGANISM: Artificial Sequence
<220> FEATURE:
<223> OTHER INFORMATION: Description of Artificial Sequence: Primer 055

<400> SEQUENCE: 59
attagcggcc gccaccccag taggccagag catcgtgcac 40

<210> SEQ ID NO 60
<211> LENGTH: 39
<212> TYPE: DNA
<213> ORGANISM: Artificial Sequence
<220> FEATURE:
<223> OTHER INFORMATION: Description of Artificial Sequence: Primer 056

<400> SEQUENCE: 60
taatgcggcc gccacccctg atagccatga cagtctggg 39

<210> SEQ ID NO 61
<211> LENGTH: 41
<212> TYPE: DNA
<213> ORGANISM: Artificial Sequence
<220> FEATURE:
<223> OTHER INFORMATION: Description of Artificial Sequence: Primer 057

<400> SEQUENCE: 61
attagcggcc gctgtcacca ggcctctctg tgctgggttc c 41

<210> SEQ ID NO 62
<211> LENGTH: 39
<212> TYPE: DNA
<213> ORGANISM: Artificial Sequence
<220> FEATURE:
<223> OTHER INFORMATION: Description of Artificial Sequence: Primer 058

<400> SEQUENCE: 62
tattgcggcc gccggatgga agcgtggggc tgcttgggg 39

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Primer059

<400> SEQUENCE: 63
taatgcggcc gccacggggt ccccagctcc cccatccagg 40

<210> SEQ ID NO 64
<211> LENGTH: 38
<212> TYPE: DNA
<213> ORGANISM: Artificial Sequence
<220> FEATURE:

-continued

<223> OTHER INFORMATION: Description of Artificial Sequence: Primer 060

<400> SEQUENCE: 64
atatgcggcc gctcccaaga atgggtgtac tggggctc 38

<210> SEQ ID NO 65
<211> LENGTH: 35
<212> TYPE: DNA
<213> ORGANISM: Artificial Sequence
<220> FEATURE:
<223> OTHER INFORMATION: Description of Artificial Sequence: Primer 061

<400> SEQUENCE: 65
ccatcgatcc tggtctacag tgtgaggtac tggac 35

<210> SEQ ID NO 66
<211> LENGTH: 47
<212> TYPE: DNA
<213> ORGANISM: Artificial Sequence
<220> FEATURE:
<223> OTHER INFORMATION: Description of Artificial Sequence: Primer 062

<400> SEQUENCE: 66
ccatcgatgg atcctctgag agctggaaga gaggatgctt tattagg 47

<210> SEQ ID NO 67
<211> LENGTH: 48
<212> TYPE: DNA
<213> ORGANISM: Artificial Sequence
<220> FEATURE:
<223> OTHER INFORMATION: Description of Artificial Sequence: Primer 063

<400> SEQUENCE: 67
cgggatcctg acgcgtacca gggagaagac tgatttatta gagatttc 48

<210> SEQ ID NO 68
<211> LENGTH: 39
<212> TYPE: DNA
<213> ORGANISM: Artificial Sequence
<220> FEATURE:
<223> OTHER INFORMATION: Description of Artificial Sequence: Primer 064

<400> SEQUENCE: 68
gatgcggccg caaagattca ctttatttat tcattctcc 39

<210> SEQ ID NO 69
<211> LENGTH: 45
<212> TYPE: DNA
<213> ORGANISM: Artificial Sequence
<220> FEATURE:
<223> OTHER INFORMATION: Description of Artificial Sequence: Primer 065

<400> SEQUENCE: 69
cgggatccaa gcttgaaaaa tgtttaactc agctactata atccc 45

<210> SEQ ID NO 70
<211> LENGTH: 44
<212> TYPE: DNA
<213> ORGANISM: Artificial Sequence
<220> FEATURE:
<223> OTHER INFORMATION: Description of Artificial Sequence: Primer 066

<400> SEQUENCE: 70
gttttgttgg agctcccctt tgaagatatt ctcaggcttc cttc 44

-continued

<210> SEQ ID NO 71
<211> LENGTH: 49
<212> TYPE: DNA
<213> ORGANISM: Artificial Sequence
<220> FEATURE:
<223> OTHER INFORMATION: Description of Artificial Sequence: Primer 067

<400> SEQUENCE: 71
aatatcttca aaggggagct ccaacaaaac aatttagaac tttattaag 49

<210> SEQ ID NO 72
<211> LENGTH: 39
<212> TYPE: DNA
<213> ORGANISM: Artificial Sequence
<220> FEATURE:
<223> OTHER INFORMATION: Description of Artificial Sequence: Primer 068

<400> SEQUENCE: 72
acgcgtcgac tagaacgtgt ctgggcccca tgaaacatc 39

<210> SEQ ID NO 73
<211> LENGTH: 42
<212> TYPE: DNA
<213> ORGANISM: Artificial Sequence
<220> FEATURE:
<223> OTHER INFORMATION: Description of Artificial Sequence: Primer 069

<400> SEQUENCE: 73
cgatgtcgac agctcaaacc agcttaggct acacagagaa ac 42

<210> SEQ ID NO 74
<211> LENGTH: 37
<212> TYPE: DNA
<213> ORGANISM: Artificial Sequence
<220> FEATURE:
<223> OTHER INFORMATION: Description of Artificial Sequence: Primer 070

<400> SEQUENCE: 74
ccatcgatct gtggaatgtg tgtcagttag ggtgtgg 37

<210> SEQ ID NO 75
<211> LENGTH: 51
<212> TYPE: DNA
<213> ORGANISM: Artificial Sequence
<220> FEATURE:
<223> OTHER INFORMATION: Description of Artificial Sequence: Primer 071

<400> SEQUENCE: 75
tcaggggatg gtggcggccc taggcctcca aaaaagcctc ctcactactt c 51

<210> SEQ ID NO 76
<211> LENGTH: 51
<212> TYPE: DNA
<213> ORGANISM: Artificial Sequence
<220> FEATURE:
<223> OTHER INFORMATION: Description of Artificial Sequence: Primer 072

<400> SEQUENCE: 76 ctttttgga ggcctagggc cgccaccatc ccctgaccca cgcccctgac c 51

<210> SEQ ID NO 77
<211> LENGTH: 35
<212> TYPE: DNA
<213> ORGANISM: Artificial Sequence
<220> FEATURE:
<223> OTHER INFORMATION: Description of Artificial Sequence: Primer 073

-continued

<400> SEQUENCE: 77
ccatcgatcc agacatgata agatacattg atgag 35

<210> SEQ ID NO 78
<211> LENGTH: 37
<212> TYPE: DNA
<213> ORGANISM: Artificial Sequence
<220> FEATURE:
<223> OTHER INFORMATION: Description of Artificial Sequence: Primer 074

<400> SEQUENCE: 78
ccatcgatct gtggaatgtg tgtcagttag ggtgtgg 37

<210> SEQ ID NO 79
<211> LENGTH: 47
<212> TYPE: DNA
<213> ORGANISM: Artificial Sequence
<220> FEATURE:
<223> OTHER INFORMATION: Description of Artificial Sequence: Primer 075

<400> SEQUENCE: 79
gatgtcacgt gagatcccag acatgataag atacattgat gagtttg 47

<210> SEQ ID NO 80
<211> LENGTH: 45
<212> TYPE: DNA
<213> ORGANISM: Artificial Sequence
<220> FEATURE:
<223> OTHER INFORMATION: Description of Artificial Sequence: Primer 076

<400> SEQUENCE: 80
tcttatcatg tctgggatct cacgtgacat cttataataa acctg 45

<210> SEQ ID NO 81
<211> LENGTH: 45
<212> TYPE: DNA
<213> ORGANISM: Artificial Sequence
<220> FEATURE:
<223> OTHER INFORMATION: Description of Artificial Sequence: Primer 077

<400> SEQUENCE: 81
ccatcgatac gcgtaattca caaaccaagt ctattatttt caata 45

<210> SEQ ID NO 82
<211> LENGTH: 40
<212> TYPE: DNA
<213> ORGANISM: Artificial Sequence
<220> FEATURE:
<223> OTHER INFORMATION: Description of Artificial Sequence: Primer 078

<400> SEQUENCE: 82
catgcggccg cgagtatccc tgtgcagtgg ggatactcag 40

<210> SEQ ID NO 83
<211> LENGTH: 48
<212> TYPE: DNA
<213> ORGANISM: Artificial Sequence
<220> FEATURE:
<223> OTHER INFORMATION: Description of Artificial Sequence: Primer 079

<400> SEQUENCE: 83
tctcaggaga gactcgagac tcctttgtgc tctgatagca cacatgac 48

<210> SEQ ID NO 84
<211> LENGTH: 47

-continued

<212> TYPE: DNA
<213> ORGANISM: Artificial Sequence
<220> FEATURE:
<223> OTHER INFORMATION: Description of Artificial Sequence: Primer 080

<400> SEQUENCE: 84
gcacaaagga gtctcgagtc tctcctgaga tggttcatag gcctgcc 47

<210> SEQ ID NO 85
<211> LENGTH: 38
<212> TYPE: DNA
<213> ORGANISM: Artificial Sequence
<220> FEATURE:
<223> OTHER INFORMATION: Description of Artificial Sequence: Primer 081

<400> SEQUENCE: 85
gggaattctc tagacataag gaacaaagtc agtgtgcc 38

<210> SEQ ID NO 86
<211> LENGTH: 41
<212> TYPE: DNA
<213> ORGANISM: Artificial Sequence
<220> FEATURE:
<223> OTHER INFORMATION: Description of Artificial Sequence: Primer 082

<400> SEQUENCE: 86
ccacgcgtaa aagcttgtct aggtggagcc cactccttgc c 41

<210> SEQ ID NO 87
<211> LENGTH: 39
<212> TYPE: DNA
<213> ORGANISM: Artificial Sequence
<220> FEATURE:
<223> OTHER INFORMATION: Description of Artificial Sequence: Primer 083

<400> SEQUENCE: 87
catgcggccg ccctgtaccc cacactgaga accccgggg 39

<210> SEQ ID NO 88
<211> LENGTH: 35
<212> TYPE: DNA
<213> ORGANISM: Artificial Sequence
<220> FEATURE:
<223> OTHER INFORMATION: Description of Artificial Sequence: Primer 084

<400> SEQUENCE: 88
gcggatccat ggactggacc tggaggrtcy tctkc 35

<210> SEQ ID NO 89
<211> LENGTH: 35
<212> TYPE: DNA
<213> ORGANISM: Artificial Sequence
<220> FEATURE:
<223> OTHER INFORMATION: Description of Artificial Sequence: Primer 085

<400> SEQUENCE: 89
gcggatccat ggagyttggg ctgasctggs ttcyt 35

<210> SEQ ID NO 90
<211> LENGTH: 35
<212> TYPE: DNA
<213> ORGANISM: Artificial Sequence
<220> FEATURE:
<223> OTHER INFORMATION: Description of Artificial Sequence: Primer 086

<400> SEQUENCE: 90

-continued gcggatccat ggammwactk tgkwbcwysc tyctg 35

<210> SEQ ID NO 91
<211> LENGTH: 35
<212> TYPE: DNA
<213> ORGANISM: Artificial Sequence
<220> FEATURE:
<223> OTHER INFORMATION: Description of Artificial Sequence: Primer 087

<400> SEQUENCE: 91
gcggatccat ggacatgrrr dycchvgykc asctt 35

<210> SEQ ID NO 92
<211> LENGTH: 34
<212> TYPE: DNA
<213> ORGANISM: Artificial Sequence
<220> FEATURE:
<223> OTHER INFORMATION: Description of Artificial Sequence: Primer 088

<400> SEQUENCE: 92
gcacgcgtat grcctgswcy cctctcytyc tyws 34

<210> SEQ ID NO 93
<211> LENGTH: 40
<212> TYPE: DNA
<213> ORGANISM: Artificial Sequence
<220> FEATURE:
<223> OTHER INFORMATION: Description of Artificial Sequence: Primer 089

<400> SEQUENCE: 93
tataagctta cctgaggaga cggtgaccag ggtgccctgg 40

<210> SEQ ID NO 94
<211> LENGTH: 40
<212> TYPE: DNA
<213> ORGANISM: Artificial Sequence
<220> FEATURE:
<223> OTHER INFORMATION: Description of Artificial Sequence: Primer 090

<400> SEQUENCE: 94
tataagctta cctgaggaga cggtgaccak kgtsccwykg 40

<210> SEQ ID NO 95
<211> LENGTH: 39
<212> TYPE: DNA
<213> ORGANISM: Artificial Sequence
<220> FEATURE:
<223> OTHER INFORMATION: Description of Artificial Sequence: Primer 091

<400> SEQUENCE: 95
tataagctta cgtttgatct ccasyttggt ccctbggcc 39

<210> SEQ ID NO 96
<211> LENGTH: 39
<212> TYPE: DNA
<213> ORGANISM: Artificial Sequence
<220> FEATURE:
<223> OTHER INFORMATION: Description of Artificial Sequence: Primer 092

<400> SEQUENCE: 96
tataagctta cgtttaatct ccagtcgtgt cccttggcc 39

<210> SEQ ID NO 97
<211> LENGTH: 39
<212> TYPE: DNA
<213> ORGANISM: Artificial Sequence -continued
<220> FEATURE:
<223> OTHER INFORMATION: Description of Artificial Sequence: Primer 093

<400> SEQUENCE: 97
tataagctta cctaggacgg tcagcttggt cccwsckcc 39

<210> SEQ ID NO 98
<211> LENGTH: 39
<212> TYPE: DNA
<213> ORGANISM: Artificial Sequence
<220> FEATURE:
<223> OTHER INFORMATION: Description of Artificial Sequence: Primer 094

<400> SEQUENCE: 98
tataagctta ccgagggcgg tcagctgggt gcctcctcc 39

METHOD FOR THE GENERATION OF GENETICALLY MODIFIED VERTEBRATE PRECURSOR LYMPHOCYTES AND USE THEREOF FOR THE PRODUCTION OF HETEROLOGOUS BINDING PROTEINS

This is a National Phase Application in the United States of International Patent Application No. PCT/EP01/15303 filed Dec. 22, 2001, the entire disclosure of which is incorporated herein by reference.

FIELD OF THE INVENTION

The present invention generally relates to the fields of genetic engineering and antibody production. In particular, it relates to the generation of genetically modified vertebrate precursor lymphocytes that have the potential to differentiate into more mature lymphoid lineage cells, and to the use thereof for the production of any heterologous antibody or binding protein.

BACKGROUND OF THE INVENTION

Monoclonal antibodies have been proven to be effective reagents for both diagnosis, prevention and therapy of disease (Glennie and Johnson, *Immunol. Today,* 21, p. 403-410, 2000). This is due to their unique capacity to bind very specifically to particular epitopes on target molecules (antigens) via their variable domains and, at the same time, to mediate effector functions via their constant region domains (Frazer and Capra, *Fundamental Immunology*, W. E. Paul (Ed.), *Fourth Edition*, p. 37-74, 1999) (FIG. 1). This enables monoclonal antibodies to specifically identify unique antigens in complex mixtures of macromolecules and to direct effector functions to these targets.

Antibodies (or immunoglobulins) consist of two identical heavy (H) chain and light (L) chain glycoproteins that are linked via disulphide bonds (FIG. 1). Each H and L chain comprises an N-terminal variable domain that varies between different antibodies and a C-terminal constant region, that is identical in different antibodies belonging to the same immunoglobulin isotype (FIG. 1). The combination of H and L chain variable domains generates the antigen binding pocket of the antibody and determines its specificity (or idiotype), whereas the constant regions determine its isotype (Frazer and Capra, s.a.). The variability of immunoglobulins results from the fact that $V_H$ and $V_L$ domains are encoded by a multitude of gene segments, that are designated V (variable), D (diversity; only present in the H chain locus), and J (joining) gene segments (Tonegawa, *Nature,* 302, p. 575-581, 1983) (FIG. 1). During the differentiation of B lymphocytes one V, D and J gene segment is randomly selected in each cell for the site-specific recombination process of V(D)J recombination, that assembles the gene segments, such that new coding regions for $V_H$ or $V_L$ domains are generated (Grawunder et al., *Curr. Opin. Immunol.,* 10, p. 172-180, 1998). Due to the multitude of V, D, and J gene segments, and imprecision in gene segment joining, an enormous repertoire of different V region specificities can be generated by the millions of B lymphocytes produced by the immune system every day (Melchers et al., *Curr. Opin. Immunol.,* 7, p. 214-227, 1995).

During evolution, immunoglobulin genes have slightly diverged between different species, such that the constant regions of antibodies differ between species. As a consequence, immunoglobulins from one species are most often immunogenic, if introduced into the vascular system of another species.

The immunogenicity of xenogeneic monoclonal antibodies therefore limits their use in the therapy of human disease, because exposure of patients to xenogeneic antibodies may result in adverse effects, even acute toxicity, or might simply lead to the neutralization and clearance of the applied antibody, thereby reducing its pharmacological efficacy (Clark, *Immunol Today,* 21, p. 397-402, 2000) In contrast, administration of fully human antibodies to patients usually does not lead to any of the aforementioned complications.

Human antisera or human polyclonal antibodies have occasionally been isolated from the blood of individual patients for the treatment or prevention of rare and usually highly lethal diseases, like Ebola virus infections, or e.g. for the treatment of individuals after exposure to snake venoms. However, this approach, for many reasons, is impractical for the treatment of diseases affecting larger populations. Furthermore, for ethical reasons, it is impossible to immunize humans with a given antigen for the purpose of monoclonal antibody production, because the B-lineage cells in humans producing the desired antibodies develop and reside in secondary lymphoid organs and cannot easily be obtained. Furthermore, many potential target antigens for therapeutic antibodies, in particular for cancer therapy, are human proteins (Glennie and Johnson, s.a.). Under normal circumstances, humans will not develop antibodies against these targets. Therefore, substantial efforts have been made in the recent past to develop procedures for the development of therapeutic human or humanized antibodies without the need of the human immune system.

The simplest approach uses standard genetic engineering techniques for cloning of cDNAs encoding the variable domains of H and L chains ($V_H$ and $V_L$ domains) from a hybridoma secreting a xenogeneic antibody of desired specificity. The cloned variable region cDNAs are then cloned into appropriate *E. coli*, yeast, insect or mammalian cell expression vectors containing human constant region genes. This will allow the production of monoclonal antibodies with the xenogeneic $V_H$ and $V_L$ domains fused to the human $C_H$ and $C_L$ constant region domains, thereby resulting in a humanized antibody. However, this approach has the disadvantage that the fusion of xenogeneic $V_H$ and $V_L$ domains to human $C_H$ and $C_L$ constant regions may result in either decreased affinity or altered specificity. In addition, the heterologous $V_H$ and $V_L$ of the humanized antibody are still immunogenic in humans, because framework regions of V domains vary between different species. This problem can in some cases be circumvented by grafting individual complementarity determining regions (CDRs), which mediate the direct contact to antigens, onto human framework regions of H and L chain variable domains (Fiorentini et al., *Immunotechnology,* 3, p. 45-59, 1997). However, for unknown reasons, CDR grafting still often results in the generation of immunogenetic antibodies and/or the decrease/loss of affinity and specificity.

Therefore, two different and more effective approaches have been developed in recent years for the generation of completely human immunoglobulins.

The first method is based on the expression (display) of single chain variable regions (scFv) consisting of one $V_H$ and $V_L$ domain on the surface of filamentous bacteriophages of *E. coli* (Hoogenboom and Chames, *Immunol. Today,* 21, p. 371-3818, 2000) (cf. also EP 0 585 287 B1, EP 0 605 522 B1). Phage display libraries containing a diverse repertoire of $V_H$ and $V_L$ chain can be constructed, and individual scFv specificities can be isolated from such libraries by binding of recombinant phages to immobilized antigen (McCafferty et al., *Nature,* 348, p. 552-554, 1990).

Phage display libraries for scFv binding proteins derived from a natural human repertoire have the drawback of being restricted to specificities contained in that repertoire, and specificities for many human antigens are therefore most often not represented in these libraries. Although combinatorial or synthetic phage display libraries may be used to circumvent this problem, a general drawback of this technology is that high affinity binding proteins for a given antigen can often not be isolated. Therefore, substantial efforts have been invested in constructing very large primary libraries by either brute force cloning or site specific recombination procedures. The The best combinatorial or synthetic libraries are estimated to contain $10^9$-$10^{11}$ potentially different binding sites and can yield binding specificities in the 1-200 nM range (Hoogenboom and Chames, s.a.). However, higher affinities in the picomolar range ($10^{-12}$ M), that can be reached during affinity maturation of immunoglobulins in germinal center B cells in vivo, can only be generated employing additional tedious genetic engineering procedures, including V gene shuffling, error-prone PCR, the use of *E. coli* mutator strains etc.

Whatever the outcome of a phage display library selection process is, eventually the genes encoding the scFv binding site need to be recloned into suitable expression vectors for human immunoglobulins, and these need to be stably transferred into a cellular expression system allowing the large-scale production of human antibodies, which is another time-consuming and expensive procedure.

The second approach for the production of fully human monoclonal antibodies is based on the use of transgenic mice harbouring constructs for the human immunoglobulin H and L chain gene loci (Jakobovits, *Curr. Opin. Biotechnol.,* 6, p. 561-566, 1995). The human immunoglobulin transgenes are eventually bred onto a genetic background that does no longer allow assembly of the endogenous murine antigen receptor genes. In these mice, development of B-lineage cells depends on the expression of immunoglobulin H and L chains from the human transgenic constructs, and B lineage cells of these mice are only capable of producing human antibodies. There are three variations of this technique. In one, human immunoglobulin miniloci are used as transgenes, from which only a limited repertoire of human antibodies can be generated (Fishwild et al., *Nat. Biotechnol.,* 14, p. 845-851, 1996) (also cf. to, EP 0 546 073 B1, U.S. Pat. No. 5,874,299, WO 92/03918). In a second variation, large regions of the human IgH and IgκL chain gene loci encompassing the majority of the variable region gene segments cloned into yeast artificial chromosomes are used. In a third variation, pieces of human chromosomes containing the entire human immunoglobulin H and L chain gene loci are integrated into the germline of mice generating so-called trans-chromosomic animals. Mice with such complex transgenes develop a practically normal human immunoglobulin repertoire.

Immunization of these transgenic or trans-chromosomic mice results in a humoral immune response resulting in the generation of fully human antibodies. This approach of generating human antibodies has one important advantage over the phage display library technology: High affinity antibodies for a given antigen can be generated, because the human immunoglobulins can undergo affinity maturation in germinal center B cells, which is a normal process in the course of an immune reaction.

However, there is one important drawback of this technology: First, the generation of transgenic or trans-chromosomic mice is very tedious, difficult, time-consuming, and therefore relatively expensive. For example, WO 92/03918 discloses B cells of a transgenic mouse expressing human monoclonal antibodies. In order to achieve this transgenic mouse, fertilized eggs are transfected with exogenous elements by introducing the heterologous IgH and IgL chain transgenes by pronuclear injection. The entire procedure requires the generation of at least four different mouse strains: two strains with targeted disruptions within the endogenous IgH and IgL chain gene loci, as well as two strains carrying transgenes or trans-chromosomes for part or all of the human IgH and IgL chain gene loci. In addition, all these four mouse strains have to be bred together, resulting in mice with a genotype carrying homozygous disruptions of both the endogenous IgH and IgL chain gene loci and at the same time carrying the human transgenes encoding both the heterologous IgH and IgL chains. Generation of the different knock-out and transgenic mouse strains, their screening and eventual crossbreeding is a lengthy procedure that will require at least two years, even if each step is completely optimized. The extensive time-frames required for the development of a xenomouse strain therefore leaves little flexibility for designing different mouse strains containing modified transgenic constructs. Therefore, this technology is not suitable for the modification and improvement of existing antibodies (e.g. of their affinity), because this would require the lengthy procedure of generating a novel transgenic mouse strain for this one antibody. This technology is therefore basically restricted to the de novo generation of human antibodies.

Based on the aforementioned facts, there is clearly the need for a technology allowing the production of fully human antibodies that would combine the advantages of both the phage display system (i.e. speed and flexibility in generating human antibodies, and the ability to modify and improve the properties of existing antibodies), and of the human immunoglobulin transgenic mouse technology (i.e. the ability to obtain high affinity antibodies due to affinity maturation occurring in the immune system, and production of antibodies with physiologic and natural structural features).

SUMMARY OF THE INVENTION

The present invention provides means and methods to generate vertebrate precursor lymphocytes that can be used for the production of any binding protein or functional fragment(s) thereof with the ability to selectively bind to an antigen or ligand, including any heterologous antibody, antigen receptor composed of variable domains and constant regions comprising T cell receptors and membrane bound immunoglobulins, any artificial binding protein displaying either wild-type immune effector functions or modified or artificial effector functions not derivable from germline encoded heterologous immunoglobulins or antigen receptors, and any functional fragment(s) thereof. In particular, the invention provides means and methods to genetically modify vertebrate precursor lymphocytes and to effect their differentiation into more mature lymphoid lineage cells either in vitro or in vivo, thereby generating lymphocytes capable of producing said binding protein or functional fragment(s) thereof, as well as a method for the production of said binding protein or functional fragment(s) thereof. Furthermore, the present invention provides genetically modified vertebrate precursor lymphocytes and mature lymphoid lineage cells as well as immortalized cells derived therefrom suitable for carrying out the methods according to the invention.

Thus, the methods of the present invention allow a great deal of flexibility for the generation of lymphoid lineage cells with the potential to express simply any type of antibody or binding protein, within short periods of time. At the same time, the possibility to transplant these cells into compatible vertebrate hosts, where the cells participate in specific immune functions such as affinity maturation, allows the exploitation of the selectivity of the immune system for generating antibodies and immunoglobulin-like or even artificial binding proteins of high binding affinities for any given antigenic compound or composition.

DESCRIPTION OF THE DRAWINGS

FIG. 3) can be sequentially transduced with retroviral expression vectors encoding IgL chains and IgH chains, as indicated. After successive transduction with first heterologous IgL and then IgH chain expressing retroviral constructs, the cells have the potential to express heterologous antibodies upon differentiation of the cells either in vitro, or in vivo (see FIG. 10).

FIG. 9) and may be inserted into the retroviral vectors as V region exons encoding a single specifity, or as libraries encoding different specificities (which need to be PCR amplified with degenerate primer pairs). V regions are PCR amplified together with their characteristic leader (L) sequences, as indicated. Restriction enzymes that can be used for the cloning of variable region exons are indicated. This drawing depicts some selected final retroviral IgH and IgL chain expression vectors. Due to the modular design of these vectors, different coding regions and promoter and enhancer elements may be used.

DEFINITION OF TERMS USED THROUGHOUT THE SPECIFICATION

Figure 1:
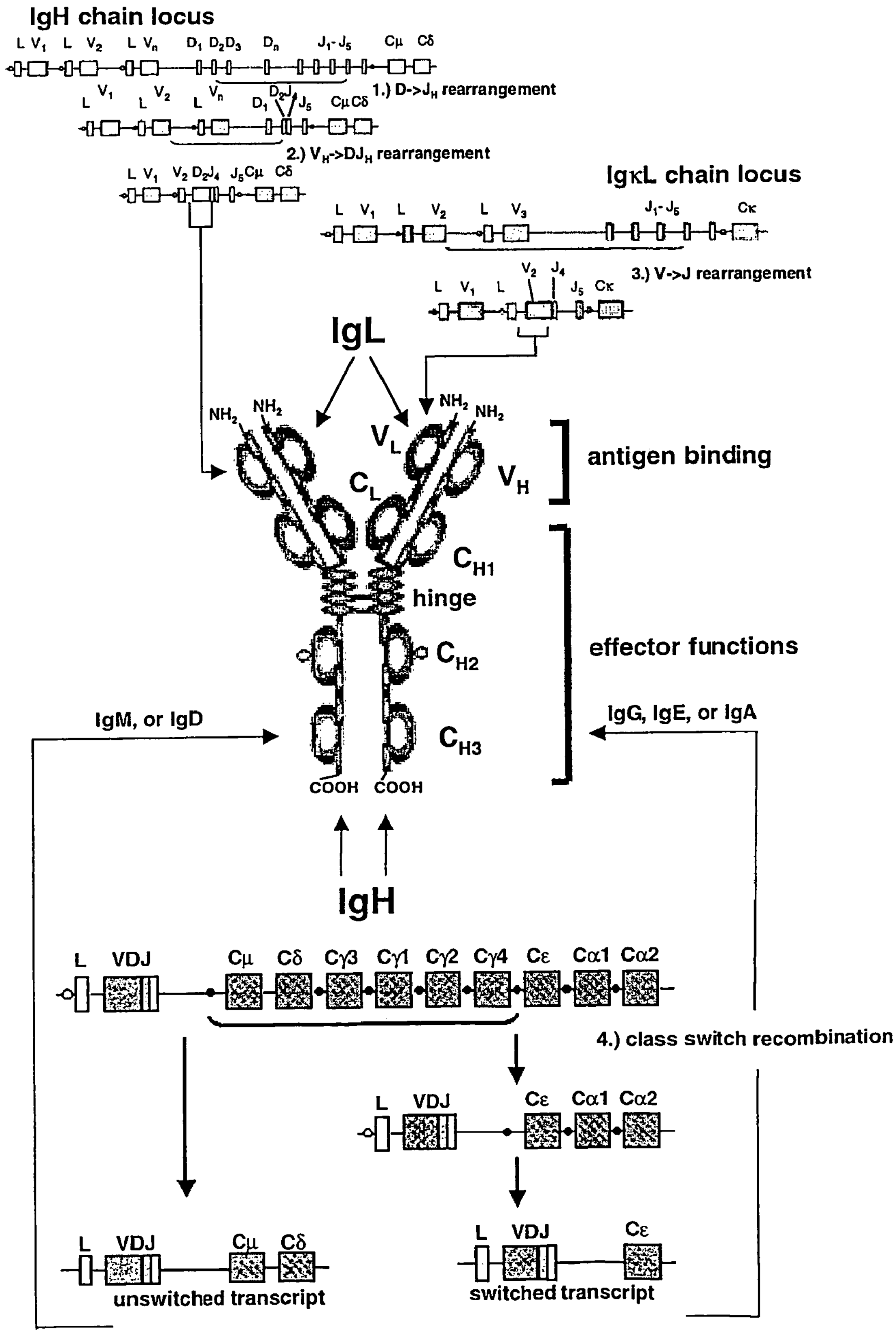
FIG. 1 is a schematic representation of immunoglobulin structure and genetics. Antibodies or immunoglobulins (Ig) are glycoproteins that in their monomeric form are composed of two identical heavy chains (IgH) and two identical light chains (IgL) that are covalently linked by disulfide bonds. Each IgH chain comprises one N-terminal variable domain ($V_H$) and 3-4 constant region domains ($C_H$1-3, or 4), depending on the antibody isotype. In addition, antibodies contain a hinge region between the first and the second $C_H$ domain, lending flexibility to the two antigen binding arms of the heterotetrameric glycoprotein. Light chains consist of only one N-terminal variable ($V_L$) and one C-terminal constant domain ($C_L$). The arrangement of the two IgH and IgL chains results in a Y shaped monomeric antibody with two highly variable binding sites for antigen, which are formed by the association of the IgH and IgL chain variable domains. Variable domains differ to a great extent in so-called hypervariable regions, if V-regions are compared between different antibodies. This variability results from the fact that V regions are not encoded by single genes, but, in the case of $V_H$ regions, by a number of different V, D and J gene segments, from which one each is randomly selected and then recombined to form the variable coding region of IgH chains (see upper left part of the drawing). This process is called V(D)J recombination and occurs during early B cell development. The IgL chain gene loci contain only a number of different V and J gene segments, from which coding regions for variable domains are generated by a random V to J rearrangement (see upper right part of the drawing). The constant region domains of antibodies from the same subclass (isotype) determine the effector functions of the antibody, and do not differ between different antibodies. However, in the course of an immune response, individual B lymphocytes can be induced to change the isotype of the antibody that is expressed. In this case, a somatic DNA recombination event occurs between switch regions (indicated by a dot in the graphic representation of the constant region genes in the lower part of the drawing) located 5' of the different constant region genes. For instance, recombination between the μ- and ϵ-switch regions can result in the deletion of all constant region genes from Cμ to Cγ4, as indicated in the drawing. As a result from this, a VDJ variable coding region is brought into proximity to a Cϵ constant region, leading to the expression of an antibody of IgE isotype.

Affinity: The strength of the binding of an antigen receptor (or of any receptor) for its cognate antigen (or its ligand or binding partner), determined by the ratio of association to dissociation rate of the receptor-ligand interaction.

Affinity maturation: A highly regulated immunological process of antigen driven improvement of the binding specificities of antibodies produced by antigen stimulated B lymphocytes in germinal centers. The process is caused by somatic hypermutation within the coding regions for the variable domains of antibodies coupled with the selective expansion and survival of B lymphocytes generating higher affinity antibodies.

Antibody: A glycosylated polypeptide produced by B lymphocytes and plasma cells comprising in its monomeric form two identical heavy (H) chains and two identical light chains, each being composed of one variable domain and one (L chains) or several (H chains) constant region domains. The two H and two L chains assemble into a symmetric Y shaped disulphide linked antibody molecule that has two binding domains formed by the combination of the variable regions of H and L chains.

Antigen: Any biomolecule or chemical entity that can be bound by the variable domains of immunoglobulins (or antibodies).

Antigen receptor: Antigen receptors are composed of variable domains and constant regions, the former having the ability to bind to antigens, and the latter to mediate effector functions or to transduce signals into cells. Antigen receptors comprise T cell receptors and membrane bound immunoglobulins.

Artificial binding protein: A binding protein containing polypeptide sequences (e.g. synthetic spacer sequences) not derivable from natural genes or fragments thereof.

Binding protein: The most general term for any type of polypeptide with the ability to selectively bind to an antigen or ligand, with or without additional effector functions. Binding proteins include artificial binding proteins, fragments of antibodies, like e.g. a single chain variable fragment (scFv), and also fusion products combining variable and constant region domains of immunoglobulins and T cell receptors, or vice versa. Furthermore, a binding protein can be the fusion product of variable domains with functional parts of other receptor molecules. Conversly, a binding protein can be the fusion of a binding moiety from a non-Ig or TCR related receptor with constant region domains of antigen receptors.

Cis-acting: Having an influence only on genetic elements and gene loci in vicinity or on the same allele.

Coding region: A genetic element that has an open reading frame that can be expressed into a polypeptide.

Complementary determining regions (CDRs): The regions in the three dimensional structure of a variable antigen receptor domain that directly establish contact to antigens. The CDRs are usually the most diverse parts of antigen receptors.

Domain: A structural moiety of a biomolecule that is characterized by a particular three dimensional structure (e.g. variable or constant region domains of immunoglobulins, that are structurally related, such as Ig-like domains that can be found in many molecules of the immune system, which belong to the so-called Ig-superfamily).

Effector functions: Functions of constant regions of immunoglobulins in the context of the immune system, e.g. the ability to activate complement, or to activate certain immune cells by binding to specific receptors for constant region (Fc receptors).

Endogenous: Being self to a certain cell or organism.

Enhancer: A genetic element that can stimulate the activity of promoter elements over large distances, independent of orientation or position.

Epitope: A three dimensional structural entity of an antigen that is recognized by a variable binding region of an antibody.

Functional fragment (of an antibody, antigen receptor or binding protein). A functional fragment derivable from a given polypeptide selected from the group consisting of antibodies, antigen receptors and binding proteins, that shares at least one of the desired properties inherent to said polypeptide with respect to the specific field of application. For example, a functional fragment may be a polypeptide or oligopeptide maintaining the capability of said polypeptide to bind to certain antigens and/or ligands. The same applies to fragments mediating specific effector functions characteristic for said polypeptide. A further example relates to fragments being able to activate or inhibit specific immunogenic and/or physiologic effector functions of antibodies, antigen receptors and regular receptor-ligand systems.

Genetic elements: Genes, gene loci, or fragments thereof, like promoters, enhancers, and coding regions, alone or in any functional or non-functional combination.

Germinal center: A distinct histological structure in peripheral lymphoid organs (e.g. lymph nodes or spleen) where cognate interactions between antigen presenting cells and different lymphocyte populations occur, resulting in the proliferative expansion of antigen reactive lymphocytes, as well as affinity maturation and class switch recombination of antibodies produced by antigen reactive B lymphocytes.

Germline configuration: The native configuration of genes and gene loci, as they are inherited from the parents, and as they will be passed on to further generations through the germline. DNA recombination events occuring in somatic cells, like e.g. V(D)J recombination in lymphocytes, lead to the reshuffling or loss of genetic information on certain gene loci and therefore to a change of the genes from the germline configuration.

Heterologous: Being different from endogenous.

Humanized antibody: An artificial antibody generated by fusing the variable domains of non-human antibodies to human constant region domains.

Hybridoma: An immortal cell line that has been generated by the fusion of an immortal myeloma cell line (unable to secrete antibody) and a mortal plasma cell (that may secrete large amounts of antibodies).

Idiotype: The binding characteristic (specificity) of an antigen receptor.

Isotype: The structural characteristic conferred to by the constant region of an antigen receptor determining their (effector) functions.

Immunoglobulin (Ig): Synonymous for antibody.

Immunoglobulin minilocus: An artificial genetic construct comprising few (i.e. single digit) V, D and/or J gene segments, capable of undergoing V(D)J recombination, thereby generating a limited, oligoclonal repertoire of variable coding regions.

Library: A collection of different genetic elements.

Monoclonal antibody: Antibody with one defined specificity determined by the unique structure of the variable antigen binding region of the antibody.

Myeloma cell: An immortal cell derived from a cell at plasma cell differentiation stage without the ability to express endogenous immunoglobulin proteins.

Polyclonal antibodies: A mixture of antibodies having different structures of the variable antigen binding regions, and therefore, most likely, different binding specificities.

PreB lymphocyte: A precursor B lymphocyte is characterized by the expression of lymphoid specific factors involved in V(D)J recombination (e.g. RAG-1, RAG-2), usually has initiated V(D)J recombination on at least one immunoglobulin heavy chain allele, but still carries the light chain gene loci in germline configuration, and therefore does not express complete antibodies.

Primary lymphoid organs: Organs, in which lymphocytes develop from hematopoietic stem cells, in mice and humans e.g. the bone marrow, the thymus, and during fetal life, the liver.

Repertoire: A collection of different (binding) specificities.

Somatic hypermutation: A process in somatic cells resulting in the introduction of point mutations into specific regions of the genome at a high frequency ($>10^{-4}$ mutations per basepair per cell division).

Stromal cells: Proliferating adherent cells derived from the bone marrow with the capacity to support proliferation of preB cells in the presence of additional preB cell growth factor(s).

Trans-acting: Having an influence on genetic elements and gene loci located on different chromosomes.

Transfecting: The process of introducing nucleic acid sequences into eukaryotic cells, usually associated with using chemical and physical methods.

Transforming: The process of immortalizing a cell for the establishment of a continuously proliferating cell line.

Transgene: An artificial genetic element introduced into the germline of animals. The transgene is therefore inherited from one generation to the other.

Transducing: The process of delivering DNA into mammalian cells via the production of recombinant viruses. For this, a packaging cell line, expressing structural proteins for viral particles is transfected with a recombinant viral DNA construct comprising the regulatory elements for packaging of the viral DNA construct into the viral structural proteins. By this, recombinant viruses are produced that can be used to infect mammalian target cells leading to the introduction of the genetic information cloned into the recombinant viral genome.

V(D)J recombination: A DNA recombination process during which one of many V(variable), sometimes D (diversity), and J (joining) gene segments are assembled to a coding region for the variable domains of antigen receptors.

Vector: An artificially generated nucleic acid construct which can be used to shuttle nucleic acid elements between different organisms and species, and which can further be used to propagate, amplify and maintain genomic information.

Xenogeneic: Being derived from a different species (often used synonymous to heterologous).

All references cited throughout the specification are incorporated herewith.

DETAILED DESCRIPTION OF THE INVENTION

According to a first aspect, the present invention provides a method for the generation of vertebrate lymphocytes that can be used for the production of any binding protein or functional fragment(s) thereof with the ability to selectively bind to an antigen or ligand, including any heterologous antibody, any antigen receptor composed of variable domains and constant regions comprising T cell receptors and membrane bound immunoglobulins, any artificial binding protein displaying either wild-type immune effector functions or modified or artificial effector functions not derivable from germline encoded heterologous immunoglobulins or antigen receptors, and any functional fragment(s) thereof, comprising the steps of:

(a) genetically modifying vertebrate precursor lymphocytes, which
  (i) are derived from primary lymphoid organs, and
  (ii) have the potential to differentiate into mature lymphoid lineage cells, by introducing at least one exogenous genetic element encoding at least one binding protein or functional fragment thereof; and
(b) effecting differentiation of said genetically modified precursor lymphocytes into mature lymphoid lineage cells either in vitro or in vivo, thereby generating lymphocytes capable of producing said binding protein or functional fragment(s) thereof, under the proviso that the in vivo production in humans is excluded.

In order to achieve large scale production of the above binding proteins or functional fragments thereof, it is preferred that the terminally differentiated lymphocytes producing the polypeptides of interest are immortalized, or, alternatively, that the genetic information coding for the heterologous antibodies or binding proteins are isolated and transferred from these cells into different expression systems, where said genetic information can be maintained, amplified and/or used for the production of the respective immunoglobulins or immunoglobulin-like proteins or functional fragments thereof.

The immortalization of said lymphocytes can preferably be achieved by:

(a) fusing the same to immortal myloma cells for the generation of hybridoma cells;
(b) infecting the same with transforming viruses, like e.g. Abelson murine leukemia virus (A-MuLV); or
(c) transfecting the same with an appropriate vector construct ensuring the expression of at least one transforming oncogene, like e.g. v-abl, or the SV40 large T antigen, that upon overexpression leads to the immortalization of stably transfected cells;

thereby generating vertebrate lymphocytes capable of permanently producing said binding protein or functional fragment(s) thereof.

In a preferred embodiment, the vertebrate precursor lymphocytes are able to express at least one component of the lymphoid V(D)J recombination machinery and originate from jawed vertebrates comprising cartilaginous fish, bony fish, amphibians, reptilia, birds, mammals including pigs, sheep, cattle, horses and rodents including mice, rats, rabbits and guinea pigs, with murine precursor (pre) B lymphocytes from mice being preferred.

Primary precursor B lymphocytes in all jawed vertebrate species from human down to the evolutionarily most primitive cartilaginous fish are not only characterized by the expression of a specific set of cell surface markers (like the combination of B220 and c-kit in mice), but also by their potential to assemble the gene segments encoding the variable domains of antibodies for which they express the lymphoid specific components of the V(D)J recombination machinery, like RAG-1, RAG-2, and TdT (terminal deoxynucleotidyl transferase). Although some species, like birds, have different primary lymphoid organs (e.g. the bursa of *Fabricius*) where these precursor B lymphocytes are generated, and despite the fact that in addition to V(D)J recombination, other species also use different mechanisms for antibody diversification, like somatic hypermutation (e.g. sheep), or gene conversion (e.g. rabbits), precursor B lymphocytes from all vertebrate species are capable of undergoing V(D)J recombination and have the potential to differentiate into more mature B lineage cells, such that antibodies generated from VDJ rearranged immunoglobulin gene loci can be expressed. Therefore, if such vertebrate precursor B lymphocytes are isolated or generated that are incapable of expressing endogenous antibodies, and if genetic elements encoding all or parts of heterologous immunoglobulin gene loci are stably introduced into these lymphocytes, they will gain the potential to produce heterologous antibodies and are thus encompassed by the present invention.

The method according to the invention makes use of vertebrate precursor B (preB) lymphocytes present in primary lymphoid organs. In the case of mice, these cells can be isolated from fetal liver or adult bone marrow, e.g. by preparative cell sorting using and c-kit on mouse preB cells; alternatively, they can be selectively outgrown from murine fetal liver or bone marrow cell suspensions due to their strong proliferative response to both bone marrow derived feeder (stromal) cells, and growth factors such as interleukin-7 and interleukin-3.

In terms of expression of lymphoid components of the V(D)J recombination machinery, the potential to differentiate to mature lymphoid lineage cells and the genetic mechanism for the diversification of antigen receptor proteins, T lineage lymphocytes are very similar to B lineage lymphocytes. It is therefore to be understood that the methods described herein for the genetic modification of precursor B lymphocytes for the purpose of producing heterologous antibodies or binding proteins can likewise be applied to precursor T lymphocytes. Therefore, the present methods primarily described with respect to the system of murine preB lymphocytes, can also be applied to all vertebrate precursor lymphocytes from all jawed vertebrates as set forth before. It is to be understood, that the use of any other precursor lymphocyte system for carrying out the principles of the present invention solely depends on the feasability to both prevent expression of endogenous antibodies and to introduce heterologous genetic elements into these cells encoding heterologous antibodies or binding proteins. Since the broad applicability of these principles will be appreciated by those skilled in the art, the general concept underlying the present invention is primarily described with respect to the use of murine precursor B (preB) lymphocytes.

Figure 2:
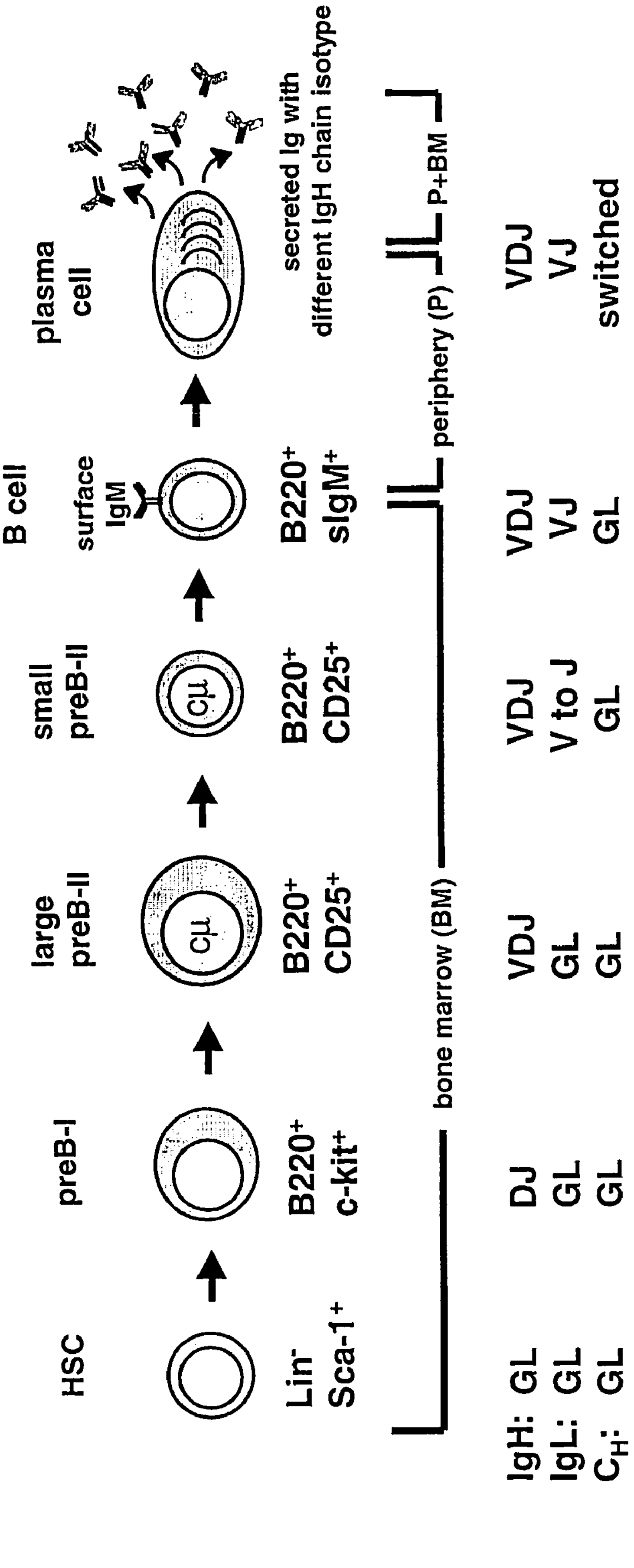
FIG. 2 illustrates B cell development in the mouse. The differentiation of B lymphocytes in the mouse can be subdivided into distinct stages that can phenotypically and genotypically be subdivided. The earliest committed precursor B (preB) cells that can be found in the bone marrow of wildtype mice are derived from a pluripotent hematopoietic stem cell (HSC, left), that does not express lineage specific markers (which is designated as $Lin^-$), but is characterized by the surface expression of stem cell antigen 1 (Sca-1). From this, preB cells are generated that usually carry $DJ_H$ rearrangements on both IgH chain alleles and that are characterized by surface expression of B220 (a pan-B cell marker) and c-kit. At this stage all other Ig gene loci are usually still in germline (GL) configuration. $DJ_H$ rearranged preB cells are designated preB-I cells and can be expanded in tissue culture under specific conditions. The next rearrangement event in these cells involves one of the $V_H$ gene segments that rearranges to a pre-existing $DJ_H$ element. If this leads to a productive rearrangement on any allele such that a μpH chain can be expressed, these cells receive a proliferative signal, expand and differentiate into preB-II cells. These cells loose expression of the c-kit surface marker, but gain expression of CD25. A further productive rearrangement on any of the IgL chain alleles results in the differentiation to immature B cells expressing membrane bound IgM. These immature, naïve B cells can leave the bone marrow, migrate into peripheral lymphoid organs, where they might eventually encounter antigen. In the course of an immune response, these B cells can then differentiate into antibody secreting plasma cells, during which another DNA recombination process (class switch recombination) may occur in the IgH constant region locus resulting in the change of antibody isotype that is secreted by the plasma cells.
Figure 3:
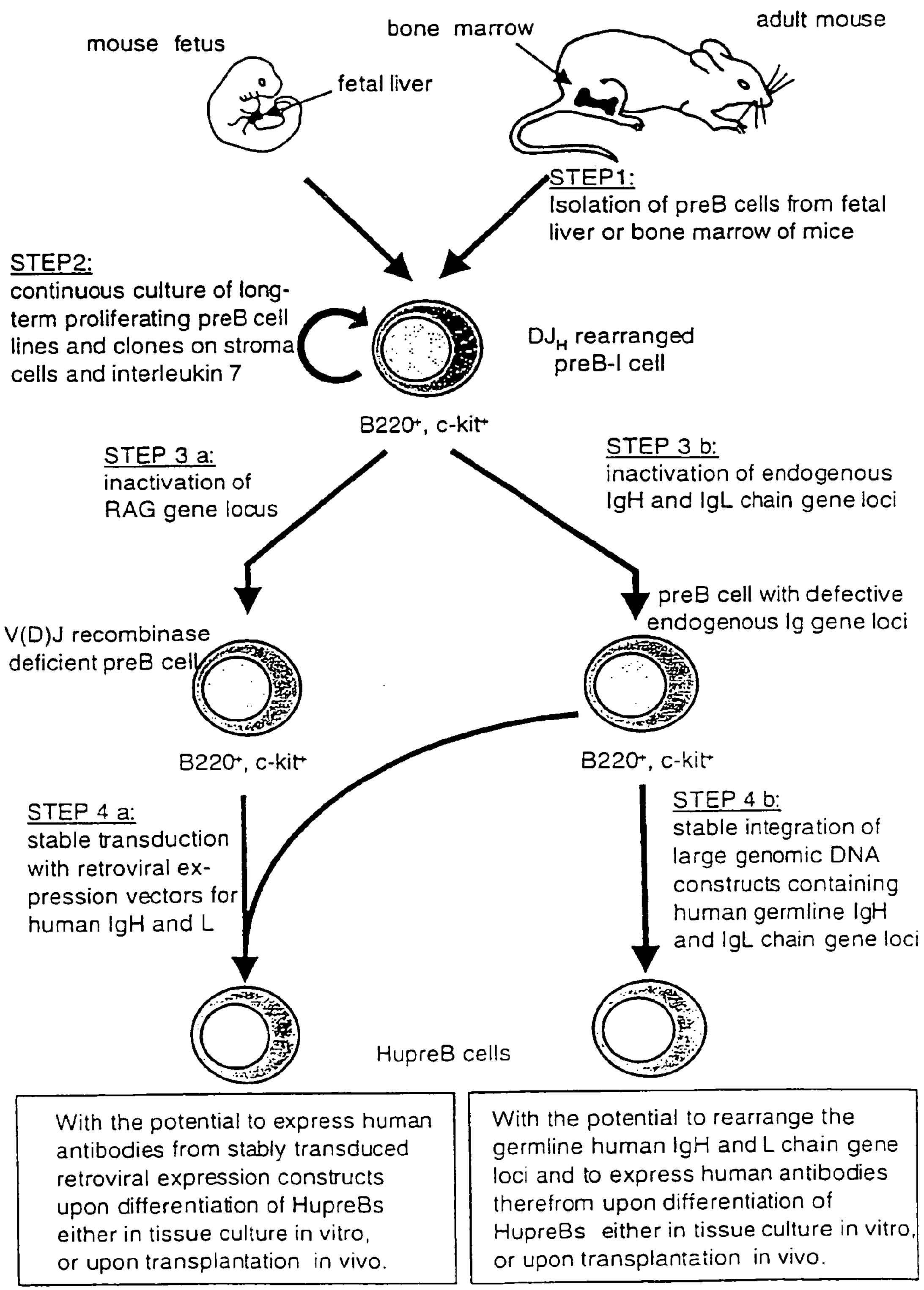
FIG. 3 is a schematic overview of the method according to the invention for the generation of humanized precursor B lymphocytes (HupreB's). Murine $DJ_H$ rearranged preB-I cells can be isolated from fetal liver of mice 14-19 days post coitum, or from the bone marrow of adult mice (Step 1). The long-term culture of these cells requires special tissue culture conditions, including stromal cell feeder layers and/or the presence of certain growth factors, such as e.g. IL-7 (interleukin 7). Under these conditions, preB-I cells do not differentiate further (Step 2). In order to use these cells for the production of heterologous antibodies, it must be prevented that further productive endogenous Ig gene rearrangements can be performed in these cells. This can e.g. be accomplished by introducing cis-acting mutation(s) on both alleles of the IgH and IgL chain gene loci (Step 3b), or, alternatively, by introducing trans-acting mutation(s) that ablate further V(D)J recombination of Ig genes, e.g. by deleting one of the two recombination activating genes, RAG-1 or RAG-2 (Step 3a). The latter cells can then be stably transduced with recombinant retroviruses capable of mediating expression of xenogeneic, in this case human, IgH and IgL chains (Step 4a). These retroviral vectors can also be used for the stable transduction of the former cells carrying cis-acting mutations in endogeneous Ig gene loci. In addition, preB cells carrying cis-acting mutations are still competent for Ig gene rearrangements. It is therefore possible to stably transfect these cells with heterologous germline Ig gene loci, which may undergo V(D)J rearrangements, and from which novel xenogeneic antibodies can be produced (Step 4b). If the heterologous or xenogeneic IgH and IgL chain genes are from human origin, the preB-I cells will only have the potential for the expression of fully human antibodies, and are therefore referred to as HupreB cells.

In the mouse, the development from hematopoietic stem cells to antibody secreting plasma cells is a highly regulated process and, in vivo, depends on the ordered rearrangement of gene segments in the immunoglobulin receptor gene loci and the regulated expression of immunoglobulin proteins from productively rearranged Ig gene loci (FIG. 2). Usually, rearrangements occur first on both alleles of the IgH chain gene loci, with D to $J_H$ gene segments rearranging first, followed by $V_H$ to $DJ_H$ gene rearrangements (FIG. 2). If a productive $V_HDJ_H$ rearrangements has occured on one allele, μH chain can be expressed on the cell surface as a preB cell receptor pairing with surrogate L chain (encoded by the preB cell specific genes $\lambda_5$ and $V_{preB}$) (Karasuyama et al., *Adv. Immunol.,* 63, 1-41, 1996). The expression of a preB cell receptor allows the differentiation of preB cells to a stage, at which $V_L$ to $J_L$ rearrangements are initiated, which usually occurs first on the κL chain alleles and later on the λL chain alleles (Melchers et al., *Ann. Rev. Immunol.,* 12, p. 209-225, 1994). If a productive IgL chain rearrangement has occurred, membrane bound IgM and/or IgD antibodies can be expressed by so-called immature B cells. Stimulation of peripheral, IgM/IgD positive, mature B cells with appropriate signals can lead to class switch recombination on the IgH chain alleles that changes the isotype of the expressed antibodies to any of the IgG, IgA, IgE subtypes (in mice: IgG1, IgG2a, IgG2b, IgG3, IgA, IgE, in humans: IgG1, IgG2, IgG3, IgG4, IgA1, IgA2, IgE) (FIG. 1).

As already outlined before, the murine preB cells suitable for carrying out the invention are characterized by the expression of B220 and c-kit surface markers, the expression of at least one of the lymphoid V(D)J recombination genes RAG-1 and RAG-2, and the ability to proliferate for longer periods of time in responsiveness of stromal cells and/or IL7 or IL3 (Rolink et al., *EMBO J.,* 10, p. 327-336, 1991; Winkler et al., *Blood,* 85, p. 2045-2051, 1995). If preB cell lines and clones are established from wild-type mice, they usually carry $DJ_H$ rearrangements on both IgH chain alleles (Alt et al., *EMBO J.,* 3, p. 1209-1219, 1984), or in some cases non-productive $V_HDJ_H$ rearrangements (FIG. 2). However, rearrangements of their IgH chain alleles are not required to establish stromal cell, IL7 or IL3 responsive cells from mice with a preB cell phenotype, as these cells can also be established from mutant mouse strains, that are deficient in V(D)J recombination (Grawunder et al., *International Immunology,* 7, p. 1915-25, 1995). In any circumstance, irrespective of the potential for Ig gene rearrangements preB cells retain the potential to differentiate into more mature B lineage cells in vitro, and eventually into isotype-switched plasma cells (Rolink et al., *Immunity,* 5, p. 319-330, 1996).

Long term proliferating murine preB cell lines and clones can be established from various lymphoid organs of mice, including fetal liver, fetal blood, fetal spleen, and adult bone marrow, but also other fetal or adult organs that harbour stromal cell, IL7 or IL3 responsive preB cells, especially early in life (<4 weeks of age) (Rolink et al., *Blood,* 81, p. 2290-2300, 1993).

Mice used for the generation of the above mentioned preB cells can be wild-type mice, chimaeric mice, transplanted mice or mouse strains carrying mutations impeding V(D)J recombination on the endogenous murine Ig gene loci. The above mentioned mutations may be in cis, including deletions of, or within the IgH diversity (D) gene segments, the IgH J gene segments (Chen et al., *Int. Immunol.,* 5, p. 647-656, 1993), the μH chain constant region, including the two exons for the μH transmembrane anchor (Kitamura and Rajewsky, *Nature,* 356, p. 154-156, 1992), the Igκ and Igλ J gene segments, the κL chain constant region ($C_\kappa$) (Chen et al., *EMBO J.,* 12, p. 821-830, 1993), the λL chain constant regions ($C_\lambda$1-4) and the various IgH and L chain enhancers, including the heavy chain intron enhancer (EμH), the κ intron enhancer (κiE), the 3' κ enhancer (3'κE), and the two λ enhancers (Eλ2-4 and Eλ3-1).

According to the invention, preB cells carrying any of the above mentioned cis-acting mutations can be used for the introduction of exogenous genetic elements comprising part or all of heterologous, especially human immunoglobulin gene loci in non-rearranged, i.e. germline configuration. Such genetically modified preB cells can be used for the de novo production of antibody specificities, because the novel specificities are only generated upon V(D)J recombination on the heterologous genetic immunoglobulin gene loci.

Alternatively, suitable preB cells can also be generated from mice incapable of rearranging endogenous immunoglobulin gene loci due to trans-acting mutations, like e.g. in the lymphoid specific recombination activating genes RAG-1 and RAG-2 (Mombaerts et al., *Cell,* 68, p. 869-877, 1992; Shinkai et al., *Cell,* 68, p. 855-867, 1992), or in the ubiquitously expressed DNA repair factors Ku70, Ku86, XRCC4, DNA ligase IV, Artemis or the catalytic subunit of the DNA dependent protein kinase (DNA-PKcs), which are involved in the non-homologous DNA end joining, and that are also required for V(D)J recombination. For the production of heterologous antibodies and binding proteins in preB cells carrying such trans-acting mutations, expression constructs are to be used that do not require the DNA rearrangements of V, (D) and J gene segments (see below).

In the case of cis-acting mutations in the mouse, these preferably need to minimally include (a) homozygous mutation(s) in the immunoglobulin heavy and the immunoglobulin κL chain gene loci. In the case of trans-acting mutations, one of the above mentioned homozygous mutations in a given preB cell line is sufficient to preclude the expression of endogenous immunoglobulins being a fundamental requirement of the method according to the invention.

Precursor B lymphocytes carrying cis- or trans-acting genetic modifications interfering with the expression of endogenous immunoglobulins can be isolated from mice carrying either naturally (e.g. scid mice) or artificially generated mutations. Alternatively, preB lymphocytes from wildtype mice can be screened for mutations on their immunoglobulin alleles precluding the expression of endogenous antibodies, e.g. terminally out-of-frame $DJ_H$ rearrangements on both heavy chain alleles. Mutations ablating the expression of endogenous murine antibodies, can be introduced into hematopoietic stem cells or into early progenitor cells, from which suitable long-term proliferating preB cells can be generated either upon differentiation in vitro or in vivo.

Alternatively, the genetic effects referred to hereinbefore can also be directly introduced into at least one allele of the precursor lymphocytes to be subjected to genetic modification. The inactivation of one allele can be sufficiant for carrying out the present invention, since mutated clones can be isolated, which already carry certain mutations on the other allele (heterozygous mutations), such that a homozygously mutated gene locus is established within the precursor lymphocyte cells to be used according to the invention.

Although it is to be understood that the invention can be realized with wild-type precursor lymphocytes, it is preferred in the method according to the invention, that said vertebrate precursor lymphocytes are deprived of their potential to express endogenous antibodies and/or antigen receptors or functional fragment(s) thereof, which is achieved by isolating/selecting vertebrate precursor lymphocytes being deficient in expressing endogenous immunoglobulins or fragments thereof, and/or by introducing into said vertebrate precursor lymphocytes at least one vector construct designed to functionally inactivate at least one allele of at least one genetic element, which is selected from the group consisting of:

(a) the coding regions of the immunoglobulin heavy chain gene locus, including all or parts of the V, D, and J gene segments, and any of the coding regions for the constant region exons for μ, δ, γ, ϵ, and α heavy chains, with or without their membrane spanning exons;

(b) the coding regions of the immunoglobulin κ and/or λ light chain gene loci, including any of the V and J gene segment coding regions, as well as any of the constant region exons;

(c) the coding regions of the T cell receptor α, β, γ, and δ gene loci, including all or parts of the V, D and J gene segments, and any of the coding regions for the α, β, γ, and δ constant region exons;

(d) the cis-acting immunoglobulin heavy chain gene locus enhancer elements, including the heavy chain intron enhancer and the 3' α enhancer;

(e) the cis-acting immunoglobulin light chain gene locus enhancer elements, including the κ light chain intron enhancer (κiE), the 3'κ enhancer, and the λ2-4 and λ3-1 enhancers;

(f) the cis-acting T cell receptor gene loci enhancer elements, including the TCR α, β, γ, and δ enhancers;

(g) the trans-acting recombination activating genes, RAG-1 and RAG-2, including their promoter and enhancer elements, as well as their coding regions; and (h) the trans-acting DNA repair genes essential for V(D)J recombination, including Ku70, Ku86, the catalytic subunit of DNA-dependent protein kinase (DNA-PKcs), DNA ligase IV, XRCC4 and Artemis, including their promoter and enhancer elements, as well as the coding regions of said genes.

Figure 4:
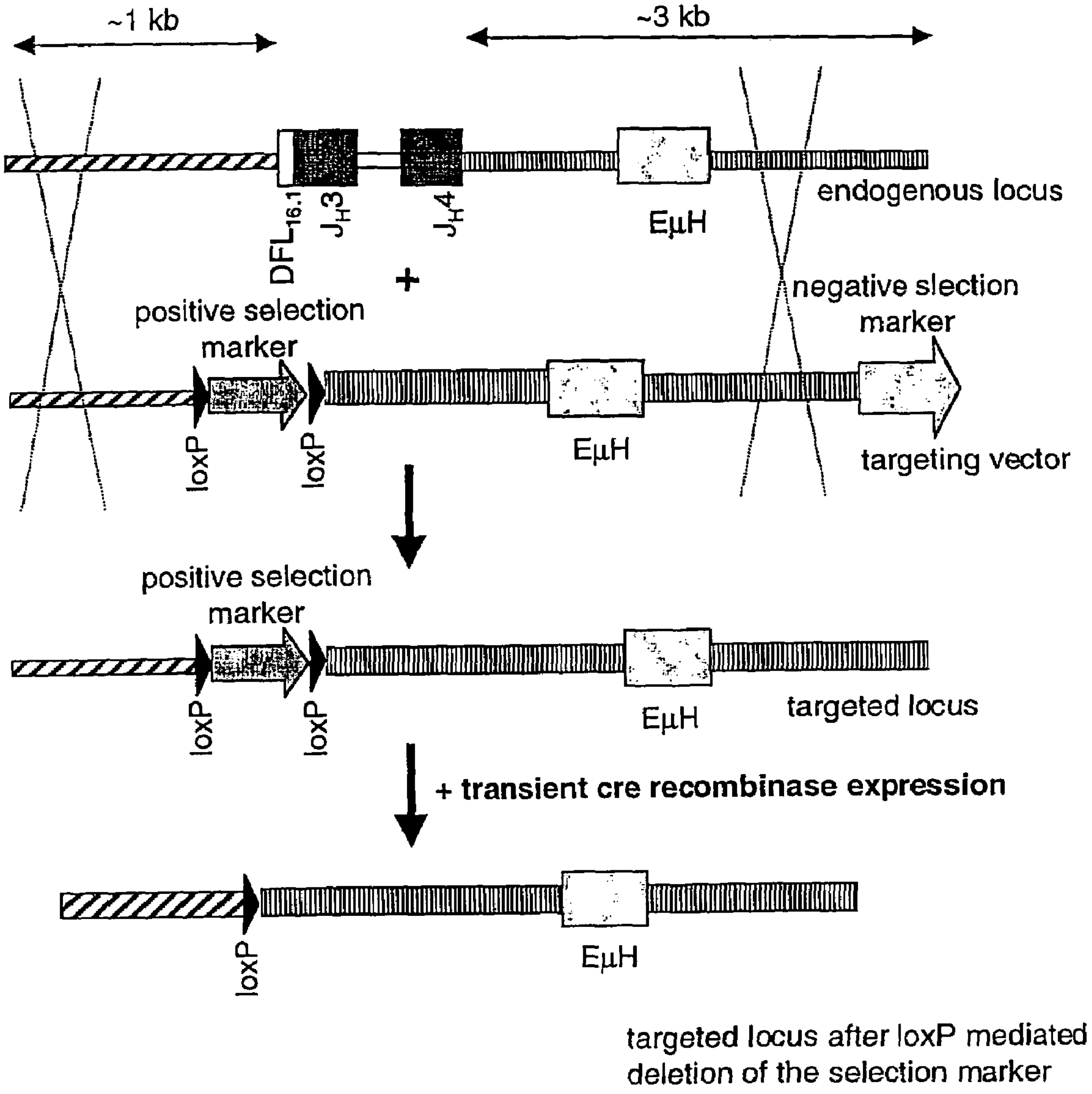
FIG. 4 is a schematic representation illustrating the targeting of endogenous gene loci using positive-negative gene targeting vectors. For the targeting of endogenous gene loci, a genomic region of approximately 1 kb upstream (short arm) of that locus and a region of approximately 3 kb (long arm) downstream of that gene is cloned into an empty positive-negative targeting vector. As an example, the targeting strategy for a $DJ_H3$ rearranged IgH chain locus is depicted. This construct is transfected into preB-I cells and integration of the targeting vector by homologous recombination is selected and eventually screened for. The positive selection marker allows selection for the stable integration of the construct into the genome of the transfected cell. The expression of the negative selection marker would be toxic for the cell, and cells will only survive, if the negative selection marker is lost upon stable integration, which occurs by two homologous recombination events at the correct locus. Two possible sites for homologous recombination between the endogenous gene locus and the targeting construct are indicated by hatched lines. If integration of the construct by such homologous recombination events occurs, the positive drug selection marker replaces the endogenous region located in between the short and long arms of homology. If the positive selection marker is flanked by two loxP recombination signals, as indicated here, transient expression of cre recombinase can mediate the deletion of the selection marker, such that the same targeting construct can be used for targeting of the second allele of the same gene locus.

Preferably, the above vector constructs include gene targeting vectors comprising regions of DNA sequence homology to said at least one genetic element, preferably flanking a positive selection marker enabling selection of positive transfectants. For example, suitable targeting vectors contain two regions of high sequence homology (>99%), or sequence identity to the targeted gene locus, preferably flanking a positive selection marker (such as an antibiotic resistance marker), such that a double cross-over event in each of the sequence homology regions results in targeted integration of the positive selection marker and thus in the targeted disruption of an endogenous gene (FIG. 4*a-c*). Positive selection markers employed in these targeting vectors may include expression cassettes conferring resistance to antibiotics like puromycin, hygromycin B, neomycin (G418), histidinol, mycophenolic acid, zeocin and the like.

Figure 6A:
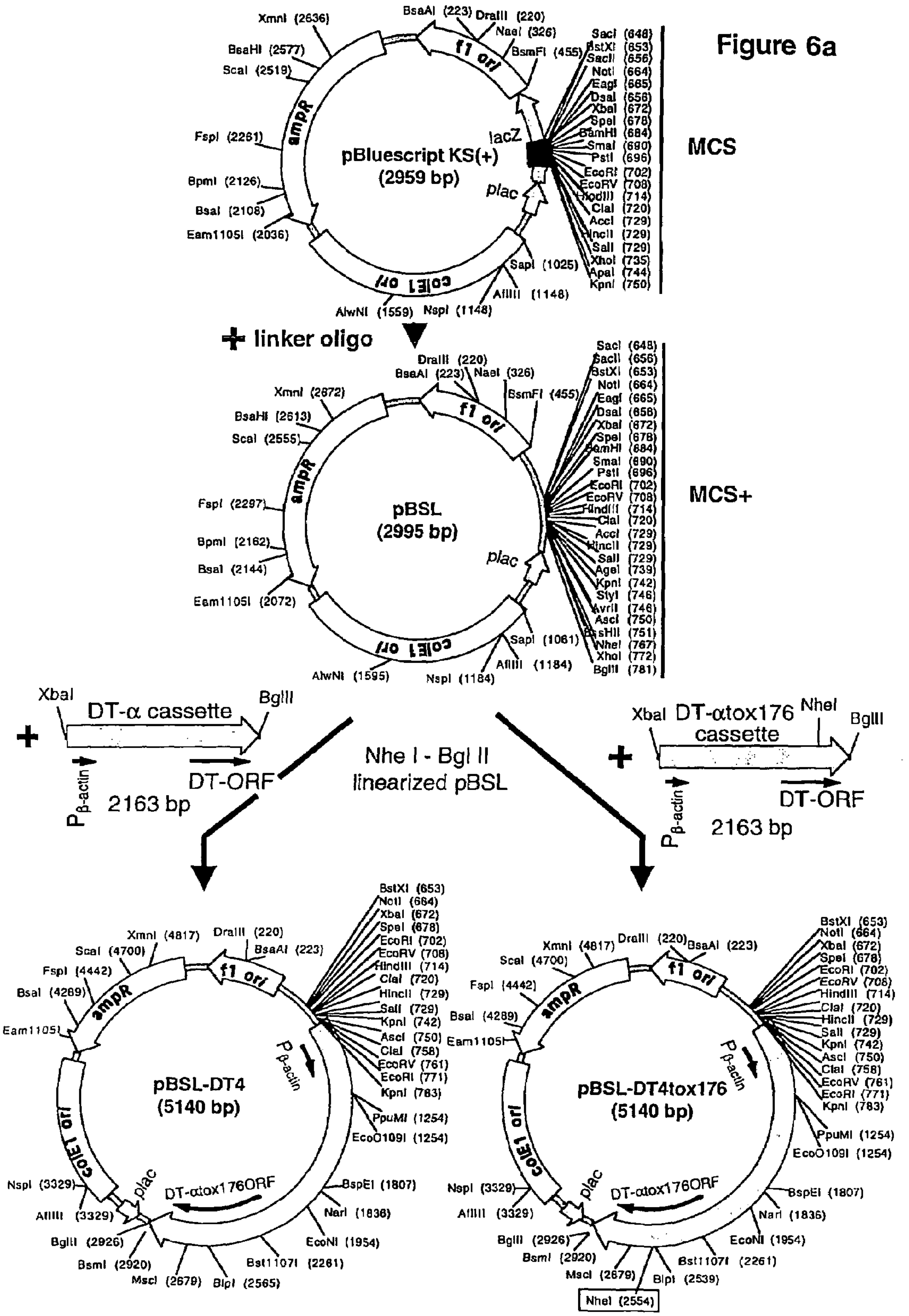
FIG. 6*a* shows the detailed cloning strategy for DT-α and DT-α(tox176) based positive-negative vectors for gene targeting (preparatory steps). A prerequisite for the generation of empty targeting vectors is to extend the multiple cloning site (MCS) of a regular cloning plasmid, like pBluescript, such that additional useful restriction sites are added to the polylinker, which can then be used for the insertion of expression cassettes for positive and negative selection markers, as well as for genomic regions required for the targeting of an endogenous gene locus by homologous recombination. Depicted here is the insertion of an additional oligomer with additional restriction sites into the MCS of pBluescript, thereby generating plasmid pBSL with an extended polylinker. This construct is used to insert a β-actin promoter driven expression cassette for either wild-type diphtheria toxin α or an attenuated version thereof, denoted DTα (tox176) (cf. example 5b, step 2). These two constructs with extended multiple cloning site are designated pBSL-DT4 (bottom, left) and pBSL-DT4tox176 (bottom, right), respectively. The diphtheria toxin expression cassettes are cloned into pBSL using XbaI and BglII restriction sites, as indicated. A diagnostic NheI restriction site that is unique for the attenuated DTtox176 expression cassette is indicated as well.

It is preferred, that said gene targeting vectors additionally comprise a pair of DNA recognition sequences for site-specific DNA recombination enzymes, flanking the positive selection marker, enabling deletion of said positive selection marker upon transfection and transient expression of nucleic acid sequences encoding at least one of the cognate recombinase enzymes. For example, the positive selection marker may be flanked by loxP or FLP sequences recognized by the cre-recombinase or FLP recombinase enzymes, respectively (Kühn and Schwenk, *Curr. Opin. Immunol.,* 9, p. 183-188, 1997), allowing the site-specific removal of the selection marker expression cassette from the genome of gene targeted preB cells by transient transfection of cre- or flp-recombinase expression vectors (FIGS. 6*a, b*). This procedure allows the repeated use of targeting vectors using the same positive selection marker.

In a prefered embodiment, said gene targeting plasmid vectors additionally comprise a negative selection marker enabling selection against transfectants in which said gene targeting vectors are randomly integrated into the genome by non-homologous recombination. For example, suitable negative selection markers selecting against random integration of targeting constructs, may include expression cassettes for the herpes simplex virus thymidine kinase gene (HSV-TK), for the diphtheria toxin gene (DT) (McCarrick et al., *Transgenic Res.,* 2, p. 183-190, 1993), or for its attenuated version DTtox176 (Maxwell et al., *Mol. Cell. Biol.,* 7, p. 1576-1579, 1987). These negative selection markers are positioned in the targeting constructs, such that a targeted integration of the positive/negative targeting construct results in the removal of the negative selection marker (FIGS. 6*a,b*). Thus, only integration of the targeting vector by homologous recombination will allow survival of the cells, and—as a consequence—selection for targeting and disruption of part of endogenous gene loci by homologous recombination.

It is to be understood, that the use of vertebrate precursor lymphocytes deprived of their potential to express endogenous antibodies and/or antigen receptors or functional fragment (s) thereof is preferred. However, vertebrate precursor lymphocytes with the potential to express antibodies and/or antigen receptors or functional fragment(s) thereof can likewise be used according to the invention. Regardless of the actual genetic background of the precursor lymphocytes, these cells have to be subjected to genetic modification in order to allow production of heterologous antibodies or binding proteins. It is to be understood, that said modification will preferably be performed after appropriate target cells or clones have been identified by selection and/or generation as described before. However, it is also possible to genetically modify the cells before they are rendered incapable of expressing endogenous immunoglobulins or parts thereof. Furthermore, it may even appear appropriate to simultaneously effect both steps. are rendered incapable of expressing endogenous immunoglobulins or parts thereof. Furthermore, it may even appear appropriate to simultaneously effect both steps.

Accordingly, it is preferred in a further embodiment that the at least one exogenous genetic element encoding a binding protein or (a) functional fragment(s) thereof, used for effecting the desired genetic modification, is carried on a genetic construct selected from the group consisting of:

(a) recombinant retroviral DNA constructs comprising promoter, enhancer and coding nucleic acid sequences operably linked to ensure expression of at least one binding protein or functional fragment thereof, being either wild-type or having (a) designed mutation(s) in the primary amino acid sequence(s) or being artificial;

(b) recombinant plasmid-based DNA constructs comprising promoter, enhancer and coding nucleic acid sequences operably linked to ensure expression of at least one binding protein or functional fragment thereof, being either wild-type or having (a) designed mutation(s) in the primary amino acid sequence(s) or being artificial;

(c) recombinant plasmid-based mini-immunoglobulin or T cell receptor gene loci with unrearranged V, D and J gene segments operably linked to allow V(D)J recombination and subsequent expression of at least one heterologous antibody or T cell receptor, or functional fragment thereof, being either wild-type or having (a) designed mutation(s) in the primary amino acid sequence(s);

(d) bacterial, yeast or vertebrate artificial chromosomes comprising parts or all of immunoglobulin or T cell receptor gene loci in germline configuration operably linked to allow V(D)J recombination and subsequent expression of at least one heterologous antibody or T cell receptor, or functional fragment thereof, being either wild-type or having (a) designed mutation(s) in the primary amino acid sequence(s);

(e) bacterial, yeast or vertebrate artificial chromosomes comprising parts or all of at least one heterologous immunoglobulin or T cell receptor gene locus in modified arrangement designed to allow V(D)J recombination and subsequent expression of at least one heterologous antibody or T cell receptor, or functional fragment thereof, being either wild-type or having (a) designed mutation(s) in the primary amino acid sequence(s);

one heterologous antibody or T cell receptor, being wild-type with respect to the primary amino acid sequence(s);

wherein the at least one exogenous genetic element most preferably encodes a native or modified human antibody, a human binding protein, a human antigen receptor, or (a) functional fragment(s) thereof.

Furthermore, it is preferred that the at least one exogenous genetic element encodes a heterologous or artificial receptor capable of undergoing affinity maturation of the binding region.

For carrying out the step of genetic modification, several different procedures can be employed according to the invention which are examplified in the following.

A first approach is based on the stable introduction of recombinant plasmid DNA constructs encoding parts of heterologous antigen receptor gene loci in non-rearranged, germline configuration, similar to what has been achieved earlier in the context of transgenic mice. These heterologous antigen receptor gene loci may include V, D and J gene segments of the immunoglobulin H, κL and λL chain gene loci, as well as gene segments from any of T cell receptor (TCR) α, β, γ, or δ gene loci.

A second approach relates to the stable integration of megabase-sized heterologous antigen receptor gene loci, including all or parts of the immunoglobulin and/or TCR gene loci in non-rearranged, germline configuration either as transchromosome fragments, or cloned into bacterial artificial chromosomes (BACs), yeast artificial chromosomes (YACs), or vertebrate artificial chromosomes (VACs), which has also been performed in the context of transgenic mice (Green et al., *Nat. Genet.,* 7, p. 13-21, 1994; Tomizuka et al., *Proc. Natl. Acad. Sci. USA,* 97, p. 722-727, 2000).

The genetic elements of both approaches have to be stably integrated into preB cells carrying cis-acting mutations in their endogenous murine Ig gene loci, that only interfere with the rearrangement of the endogenous Ig gene loci, but that still allow the generation of diverse antibody repertoires from non-rearranged and/or germline heterologous antigen receptor gene loci. The construction of DNA constructs encoding the human Ig gene loci relies on the knowledge of the organization of all human Ig gene loci and their almost completely published DNA sequence as a result of the human heterologous antigen receptor gene loci. The construction of DNA constructs encoding the human Ig gene loci relies on the knowledge of the organization of all human Ig gene loci and their almost completely published DNA sequence as a result of the human genome project. For example, the human IgH chain gene locus is located on chromosome 14q32.33 within a stretch of 1.25 Mbp. It contains 123-129 (depending on allelic variation) $V_H$ gene segments (41-47 of these functional), 27 D, and 6 $J_H$ gene segments upstream of the constant region gene cluster. The human IgκL chain gene locus is located on chromosome 2p12, comprises 1.82 Mbp, and contains 40 or 76 (depending on allele) Vκ gene segments (of which 34 or 64, respectively, functional), and 5 Jκ gene segments upstream of a single Cκ region. The human IgλL chain locus is located on chromosome 22q11.2, spans 1.05 Mbp, and contains 70 or 71 Vλ (31 or 32 functional) gene segments upstream of 7 to 11 tandemly repeated Jλ-Cλ gene segments.

The DNA constructs carrying part(s) or all of the germline heterologous immunoglobulin or T cell receptor gene loci being present on trans-chromosome fragments, or that may be cloned into BAC, YAC, or VAC vector constructs, can be stably transferred into long-term proliferating target preB cells using standard gene transfer procedures, including e.g. electroporation, calcium phosphate or DEAE-dextran transfection, liposome mediated transfer, sphero- or protoplast fusion, ballistic transfer, microinjection, or specific protein-adduct formation, or a combination thereof. Stable transfectants can be selected by virtue of appropriate (drug) selection markers included in the YAC, BAC and VAC vector backbone, comprising genes conferring resistance to e.g. puromycin, hygromycin B, neomycin (G418), histidinol, mycophenolic acid, zeocin and the like.

Figure 9:
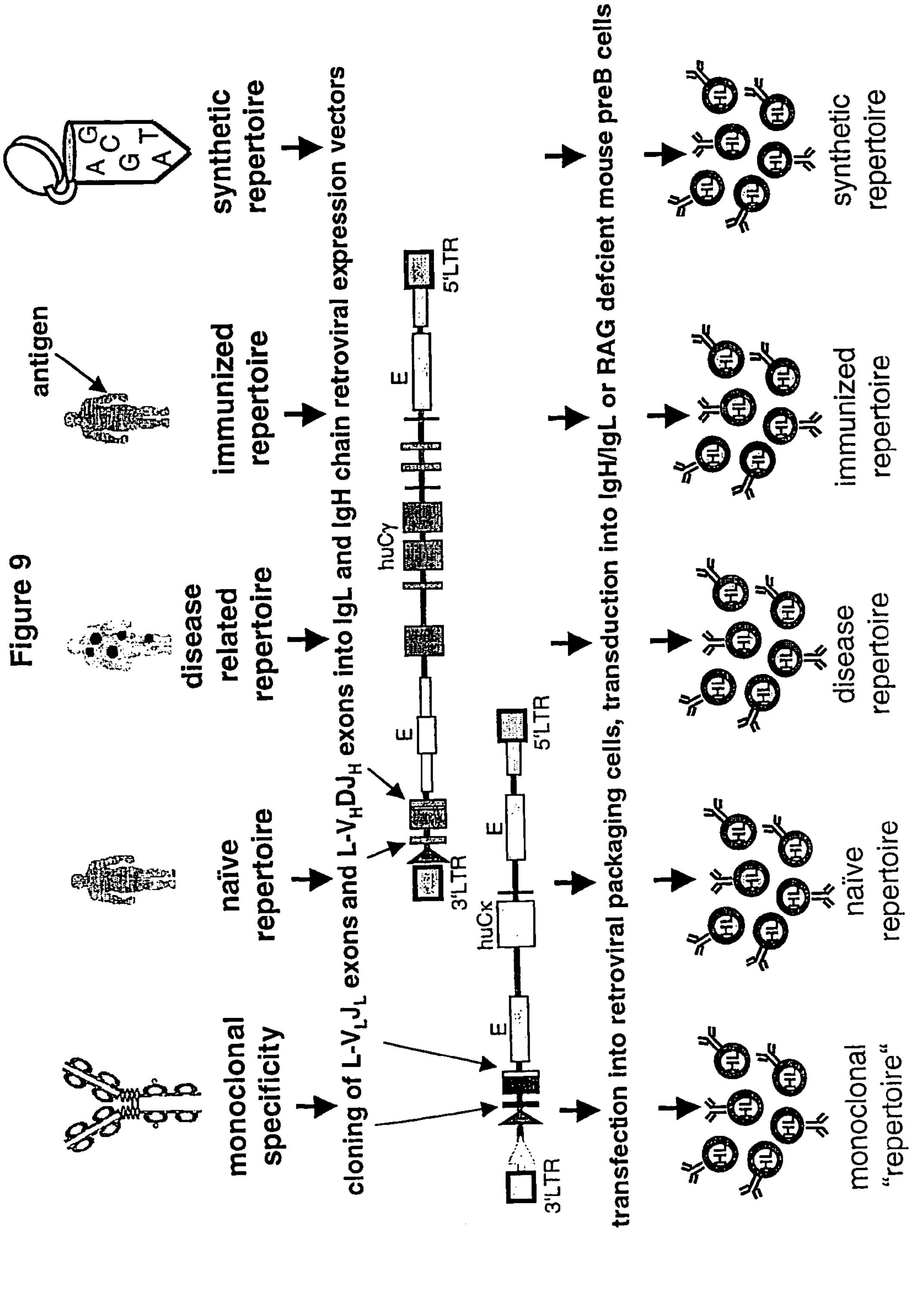
FIG. 9 is a schematic overview of sources, from which variable domain coding regions can be isolated. Variable domain coding regions can be isolated from many different sources, as indicated in this figure. The modular design of the retroviral vectors allows the cloning of retroviral vectors encoding e.g. only a single specificity, for instance from an existing useful monoclonal antibody. Upon transduction of these vectors and transplantation of transduced cells into mice in vivo (see FIG. 10), single specificities may then be subjected to affinity maturation. Alternatively, complete VDJ and VJ libraries may be isolated from peripheral blood lymphocytes (PBLs) from either healthy, sick or immunized patients and then cloned into IgH and IgL chain retroviral expression vectors. In fact, it is even possible to generate completely synthetic $V_H$ and $V_L$ region repertoires, that may be cloned into retroviral Ig expression vectors, which can subsequently be stably transduced and functionally selected in vivo (see FIG. 10).
Figure 10:
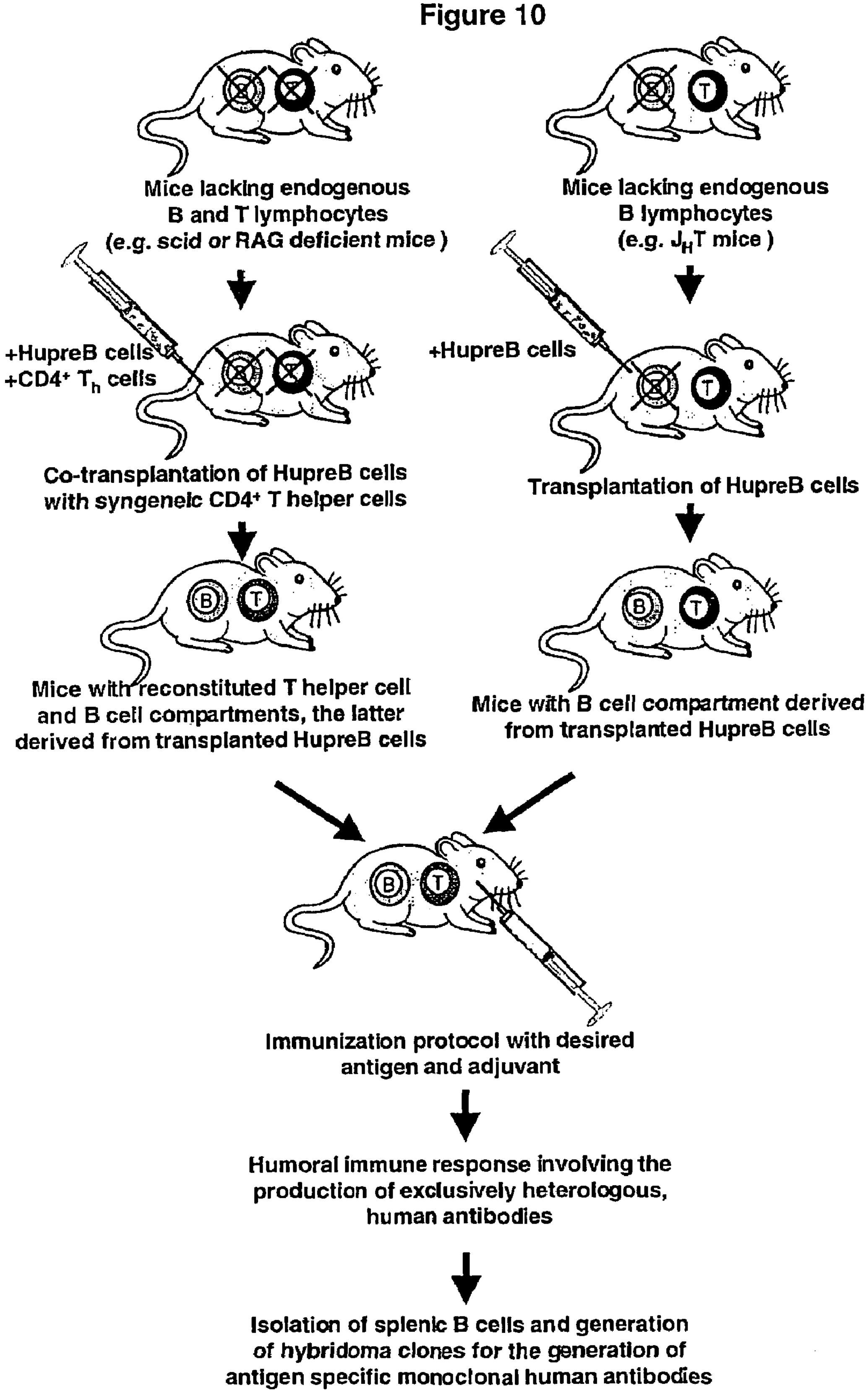
FIG. 10 illustrates transplantation of HupreBs into immunodeficient mice for the production of fully human monoclonal antibodies. HupreB cells, like normal murine preB cells, can be transplanted into murine hosts, where they are able to participate in immune responses of the host. If HupreB cells are transplanted into immunodeficient hosts lacking endogenous B cells, the only antibodies that can then be produced are heterologous (human) antibodies from the transplanted HupreB cells. There are many different host strains that may be used for the transplantation of HupreB cells. Strains that are devoid of both B and T lymphocytes are e.g. the RAG-1- and RAG-2-deficient and scid mouse strains. In order to be able to elicit a T cell dependent immune response involving B lymphocytes derived from transplanted HupreB cells, T helper lymphocyte populations can be isolated and co-transplanted into these mice (left side). Alternatively, mouse strains lacking only B lymphocytes, like e.g. $J_H$ deficient mice, can be reconstituted by transplantation with HupreB cells alone (right side). Once the peripheral B and T lymphocyte compartments are reconstituted after transplantation, these mice can be immunized using convenient immunization protocols against any desired antigen. Plasma cells derived from these mice can then be immortalized, e.g. by fusion with myeloma cells, in order to produce (hybridoma) cells capable of permanently secreting heterologous (human) monoclonal antibodies specific for the injected immunogenic compound or composition.

A third, conceptionally different approach, can be used for introducing heterologous genetic elements encoding heterologous, preferably human antibodies and binding proteins. According to this alternative method, heterologous genetic elements are stably transferred into murine preB cells, using retroviral transduction, that has been described in the context of gene therapy for inherited diseases using pluripotent hematopoietic stem cells as target cells (cf. An Dong Sung et al., J. Virol. 75(8), 3547-3555 (2001)). Retroviral transfer vectors can only accommodate 7-10 kb of foreign DNA, which significantly facilitates the cloning of expression vectors for heterologous, preferably human antibodies and binding proteins. Therefore, all properties of heterologous antibodies and binding proteins can easily and rapidly be modified by standard molecular biology The exon encoding the variable domains within these recombinant retroviral vectors may be monoclonal for the expression of one given specificity, e.g. of an existing antibody whose antigen binding specificity is intended to be modified by affinity maturation after transplantation of stably transduced preB cells into murine hosts and subsequent immunization (FIG. 9). In addition, the exon encoding variable domains may be derived from a library of diverse V(D)J rearrangements. These V region libraries can be isolated from heterologous, preferably human B lymphocytes by PCR using degenerate primer pairs amplifying a multitude of different $V_H$ gene families and $J_H$ gene segments (FIG. 9). The B lymphocytes may be derived from individuals that either have or have not been immunized (primed versus naïve repertoire), or from patients suffering from autoimmune disease (autoimmune repertoire). In addition, completely synthetic libraries of V region domains can be constructed using the in vitro assembly of V domain specific gene fragments that display random nucleotide sequences in regions corresponding to the complementarity determining regions (FIG. 9).

Figure 8:
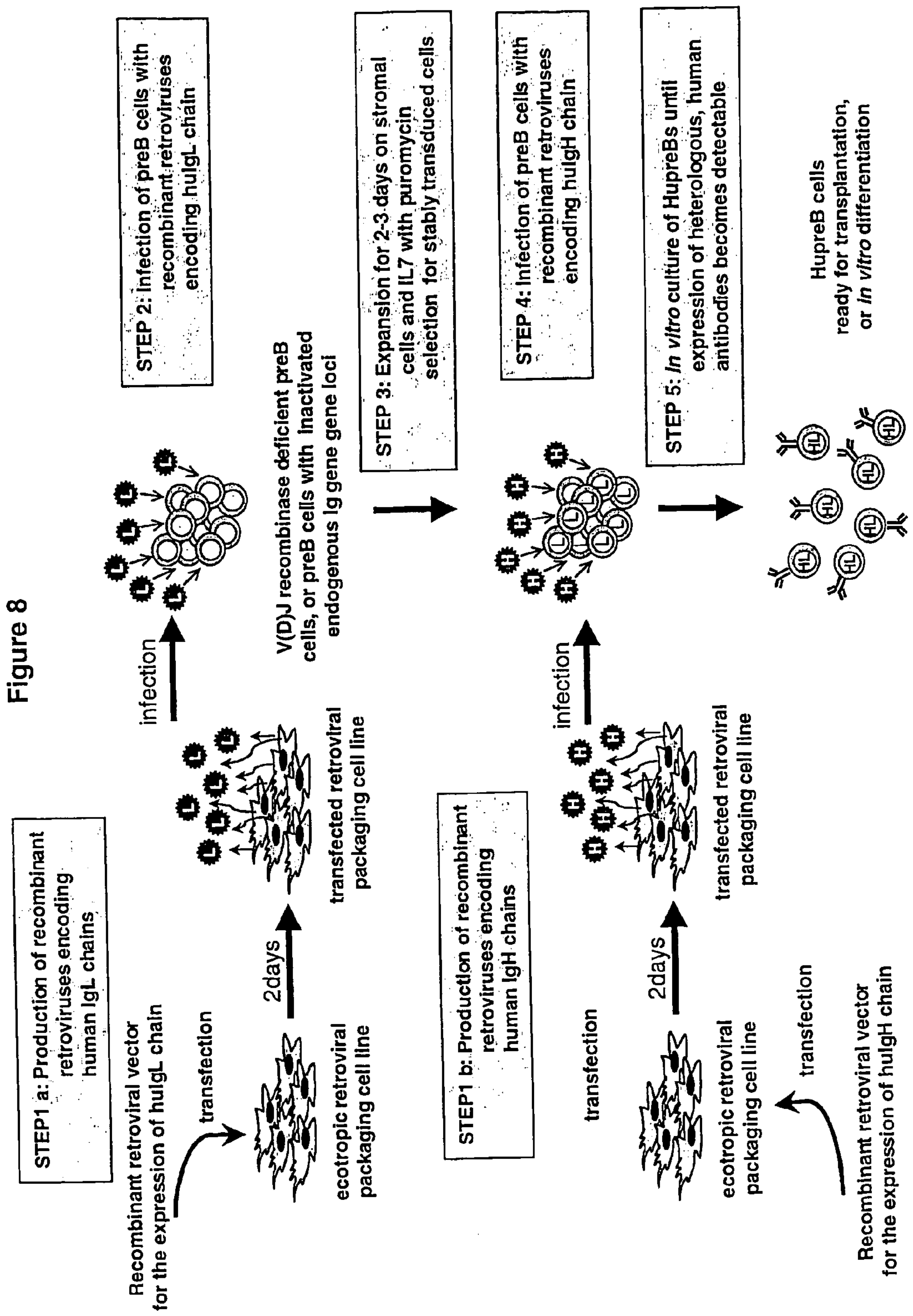
FIG. 8 illustrates the procedure for the retroviral transduction of murine stromal cell/IL7 dependent preB cells with retroviral vectors encoding heterologous IgH and IgL chains. Long-term proliferating stromal cell/IL7 dependent preB cell lines with mutations interfering with endogenous Ig gene rearrangements (cf.

Combinations of retroviral constructs can simultaneously or sequentially be transduced into preB cells allowing the expression and sectretion of complete heterologous immunoglobulins and dimeric binding proteins upon differentiation of the preB cells in vitro or in vivo (FIG. 8).

Vertebrate preB cells that have been genetically modified by any of the above mentioned methods, such that they have gained the potential to express heterologous antibodies or binding proteins, need to be differentiated into mature B lineage cells and eventually plasma cells, such that the heterologous antibodies or binding proteins can be expressed and eventually secreted. This can either be achieved by differentiation in tissue culture in vitro, or upon transplantation of the genetically modified preB cells into appropriate vertebrate hosts in vivo, under the proviso that the in vivo production in humans is excluded.

Accordingly, it is preferred to effect the differentiation of vertebrate precursor B lymphocytes in vitro by:

(a) arresting proliferation of said vertebrate precursor lymphocytes and inducing differentiation into mature lymphocyte lineage cells by cultivating the same in the absence of any precursor lymphocyte growth factor; and (b) inducing terminal lymphocyte differentiation by further cultivating said cells in the presence of at least one of the following components selected from:

(i) soluble T cell related stimulating factors, comprising interleukin-2, interleukin-4, interleukin-5, interleukin-6, interleukin-10, interleukin-13, TGF-β, and IFN-γ;

(ii) factors activating co-stimulatory receptors of B cells, comprising agonistic antibodies or active, recombinant ligands specific for CD40, B7-1 (CD80), B7-2 (CD86), complement receptors 1 (CD35) and 2(CD21), LFA-1 (CD11a), LFA-3 (CD58), CD19, CD20, CD30, CD32, CD37, CD38, CD70, CD71, Igα (CD79α), Igβ (CD79β), TAPA-1 (CD81), Fas (CD95), TNF-receptor1 (p55, CD120a), TNF-receptor2 (p75, CD120b), Ox-40 (CD134), and lymphotoxin-b receptor; and (iii) B cell mitogenic factors, T cell independent antigens of type 1, and other polyclonal activators, including lipoplysaccharide (LPS), lipoproteins from gram negative bacteria, polyanions, poly-dldC, pokeweed mitogen (PWM), and anti-immunoglobulin reagents; and combinations thereof.

The in vitro differentiation in tissue culture can be achieved by a two step process, including (a) the removal of preB cell growth factors, like e.g. IL7, or IL3, from the tissue culture medium, which will arrest proliferation of preB cells and at the same time will induce differentiation into cells of a mature B cell phenotype, and including (b) stimulation of the differentiated B cells by said T cell related and/or mitogenic, T cell independent stimuli, such that terminal plasma cell differentiation will be induced. The initial differentiation of preB cells into cells with a B cell phenotype by removing preB cell growth factors is accompanied by the induction of apoptosis. It is thus a preferred embodiment to use preB cells overexpressing anti-apoptotic genes, like e.g. bcl-2 or bcl-$x_L$. These anti-apoptotic genes can be introduced into preB cells either by using preB cells that have been isolated from bcl-2, or bcl-$x_L$ transgenic animals, or by transfecting or transducing preB cells with overexpression vectors for any of the anti-apoptotic genes.

As an alternative to the in vitro differentiation of genetically modified precursor lymphocytes, these cells can also be differentiated in vivo upon transplantation into a suitable vertebrate non-human host, resulting in migration of these cells to secondary lymphoid organs and differentiation into more mature lymphoid lineage cells. Preferably, said lymphocytes are co-transplanted into said host with naïve or antigen primed T helper lymphocytes, wherein the term 'co-transplanted' is to be understood not to be limited to the simultaneous transplantation at exactly the same time. According to another preferred embodiment, the differentiation in vivo is followed by immunization of said host with at least one desired immunogenic compound or composition. In contrast to the method described herein, the transplantation of genetically unmodified human CD34+ hematopoietic stem cells into SCID mice (WO 01/87058) does neither allow the generation of high affinity antibodies (because of the lack of compatible human T cells) nor any flexibility in the type and properties of the antibodies produced by these B cells.

Furthermore, it is preferred that said vertebrate host is a compatible host being deficient with respect to the generation of endogenous B cells, T cells, and/or NK (natural killer) cells, or a combination thereof.

As already set forth hereinbefore with respect to the selection of appropriate sources for vertebrate precursor lymphocytes, it is preferred that the vertebrate host is selected from jawed vertebrates comprising cartilaginous fish, bony fish, amphibians, reptilia, birds, and mammals including pigs, sheep, cattle, horses and rodents including mice, rats, rabbits and guinea pigs, with mice being the preferred host species.

The appropriate hosts serving as recipients for the transplantation of genetically modified vertebrate precursor lymphocytes may be wild-type with respect to lymphocyte development, or they may preferably harbour any of various cis acting mutations inhibiting endogenous murine Ig gene rearrangements. These may include mutations in enhancer elements of Ig gene loci, like the aforementioned EμH and κiE enhancer elements, deletions within Ig gene coding regions, like the $D_H$, the $J_H$ or $J_L$ gene segments and the IgC regions including their membrane spanning exons. Furthermore, suitable hosts can be used carrying trans acting mutations selectively impeding B (and T) lymphocyte development, e.g. mutations in lineage or lymphocyte specific transcription factors or the RAG-1 and RAG-2 genes required for the initiation of V(D)J recombination (Mombaerts et al., s.a.; Shinkai et al., s.a.).

Furthermore, trans-acting mutations leading to immunodeficient hosts comprise mutations in the ubiquitously expressed DNA repair genes also required for V(D)J recombination like, Ku70, Ku86, the catalytic subunit of the DNA-dependent protein kinase (DNA-PKcs), XRCC4, DNA ligase IV and Artemis. Vertebrate hosts with any of the aforementioned mutations lacking either B lymphocyte populations alone, or both B and T lymphocytes, can then be transplanted with the genetically modified preB cells, and in the case of B- and T cell deficient mice, may be co-transplanted with histocompatible T helper cell populations. The T helper cell populations preferably comprise naïve T helper cell, antibody primed effector T cell populations or memory T cells, or any combination thereof. Co-transplantation of T helper cell populations may occur simultaneaously, before or after the actual timepoint of the transplantation of genetically modified preB cells.

Murine or vertebrate hosts whose peripheral lymphocyte populations have been partially or fully reconstituted by the transplantation of modified preB cells and the optional co-transplantation of T helper cell populations can then be used for the immunization with any desired antigen, in order to trigger an immune response to that antigen and to stimulate such lymphocytes expressing the appropriate heterologous receptor specificty, which lead to the proliferative expansion of B cell clones, the affinity maturation of the binding domains of the encoded heterologous antibodies or binding proteins, and the terminal differentiation into plasma cells secreting the heterologous antibodies or binding proteins.

As will be apparent from the foregoing, a further aspect of the present invention is to provide a method for the production of any binding protein or functional fragment(s) thereof with the ability to selectively bind to an antigen or ligand, including any heterologous antibody, any antigen receptor composed of variable domains and constant regions comprising T cell receptors and membrane bound immunoglobulins, any artificial binding protein displaying either wild-type immune effector functions or modified or artificial effector functions not derivable from germline encoded heterologous immunoglobulins or antigen receptors, and any functional fragment(s) thereof, in a manner known per se, involving the steps of:

(a) genetically modifying vertebrate precursor lymphocytes, which
  (i) are derived from primary lymphoid organs, and
  (ii) have the potential to differentiate into mature lymphoid lineage cells, by introducing at least one exogenous genetic element encoding at least one binding protein or functional fragment thereof; or, alternatively, using genetically modified vertebrate precursor lymphocytes, which
  (i) are derived from primary lymphoid organs,
  (ii) have the potential to differentiate into mature lymphoid lineage cells, and
  (iii) carry at least one exogenous genetic element encoding at least one binding protein or functional fragment thereof;
(b) effecting differentiation of said genetically modified precursor lymphocytes into mature lymphoid lineage cells either in vitro or in vivo, thereby generating genetically modified and differentiated vertebrate lymphocytes capable of producing said binding protein or functional fragment thereof; or, alternatively, using said genetically modified and differentiated vertebrate lymphocytes capable of producing said binding protein or functional fragment thereof,
(c) effecting expression of the binding protein or functional fragment(s) thereof; under the proviso, that the in vivo production in humans is excluded.

In this context, it is preferred that any of the above methods involving the generation of the genetically modified and differentiated vertebrate lymphocytes is followed by the steps of:
  (a) isolating from said differentiated lymphocytes the at least one exogenous genetic element, and
  (b) placing said genetic element(s) in a context enabling production of said at least one binding protein or functional fragment(s) thereof.

In order to achieve large scale production of the desired immunoglobulin or immunoglobulin-like protein or functional fragment thereof, the genetic information which codes for the polypeptides of interest can be isolated from these cells and transferred into different expression systems, where the genetic information can be maintained, amplified and/or used for the production of the desired protein or part thereof.

In more detail, the open reading frames representing coding regions for the heterologous antibodies or binding proteins can be isolated by standard molecular biology methods, including PCR amplification with specific primer pairs, and transferred into the context of different expression systems, allowing the continuous production of the heterologous antibodies or binding proteins. These expression systems comprise in vitro transcription/translation systems, prokaryotic expression systems, like e.g. *E. coli*, or eukaryotic expression systems, like expression in yeast cells, insect cells using baculovirus infection, or mammalian cells.

The above-mentioned binding protein or functional fragment(s) thereof can either display one unique specificity and can therefore be monoclonal, or can be encoded by more than one unique specificity and can therefore be polyclonal.

According to a preferred embodiment, said binding protein or functional fragment(s) thereof completely or partially shares structural and/or functional features of a human antibody, antigen receptor, or binding protein, as can be assembled on the basis of the human genetic repertoire or parts thereof.

Furthermore, it is preferred that the binding protein or functional fragment(s) thereof to be produced is selected from the group consisting of:

(a) antibodies being either membrane bound or secreted, and consisting of both heterologous heavy and light chain polypeptides in the stochiometric composition found in natural antibodies and consisting of any of the known heavy (μ, δ, γ, α, ε) and/or light (κ and λ) chain isotypes;

(b) antibodies with combinations of heavy and light chain polypeptides being completely human with respect to the primary amino acid sequence;

(c) hybrid antibodies containing heterologous heavy or light chain polypeptides from different vertebrate species;

(d) secreted Fab, scFv and F(ab')2 antibody fragments being either completely or partially heterologous;

(e) fragments of antibodies covalently coupled via linker peptides, resulting in bispecific or multispecific antibody fragments;

(f) T cell receptors of the α, β, γ, and δ isotype, antigen receptors, and other binding proteins with structural resemblance to proteins of the immunoglobulin superfamily;

and functional fragments thereof.

According to another aspect, the present invention provides genetically modified vertebrate precursor lymphocytes, which (a) are derived from primary lymphoid organs and have the potential to differentiate into mature lymphoid lineage cells, (b) carry at least one exogenous genetic element encoding at least one heterologous binding protein or functional fragment thereof with the ability to selectively bind to an antigen or ligand, including any heterologous antibody, any heterologous antigen receptor composed of variable domains and constant regions comprising T cell receptors and membrane bound immunoglobulins, any heterologous artificial binding protein displaying either wild-type immune effector functions or modified or artificial effector functions not derivable from germline encoded heterologous immunoglobulins or antigen receptors, and any functional fragment(s) thereof, and (c) carry at least one selection marker being operably linked to said at least one exogenous genetic element.

According to still another aspect, the present invention provides mature lymphoid lineage cells, which (a) carry at least one exogenous genetic element encoding at least one heterologous binding protein or functional fragment thereof with the ability to selectively bind to an antigen or ligand, including any heterologous antibody, any heterologous antigen receptor composed of variable domains and constant regions comprising T cell receptors and membrane bound immunoglobulins, any heterologous artificial binding protein displaying either wild-type immune effector functions or modified or artificial effector functions not derivable from germline encoded heterologous immunoglobulins or antigen receptors, and any functional fragment(s) thereof, and (b) carry at least one selection marker being operably linked to said at least one exogenous genetic element.

According to a further aspect, the present invention provides immortalized cells derived from mature lymphoid lineage cells, which (a) carry at least one exogenous genetic element encoding at least one heterologous binding protein or functional fragment thereof with the ability to selectively bind to an antigen or ligand, including any heterologous antibody, any heterologous antigen receptor composed of variable domains and constant regions comprising T cell receptors and membrane bound immunoglobulins, any heterologous artificial binding protein displaying either wild-type immune effector functions or modified or artificial effector functions not derivable from germline encoded heterologous immunoglobulins or antigen receptors, and any functional fragment(s) thereof, (b) carry at least one selection marker being operably linked to said at least one exogenous genetic element, and (c) produce said at least one heterologous binding protein or functional fragment thereof.

Furthermore, there are provided vector constructs suitable for at least partially inactivating vertebrate precursor lymphocytes to express endogenous immunoglobulins or part(s) thereof, and genetic constructs carrying at least one exogenous genetic element encoding a heterologous antibody, an artificial binding protein, an antigen receptor, or (a) functional fragment(s) thereof, as defined hereinabove.

According to a further aspect, the present invention provides pharmaceutical or diagnostic preparations, comprising at least one antibody, artificial binding protein, antigen receptor, or functional fragment thereof, obtained by any of the methods mentioned before, displaying either wild-type immune effector functions, or modified or artificial effector functions not derivable from germline encoded heterologous immunoglobulins or antigen receptors.

As will be appreciated, fully human or humanized antibodies or functional fragment(s) thereof can be used in the diagnosis, prevention and therapy of human disease by virtue of their ability to bind with their variable region domains to specific antigens, and, furthermore, by their ability to mediate immune effector functions via their constant region domains. Some possible uses of human monoclonal antibodies, which can be produced according to the invention, for the diagnosis, prevention and therapy of human disease are detailed below. For diagnostic purposes, human monoclonal antibodies can be used for the identification and visualization of certain pathologic conditions by the introduction of labeled antibodies into the vascular system of individuals, where specific disease related antigenic structures (e.g. expressed on certain pathologic cells) can be detected. Applications in the prevention of human disease include antibodies with the ability to block interactions of certain cell surface receptor-ligand systems in pathologic conditions (antagonistic antibodies), or conversely, to mimick the effect of ligand binding to cell surface receptors (agonistic antibodies) in case of the pathologic absence of a ligand. Furthermore, human monoclonal antibodies can be used for blocking the functions of toxic substances, or of pathogens, e.g. during poisoning, inflammation, and infections. In this context, human antibodies are of particular use, because they mediate the tagging of these substances and antigens for the removal by specialized cells of the innate immune system. Human monoclonal antibodies can also be used for targeting immune functions to cancerous cells by virtue of specific binding to altered self structures expressed on the surface of malignant cells. In case of autoimmune conditions, human monoclonal antibodies may further be useful for neutralizing or counteracting the pathologic effects of autoimmune factors (autoantibodies, allergic antibodies). Human monoclonal antibodies are so useful for the diagnosis, prevention and therapy of human disease, because they can be introduced into the vascular system of individuals, without causing any adverse effects, as antibodies are normal constituents of blood plasma and fluid components of humans (e.g. mucus, saliva, lymph fluid etc.).

Deposition of Biological Material

Plasmids carrying genetic elements used in accordance to the present invention have been deposited under the Budapest Treaty with the Deutsche Sammlung von Mikroorganismen und Zellkulturen (DSMZ) in Braunschweig, Germany, on Dec. 17, 2001, under the following Accession Nos.:

| Plasmid | Accession No. |
|---|---|
| pBS-DT4 | DSM 14703 |
| pPGK-hygro | DSM 14704 |
| pGL2neo(m)+ | DSM 14705 |
| pBS-DT4-tox176 | DSM 14706 |

The following experimental procedures describe detailed methods for the generation of human monoclonal antibodies using murine preB cells that are genetically modified in order to confer the potential for human antibody production. Selected examples of methods are described as follows allowing the genetic modifications of murine preB cells, such that endogenous antibodies can no longer be expressed, but that human antibodies can be produced from stably delivered heterologous retroviral expression constructs. Furthermore, experimental details are presented relating to the transplantation of these genetically modified murine preB cells into appropriate murine hosts, as well as methods relating to the immunization of these transplanted mice, the isolation of antibody secreting cells, and their establishment as immortal monoclonal human antibody secreting hybridoma cell lines. Although the provided methods are complete and sufficient for the production of heterologous, especially human monoclonal antibodies using murine preB cells, that are genetically modified, the methods should not be viewed by way of limitation, but rather by way of illustration.

EXAMPLES

Example 1

Establishment of Long-Term Proliferating, Murine Precursor B Cells with the Potential to Differentiate into Mature B Lineage Cells Stromal cell and IL7 responsive murine precursor B cells are found in fetal liver of mouse fetuses at day 15-18 post-coitum, in the bone marrow of adult mice, as well as in the spleen of newborn animals (<3 weeks of age) (Rolink et al., *Blood,* 81, 2290-2300, 1993). In order to isolate these preB cells, mice are sacrificed by $CO_2$ suffocation and the respective organs are removed under sterile conditions. Total bone marrow cells are obtained by removing femur and tibia, opening of the bones at both ends with sterile scissors and flushing the marrow with 2-5 ml phosphate buffered saline (PBS) using a 5 ml disposable syringe and a 25 or 26 gauge needle. Isolated spleen or fetal liver also prepared under sterile conditions is placed onto a sterile 200 mesh steel grid in a petri dish with 5-10 ml of PBS. The organs are cut into pieces and gently squashed through the metal grid with the plunger of a 5 ml plastic syringe. Cell suspensions are washed once by centrifugation (200 g, 10 min, 4° C.) and resuspended in 10-20 ml PBS. All cell preparations are carried out with ice-cold solutions, and cell suspensions are kept on ice until transfer into tissue culture.

Establishment of individual preB cell clones is performed by limiting dilution in 96-well plates coated with semi-confluent, 3000rad γ-irradiated ST-2 (Ogawa et al., *EMBO J., Z, p.* 1337-1343, 1988) or PA-6 (Kodama et al., *J. Cell. Physiol.,* 118, p. 233-240, 1984) murine stromal cells grown in special stromal cell medium (see below). For limiting dilution plating, total organ cell populations can be used or, alternatively, $B220^+$ or $CD19^+$ surface marker positive B lineage cells enriched by fluorescent or magnetic bead activated cell sorting (FACS or MACS) using commercial antibodies specific for these markers.

The long-term culture of murine preB cells is performed in a special serum-free medium, containing 100 units of recombinant interleukin-7 (IL-7) (see below). Individual preB cell colonies develop on stromnal cell feeders under limiting dilution conditions within 6-7 days of culture at 37° C., in a humidified incubator under a 10% $CO_2$ atmosphere. Single preB cell colonies are initially transferred into 24-well plates, and then sequentially expanded into 25 $cm^2$ and eventually 75 $cm^2$ tissue culture flasks, always pre-coated with 3000rad γ-irradiated stromal cells. After the initial expansion, preB cell densities need to be kept between $1\times10^5$ and $2\times10^6$ preB cells/ml tissue culture medium, which requires subculturing of the cells every two to three days.

Special serum-free tissue culture medium (Iscove and Melchers, *J. Exp. Med.,* 147, p. 923-933, 1978) required for the establishment of long-term proliferating, stromal cell, IL-7 dependent murine preB cells (formulation for 1 liter of medium):

| | | |
|---|---|---|
| 11 g | DMEM-powder (without bicarbonate) | |
| 10 ml | 1 M HEPES, pH 7.3 | |
| 33.3 ml | 7.5% $NaHCO_3$ solution | |
| 8 ml | amino acid stock solution containing: | |
| | L-alanine | 600 mg |
| | L-asparagine | 520 mg |
| | L-aspartate | 720 mg |
| | L-glutamate | 1800 mg |
| | L-proline | 960 mg |
| | Na-pyruvate | 2640 mg |
| +1.6 ml | Biotin/Vitamin B12 stock solution containing | |
| | Vitamin B12 | 5.0 mg |
| | D-biotin | 5.0 mg |
| | dissolved in 20 ml + 10 μl 1 M HCl | |
| | all components dissolved in 240 ml ultrapure $H_2O$ | |
| 4 ml | cysteine stock solution containing | |
| | L-cysteine | 1.4 g |
| | dissolved in 150 ml $H_2O$, 50 ml 1 M HCl | |
| 5 ml | 10% BSA (Bovine serum albumine) solution | |
| 0.15 ml | human transferrin stock solution composed of: 10 ml of solution a.) and 80 μl solution b.) | |
| | a.) 1 g human transferrin dissolved in 10 ml DMEM (1.3 g/100 ml $H_2O$) + 100 μl 1 M HEPES, pH 7.3 | |
| | b.) 440 mg $FeCl_3 \times 6\ H_2O$ + 185 ml $H_2O$ + 200 μl 1 M HCl | |
| 5 ml | soybean-lipid stock solution | |
| | 200 mg soybean lipids mixed with 45 ml DMEM (1.3 g/100 ml $H_2O$) + 5 ml 10% BSA. Sonication 3 × 15 min in ice-water. | |
| 20 ml | kanamycin (5000 μg/ml) | |
| 30 μl | 2-mercaptoethanol (1.43 M) | |
| $10^5$ U | recombinant mouse interleukin-7 (IL7) | |

All components are dissolved in a final volume of 1000 ml triple-distilled, ultrapure $H_2O$, filtered sterile and kept at 4° C. until use.

ST-2 or PA-6 stromal cell feeder cells need to be grown in a special, low serum containing medium as follows (formulation for 1 liter):

| | | |
|---|---|---|
| 17.7 g | IMDM-powder (without bicarbonate) | |
| 3 g | $NaHCO_3$ | |

-continued 10 ml 100× non-essential amino acids (GIBCO-BRL)
10 ml 100× Penicillin/Streptomycin (GIBCO-BRL)
 1 ml 5 mg/ml porcine insulin-solution
 1 ml 50 mM 2-mercaptoethanol
 3 ml 10% primatone (ultrafiltrated to exclude proteins >10 kD)
   (source: Quest International, Naarden, NL)
20 ml fetal calf serum All components are dissolved in a final volume of 1000 ml triple-distilled, ultrapure $H_2O$, filtered sterile and kept at 4° C. until use.

Example 2

Stepwise Differentiation of Murine Precursor B Cells into Antibody Secreting Plasma Cells In Vitro Long-term proliferating, stromal cell and IL7 dependent murine preB cells retain their potential to differentiate into more mature B lineage cells (Rolink et al., s.a.), which can be achieved in vitro. This differentiation can be performed in two steps by first inducing differentiation to cells with an immature B cell phenotype and, second, by inducing differentiation to cells with a phenotype of antibody secreting plasma cells.

The first differentiation stage is reached by removing IL7 from the preB cells in the continued presence of stromal cells. For this preB cells are harvested from proliferating cultures, washed three times with serum free preB cell culture medium lacking IL7 and plated at a density of 1-2×10$^6$ cells/ml onto fresh, 3000rad γ-irradiated stromal cells in the absence of IL7. Within a period of three days the preB cell cease to proliferate and differentiate into cells with a phenotype of immature B cells. The phenotypic changes include e.g. the loss of c-kit, $\lambda_5$ and $V_{preB}$ expression and the gain of CD25 and CD40 expression. In preB cells from wild-type mice, this differentiation is further accompanied by sequential $V_H$ to $DJ_H$ rearrangements on the IgH chain gene loci followed by $V_L$ to $J_L$ rearrangements on the IgL chain gene loci, which may result in the expression of surface bound IgM antibody on the differentiated B lineage cells (Rolink et al., s.a.). However, it has to be noted that the ordered rearrangement of IgH and L gene segments is not a prerequisite for the phenotypic differentiation of these preB cells in vitro (Grawunder et al., 1995, s.a.).

The second differentiation stage can be achieved by stimulating the IL7 deprived cells with either an agonistic anti-CD40 antibody or LPS in combination with cytokines, like e.g. IL4, IL5, IL10 or TGF-β. This treatment will induce proliferation, class switch recombination to various Ig gene isotypes (depending on the cytokine combination employed) and eventually differentiation to antibody secreting plasma cells. In case of e.g. anti-CD40/IL4 stimulation, cells are washed three times in preB cell tissue culture medium, plated onto fresh, subconfluent 3000rad γ-irradiated stromal cells in the presence of 100 U/ml IL4 and 5 μg/ml anti-CD40 monoclonal antibody for 4-6 days. Large, proliferating plasma cell stage cells can be identified and separated by fluorescent activated cell sorting (FACS), based on their large size which results in distinctly increased forward scatter values.

The in vitro differentiation of wild-type preB cells is usually accompanied by loss of substantial amounts of cells due to growth factor withdrawal induced apotosis. This problem can be circumvented by overexpression of anti-apoptotic genes, like bcl-2 or bcl-$x_L$ in these cells (Rolink et al., 1993, s.a.). This can be achieved by isolating preB cells from mice containing a B lineage specifically expressed bcl-2 transgene (Strasser et al., Curr. Top. Microbiol. Immunol., 166, p. 175-181, 1990), or by transducing a bcl-2 encoding recombinant retroviral vector into the long-term proliferating, stromal cell and IL7 dependent murine preB cells (see below).

Example 3

Cloning of a Retroviral Expression Construct for Murine Bcl2 Overexpression

Figure 11A:
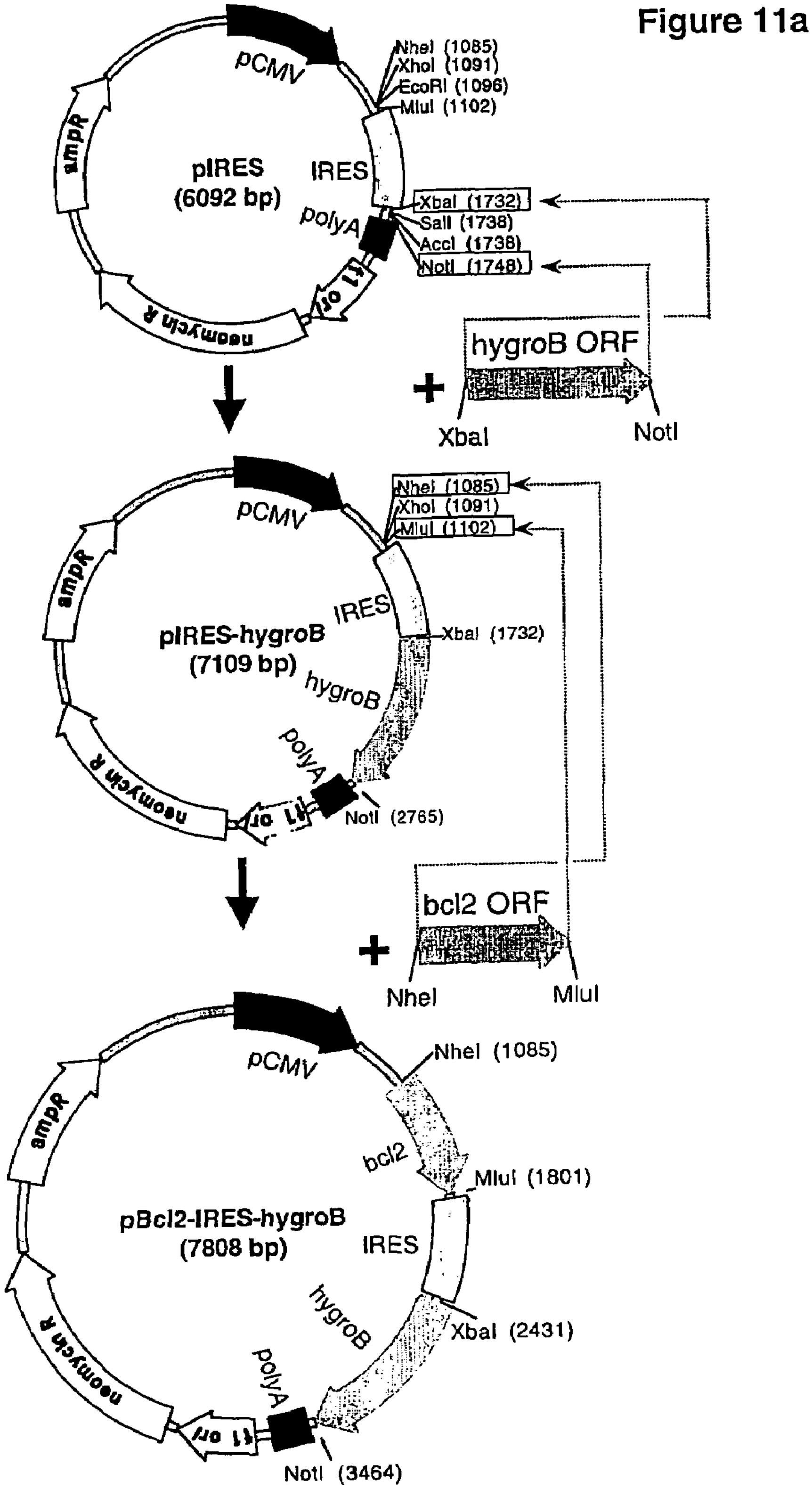
FIG. 11*a* illustrates the construction of a retroviral expression vector for constitutive expression of the anti-apoptotic gene bcl-2 (preparatory steps). Removal of IL-7 from continuously proliferating preB cell cultures in vitro results in the differentiation of preB cells, but at the same time also leads to the induction of apoptosis. This apoptosis can be prevented by constitutive expression of an anti-apoptotic gene, like e.g. bcl-2. For the generation of a selectable retroviral expression vector for bcl-2, the murine bcl-2 cDNA is sequentially cloned with an hygromycin B open reading frame into a dual gene expression vector pIRES. This vector contains an internal ribosomal entry sequences flanked by two multiple cloning sites, into which two different genes can be cloned. This allows the simultaneous expression of two genes in mammalian cells from one single promoter. The strategy for the insertion of the bcl-2 ORF and the hygromycin B selection marker gene into pIRES for the generation of a pBcl2-IRES-hygroB vector is indicated.
Figure 11B:
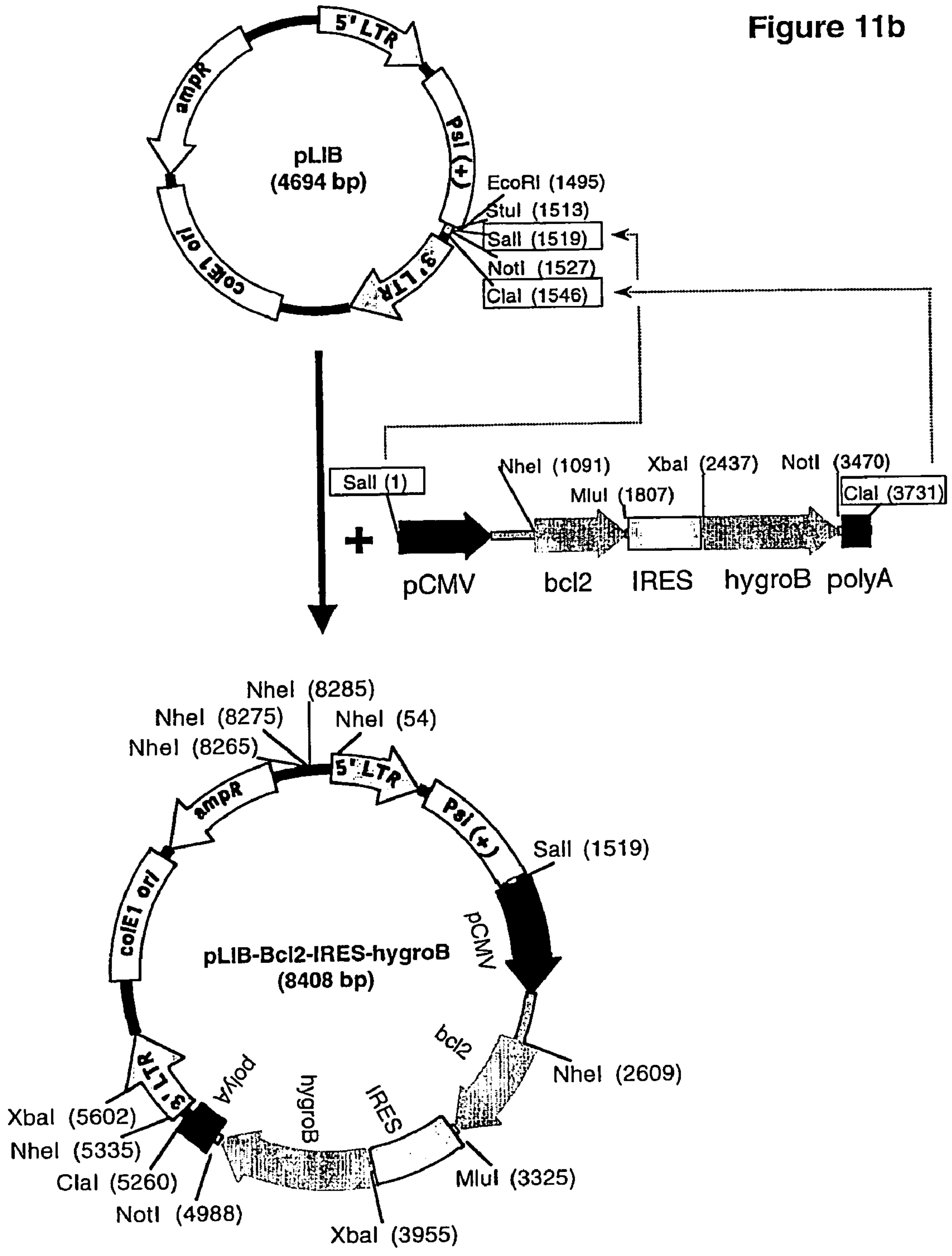
FIG. 11*b* illustrates the construction of a retroviral expression vector for constitutive expression of the anti-apoptotic gene bcl-2 (final cloning step). After assembly of the CMV promoter driven bcl-2-IRES-hygromycinB cassette, the entire dual expression cassette from the pBcl2-IRES-hygroB vector is recloned as a SalI-ClaI fragment into the retroviral transfer vector pLIB, as depicted. This generates the recombinant retroviral construct pLIB-Bcl2-IRES-hygroB that can be used to stably transduce preB cells and to confer simultaneous expression of bcl-2 and resistance to hygromycinB.

A prerequisite for the stable transduction of genes into long-term proliferating, stromal cell and IL7 dependent murine preB cells is the construction of a recombinant retroviral transfer vector containing an expression cassette for a gene of interest. Retroviral transfer vectors consist of retroviral 5' and 3' long terminal repeat (LTR) sequences flanking a retroviral packaging signal, Psi(+), a multiple cloning site (MCS) into which heterologous sequences can be inserted, and bacterial plasmid control elements required for replication and maintenance of the vector in E. coli. An example for an empty retroviral transfer vector is the commercially available plasmid pLIB (Clontech) (FIG. 11a).

In order to construct a retroviral expression vector containing the anti-apoptotic gene bcl-2, a strategy for coexpression of the murine bcl-2 cDNA and the hygromycinB drug selection marker is applied by linking expression of bcl-2 and hygromycinB using an internal ribosomal entry sequence (IRES), allowing simultaneous expression of two genes from a single promoter. With this strategy, stable integration of the vector construct, which can be selected with the antibiotic drug hygromycin B will simultaneously select cells for the expression the anti-apoptotic gene bcl-2. The generation of the retroviral vector for coupled expression of the bcl-2 and hygromycinB cDNAs proceeds in two stages, first the assembly of the promoter-bcl-2-IRES-hygromycinB expression cassette and, second, the cloning of this cassette into the MCS of the retroviral transfer vector pLIB (FIG. 11a+b).

(a) Construction of the Promoter-bcl-2-IRES-hygromycinB Expression Cassette

Both the murine bcl-2 cDNA and the open reading frame (ORF) for the hygromycinB drug resistance marker are cloned into the commercially available CMV-promoter/IRES vector pIRES (Clontech). For this, the hygromycinB ORF is amplified from plasmid pPGK-hygro (SEQ ID NO 1) by polymerase chain reaction (PCR) using primer pair:

SEQ ID NO. 5 (P001)
5'-cgTCTAGAccatgaaaaagcctgaactcaccgcgacgtctg-3',
and

SEQ ID NO. 6 (P002)
5'-catGCGGCCGCtattcctttgccctcggacgagtgctgggg-3' containing additional restriction enzyme recognition sites (indicated in uppercase letters) for restriction endonucleases XbaI and NotI (2-4 random nucleotides 5' of the restriction enzyme recognition sequence are also added, because most restriction enzymes do not efficiently digest DNA, if the recognition sequence is located directly at the end of PCR amplified DNA fragments. These flanking nucleotides are indicated in lowercase letters, in order to highlight the restriction enzyme recognition sites. The sequences downstream, or 3' of the highlighted restriction sites correspond to DNA sequences of the fragment to be amplified. This way of presentation of primer sequences is maintained throughout the description of experimental examples. A PCR with primers P001 and P002 will amplify a DNA fragment of 1017 basepairs (bp) containing unique recognition sites for restriction endonucleases XbaI and NotI at the ends of the fragment. The PCR fragment is then double digested with XbaI and NotI restriction enzymes and is then directionally cloned into XbaI/NotI double digested pIRES plasmid, in order to generate the plasmid construct pIRES-hygroB (FIG. 11a). The ORF of the murine bcl-2α cDNA is isolated and amplified from mouse spleen mRNA by reverse transcriptase coupled polymerase chain reaction (RT-PCR) using the following primers designed based on the published NCBI-Genbank sequences M16506 and L31532 (primer P003 binding to position 1821-53 of M16506, and primer P004 binding to position 506-535 of L31532):

SEQ ID NO. 7 (P003)
5'-attGCTAGCatggcgcaagccgggagaacagggtatgataac-3'
and

SEQ ID NO. 8 (P004)
5'-cgcACGCGTcacttgtggcccaggtatgcacccagagtg-3 containing restriction enzyme recognition sites (in uppercase letters) for NheI and MluI. A NheI/NotI double digested PCR product of 699 bp size is then directionally cloned into NheI/MluI double digested vector pIRES-hygroB in order to generate pBcl2-IRES-hygroB.

(b) Construction of a Retroviral Bcl-2 Expressing Transfer Vector

Due to the lack of compatible restriction enzyme sites in the multiple cloning site of the empty retroviral transfer vector pLIB and the dual bcl-2/hygromycinB expression vector pBcl2-IRES-hygroB, the entire expression cassette for Bcl-2-IRES-hygromicinB including the constitutive CMV promoter and polyadenylation site is cloned into pLIB using PCR with appropriated restriction enzyme recognition sites. For this the CMV-bcl2-IRES-hygromycinB expression cassette is PCR amplified with pBcl2-IRES-hygroB as the PCR template using primers:

SEQ ID NO. 9 (P005)
5'-atatGTCGACtcaatattggccattagccatattattcattg-3'
and

SEQ ID NO. 10 (P006)
5'-ccggATCGATccttatcggattttaccac-3' containing restriction enzyme recognition sites for SalI and ClaI (in uppercase letters). A SalI/ClaI double digested PCR product of 3714 bp is then directionally cloned into the Sal/ClaI double digested pLIB vector thereby generating retroviral transfer vector pLIB-bcl2-IRES-hygroB allowing coupled bcl-2 and hygromycinB expression.

Example 4

Retroviral Transduction of Long-Term Proliferating, Stromal Cell and IL7 Dependent Murine preB Cells One of the ways to stably transfer genetic elements into murine preB cells is to use retroviral transduction (FIG. 8). For this procedure a recombinant DNA construct containing retroviral sequences necessary for packaging of a retroviral genome (5'LTR, packaging signal Psi(+), 3'LTR) as well as heterologous sequences or genes of interest, are transiently or stably transfected into a packaging cell line constitutively expressing genes required for the production of retroviral particles.

For the transduction of stromal cell and IL7 dependent murine preB cells, the ecotropic retroviral packaging cell line GPE (Markowitz et al., *J. Virol.*, 62, p. 1120-1124, 1988) can be used, which routinely results in stable transduction of preB cells at efficiencies of 50-80%. This ecotropic packaging cell line in conjunction with (recombinant) retroviral transfer vectors will only produce replication deficient (recombinant) retroviruses able to transduce murine cells. For transient transfection of the ecotropic GPE packaging cell line, standard calcium phosphate transfection is used as detailed below:

(a) Transient Transfection of the Ecotropic Retroviral Packaging Cell Line GPE:

GPE cells are grown in IMDM-based low-serum medium also used for ST-2 and PA-6 stromal cells and described in example 1. One day prior to transfection, adherent GPE packaging cells are harvested by trypsinization and seeded at 50% confluency into fresh IMDM-based low-serum medium and cultivated at 37° C. in 10% $CO_2$. The following day, 20 µg retroviral DNA is transfected per T75 (75 $cm^2$) tissue culture flasks of GPE cells using standard calcium phosphate precipitation. 24 hours post transfection, the transfected GPE cells can be used for the transduction of recombinant retroviruses into preB cells.

(b) Retroviral Transduction of preB Cells Using Transfected GPE Cell Culture Supernatant or Coculture with Transfected GPE Cells:

Two methods can be used interchangably for the transduction of recombinant retroviruses produced by transfected GPE cells: The first method relies on the infection of preB cells with conditioned cell culture supernatant. For this, cell culture medium from transfected GPE cells is replaced 24 hours after transfection, and is harvested after another 24 hours of cell culture. The recombinant retrovirus containing cell culture supernatant is then added to cultures of proliferating preB cells at ratios of 1:8 (vol) to 1:1 (vol) in the presence of 8 µg/ml polybrene and incubation is continued for 3-6 hours at 37° C. Cells are then harvested, the polybrene/retrovirus containing medium is removed, and cells are plated at a density of $1-2\times10^5$ onto fresh, 3000rad γ-irradiated stromal cells in preB cell medium containing 100 U rIL7. Retrovirally transduced preB cells are then harvested 24 hours later.

The second method relies on the coculture of preB cells with transfected, recombinant retrovirus producing GPE cells. For this, log-phase preB cells are harvested and resuspended in fresh preB cell culture medium containing 100 U rIL7 and 8 g/ml polybrene at a density of $2-4\times10^5$ cells and are plated onto transfected GPE cells 24 hours post transfection with retroviral constructs. PreB cells are co-cultured for 6 hours at 37° C., they are then harvested and plated onto fresh, 3000rad γ-irradiated stromal cells in preB cell medium containing 100 U rIL7 for recovery. Retrovirally transduced preB cells are then harvested and can be utilized 24 hours later.

Example 5

Inactivation of Endogenous Immunoglobulin Heavy and Light Chain Gene loci in Long-Term Proliferating, Murine Precursor B Cells The first step for the generation of heterologous, preferably human antibodies from murine precursor B cells, is the inactivation of the endogenous, murine IgH and IgL, which can, among other methods, e.g. be accomplished by gene targeting within the immunoglobulin gene locus in preB cells. In theory, it would be required to inactivate all three murine immunoglobulin gene loci, i.e. the IgH, IgκL and IgλL chain gene loci. However, the murine λL chain gene locus comprises only three functional V-J-C clusters with one gene segment each and only very limited diversity is comprised in λL chains. Furthermore, less than 5% of murine B cells express λL chain gene loci. Therefore, in practical terms, it is sufficient to inactivate the endogenous, murine IgH and κL chain gene loci in order to assure that upon transfer of heterologous IgH and IgkL chain genes or gene loci, the vast majority of B cells (>95%) produced from preB cells will express heterologous antibodies.

(a) Isolation of preB Cells with Naturally Occuring Irreversibly Non-Functional IgH Alleles.

Generally, the most controlled way for inactivation of the endogenous IgH and κL chain gene loci is to use gene targeting (see below). However, in case of the IgH chain gene locus, another method can be applied:

Long-term proliferating, stromal cell IL7 dependent murine preB cells carry $DJ_H$ rearrangements on both of their heavy chain alleles. Due to imprecision in the D to $J_H$ joining process, these $DJ_H$ rearrangements may occur such that D gene segments can be read in all three possible reading frames relative to the fixed reading frame of the $J_H$ gene segment. These reading frames have arbitrarily been designated reading frames I, II and III (Kaartinen and Mäkelä, *Immunol. Today,* 6, p. 324-330, 1985). Most D gene segments contain stop codons, if a $DJ_H$ junction occurs in reading frame III (Kaartinen and Mäkelä, s.a.), such that a functional H chain can never be expressed from such a heavy chain allele.

Therefore, statistically roughly 1/9 (11.1%) of all stromal cell, IL7 dependent preB cells carry $DJ_H$ rearrangements in reading frame III with stop coding on both of their IgH chain alleles. These preB cells can be isolated by subcloning under limiting dilution conditions and screening for the desired non-functional rearrangements. To ensure the isolation of stable clones, rearrangements need to be screened for two non-functional $DJ_H4$ gene rearrangements, which cannot be reverted by secondary rearrangements because the last $J_H$ gene segment has been used up. Such clones can be used for further targeted inactivation of the κL chain alleles.

(b) Generation of Targeting Constructs for the Murine IgH and IgκL Chain Loci

Figure 5A:
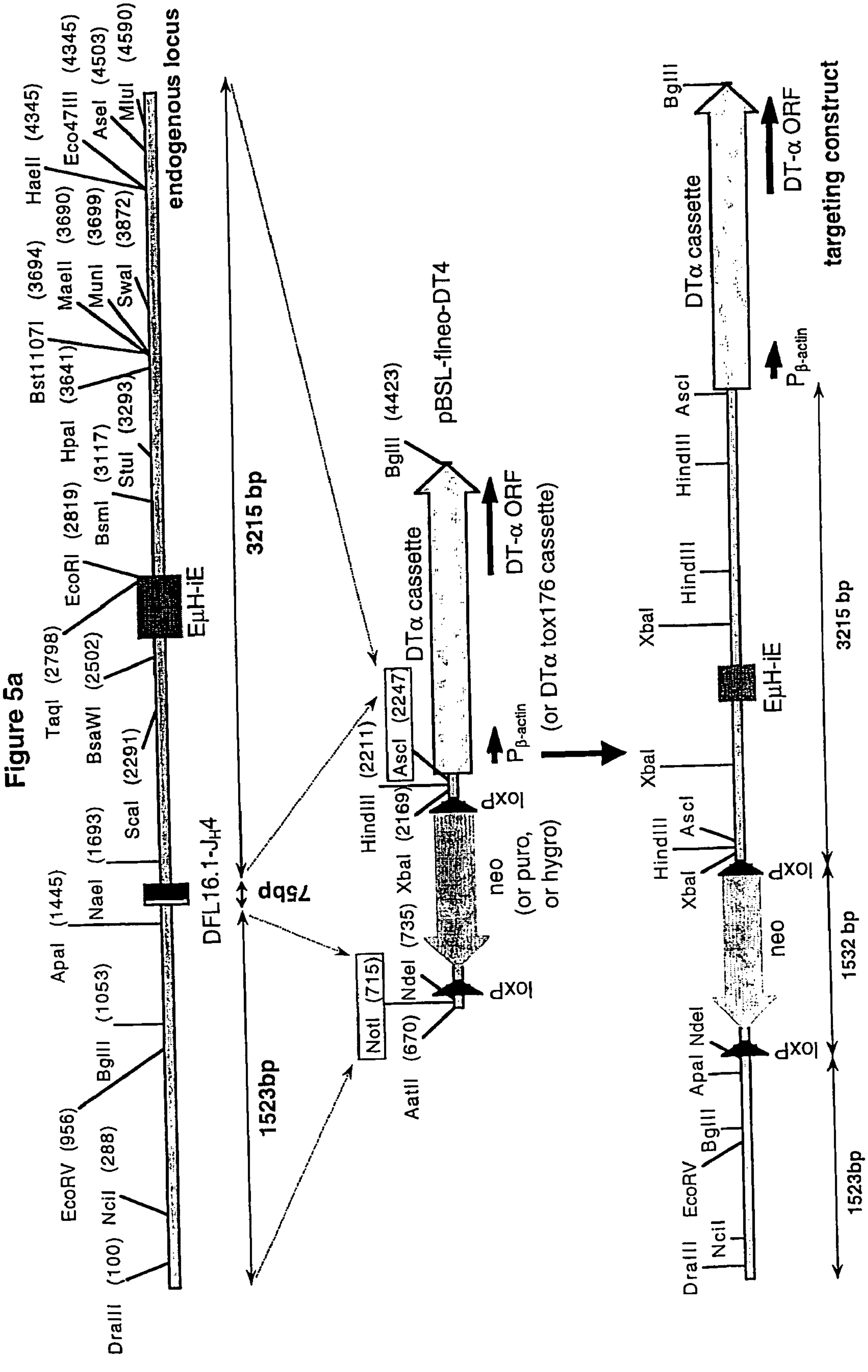
FIG. 5*a* illustrates the cloning strategy for the construction of an IgH chain gene locus targeting vector. The detailed cloning strategy for the construction of one possible targeting construct for $DJ_H$ rearranged murine IgH chain gene loci is depicted here at the example of a $D_{FL16.1}$-$J_H4$ rearranged gene locus. Other $DJ_H$ rearranged IgH chain gene loci can be targeted with the same targeting vector. Unique restriction sites are indicated in the endogenous gene locus (top construct) and the regions of 1523 and 3215 bp that are PCR cloned from genomic DNA into the empty positive-negative targeting vector pBSL-flneo-DT4 are indicated (see FIG. 6*b*, pBSL-flneo-DT4 was chosen as one example of various different empty targeting vectors). The PCR primers for the short and the long arms are designed to contain Not I and Asc I restriction sites for cloning of the fragments into the unique and compatible restriction sites in pBSL-flneo-DT4. The organisation of the final targeting construct is depicted on the bottom, and positions of selected restriction sites are indicated.

Two examples for methods resulting in gene targeted inactivation of both the endogenous IgH and IgκL chain gene loci are presented as examples for many cis-acting mutations that would similarity lead to preB cells without the potential to express endogenous IgH and IgκL chain proteins (FIGS. 5*a,b*). For both targeting strategies, first, empty positive-negative gene targeting vectors need to be constructed containing unique cloning sites allowing the insertion of DNA sequences homologous to the target gene locus, a positive drug selection marker, like neomycin or puromycin, flanked by loxP sites and a negative selection marker, like diphtheria toxin, or herpes simplex virus thymidine kinase (HSV-tk), which will select against random integration of the gene targeting vector into the genome of cells. The presence of a loxP flanked (floxed) positive selection marker will allow the sequential gene targeting of both alleles in the same cell clone using the same antibiotic, because, after successful targeting of the first allele, the antibiotic resistance marker can be deleted from cells upon transient expression of cre recombinase deleting any nucleotide sequence located in between the cognate loxP recognition sites. The empty positive-negative targeting vectors are constructed as follows (FIGS. 6*a,b*):

Step 1: Extending the Multiple Cloning Site of pBluescript SK(+)

Two complementary synthetic DNA oligomers:

```
SEQ ID NO. 11 (P007)
5'-TCGAccggtacctaggcgcgccatcgatatcgctagctcgagctcagatctGTAC-3'
and

SEQ ID NO. 12 (P008)
5'-agatctgagctcgagctagcgatatcgatggcgcgcctaggtaccgg-3'
```

are annealed by mixing 100 pmol of each oligomer in 50 μl of 50 mM Tris/HCl, 100 mM NaCl, pH8.0. The mixture is then denatured for 2 minutes at 95° C. and slowly cooled from 65° C. to room temperature within 20 min. This will generate the following double stranded DNA linker with XhoI and KpnI compatible overhangs (indicated in uppercase letters):

```
5'-TCGAccggtacctaggcgcgccatcgatatcgctagctcgagctcagatctGTAC-3'
       |||||||||||||||||||||||||||||||||||||||||||||||
   3'-ggccatggatccgcgcggtagctatagcgatcgagctcgagtctaga-5'
```

The annealed synthetic DNA linker is then ligated into XhoI-KpnI linearized commercially available pBluescriptSK (+) (Stratagene) resulting in plasmid pBSL containing an extended multiple cloning site (MCS+, see FIG. 6*a*) required for the following cloning steps.

Step 2: Insertion of Expression Cassettes for Wild-Type or Attenuated Diphtheria Toxin α as a Negative Selection Marker Against Random Integration of Targeting Constructs As a negative selection marker that allows selection against random chromosomal integration of gene targeting constructs, an expression cassette for diphtheria toxin a (McCarrick et al., s.a.), or its attenuated version, diphtheria toxin α (DT-αtox176) (Maxwell et al., s.a.), under control of a constitutive β-actin promoter can be used Although other negative selection markers, like the herpes simlex virus thymidine kinase gene (HSV-tk), is commonly used in gene targeting experiments with mouse embryonic stem cells, diphtheria toxin α and its attenuated mutant tox176 have been proven to be effective for gene targeting in somatic cells (Grawunder et al., *Mol. Cell,* 2, p. 477-484, 1998). The diphtheria toxin expression cassettes are isolated as 2.1 kb BglII-XbaI fragments from plasmids pBS-DT4 (SEQ ID NO. 2), or pBS-DT4tox176 (SEQ ID NO. 3; see FIG. 6*a*) and are ligated into BglII-NheI linearized pBSL resulting in plasmids pBSL-DT4 and pBSLDT4tox176, respectively (see FIG. 6*a*).

Step 3: Insertion of loxP Flanked Positive Drug Selection Markers into pBSL-DT4 and pBSLDT4tox176 for the Generation of Empty Gene Targeting Vectors The next step for the generation of positive/negative gene targeting vectors is the insertion of a positive drug selection marker into the pBSL-DT4 or pBSL-DT4-tox176 vector, upstream of the diphtheria expression cassette. As representative examples the insertion of loxP site flanked neomycin, puromycin and hygromycin B expression cassettes upstream of the diphtheria toxin α expression cassette in pBSL-DT4 are presented. However, it should be noted that identical cloning strategies can be applied to the pBSL-DT4tox176 vector, containing the attenuated version of diphtheria toxin α. Furthermore, other positive drug selection markers conferring resistance e.g. to histidinol, mycophenolic acid, bleomycin, or zeocin may be used.

In each case, the positive antibiotic selection marker cassette will be flanked by loxP sites, that can be recognized by the cre recombinase enzyme, and which can be used to delete the drug selection marker located between the loxP sites upon transient transfection of a cre recombinase expression vector, for sequential use of the same selection marker.

i) Insertion of a Floxed Neomycin Resistance Cassette:

A loxP site flanked neomycin resistance cassette can be isolated as a 1497 bp Bsp120I-XbaI digested DNA fragment from plasmid pGL2neo(m)+ (SEQ ID NO. 4) and can be ligated into NotI-XbaI linearized pBSL-DT4 to generate the empty targeting vector pBSL-flneo-DT4.

ii) Cloning of Floxed Puromycin and hygromycinB Cassettes (FIG. 6*b*):

Because floxed antibiotic selection markers other than neomycin are rarely found, an essential step for the insertion of loxP flanked puromycin or hygromycinB markers into pBSL-DT4 is the preparatory step of inserting two loxP sites. This can be achieved by inserting into pBSL-DT4 annealed synthetic DNA oligomers. The synthetic loxP sites are contained in the following two complementary DNA oligos:

```
SEQ ID NO. 13 (P009)
5'-CTAGATAACTTCGTATAGCATACATTATACGAAGTTATACGCGTATAACTTCGTATAGCATA
CATTATACGAAGTTAT-3'
and

SEQ ID NO. 14 (P010)
5'-CTAGATAACTTCGTATAATGTATGCTATACGAAGTTATACGCGTATAACTTCGTA
TAATGTATGCTATACGAAGTTAT-3'
```

These two DNA oligomers are annealed as described in example 5(b), step 1, resulting in a double stranded DNA fragment containing two loxP sites separated by a unique MluI restriction site. In addition, the annealed synthetic DNA oligomers contain two 5'-CTAG single-stranded overhangs, which can directly be ligated into compatible restriction site overhangs (generated e.g. by SpeI, NheI, XbaI, or AvrII restriction enzymes).

Figure 6B:
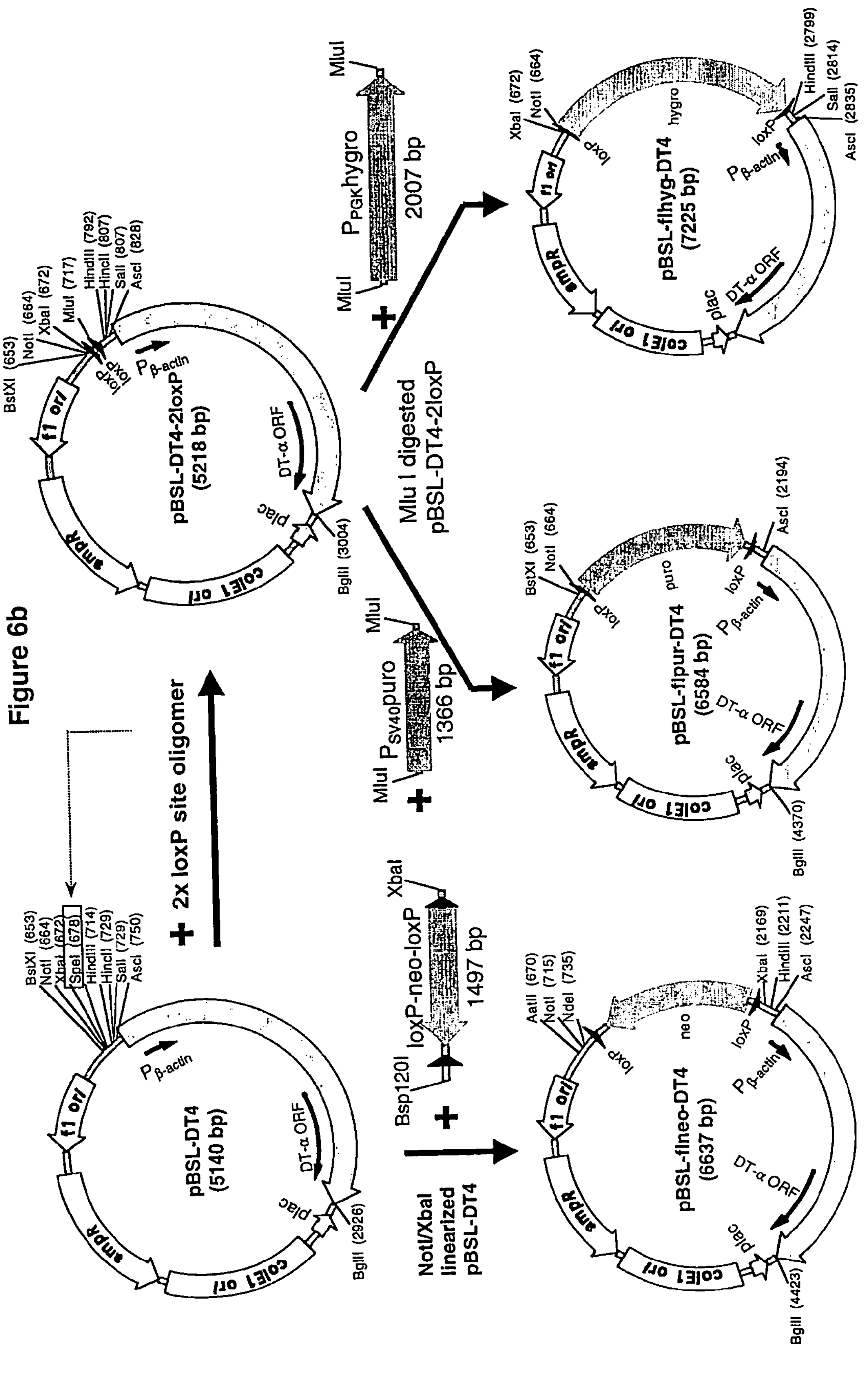
FIG. 6*b* illustrates the detailed cloning strategy for DT-α and DT-α(tox176) based positive-negative vectors for gene targeting (final cloning steps). Cloning of empty positive-negative targeting vectors containing either neomycin, hygromycinB, or puromycin as positive selection markers and a wild-type diphtheria toxin α expression cassette are described. The same cloning strategies can be used for vectors containing an expression cassette for DT-α(tox176) instead. Restriction enzymes used for cloning of fragments and linearization of constructs are indicated. All positive selection markers are designed to be flanked by loxP sites (floxed) which can be recognized by cre recombinase. While a floxed neomycin expression cassette can be recloned from the existing vector pGL2-neo(m)+ (DSM 14705), floxed hygromycinB and floxed puromycin expression cassettes needed to be inserted in two steps. For this, a synthetic DNA oligomer containing two loxP sites separated by a MluI site was inserted into pBSL-DT4 in order to generate pBSL-DT4-2loxP, as indicated. In a final step, expression cassettes for hygromycinB and puromycin resistance were PCR cloned into the unique MluI site of pBSL-DT4-2loxP.
Figure 7A:
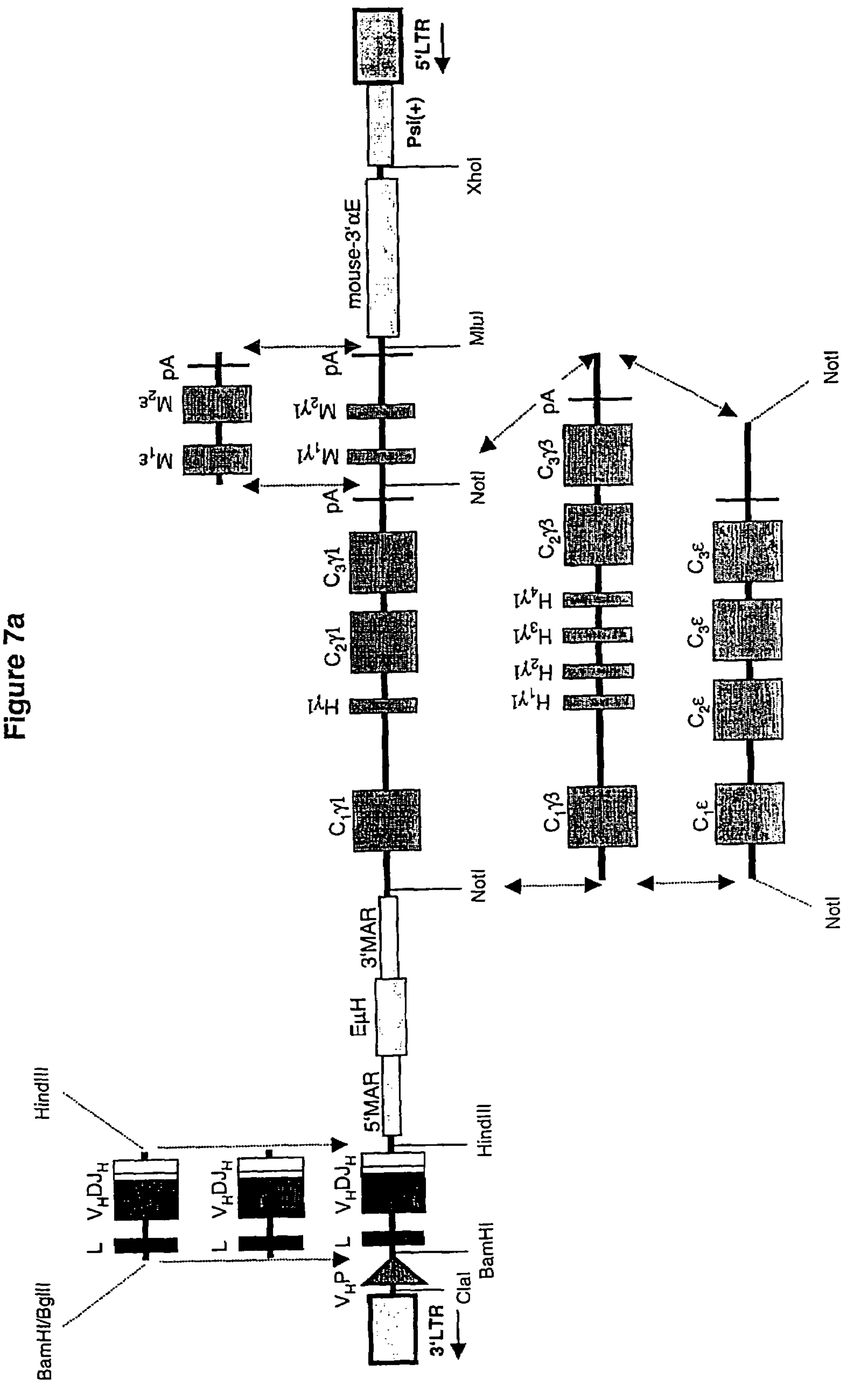
FIG. 7*a* shows the schematic organization of retroviral expression vectors for human IgH chains. Recombinant retroviral vectors allowing the expression of human IgH chain proteins exhibit a modular design containing Ig locus promoter and enhancer elements, as well as coding regions for the variable and constant region domains of IgH chains. The transcriptional orientation of the IgH expression cassette is opposite to the retroviral 5'LTR promoter element in order to confer a B cell specific expression pattern based on the Ig specific promoter and enhancer elements. The expression cassette contains a murine $V_H$ promoter a leader (L) sequence with VDJ exons encoding IgH variable domains, the murine intron heavy chain enhancer (EμH), exons encoding the constant regions of heterologous IgH chains, exons for the membrane spanning regions of immunoglobulins, and elements from the murine IgH 3'α enhancer. Different L-VDJ regions, and even libraries of L-VDJ regions may be cloned into the unique BamHI and HindIII restriction sites of the IgH expression vector using restriction enzymes generating compatible overhangs. Due to the modular design, constant region exons or enhancer elements may be replaced using simple molecular biology techniques (as indicated).
Figure 7B:
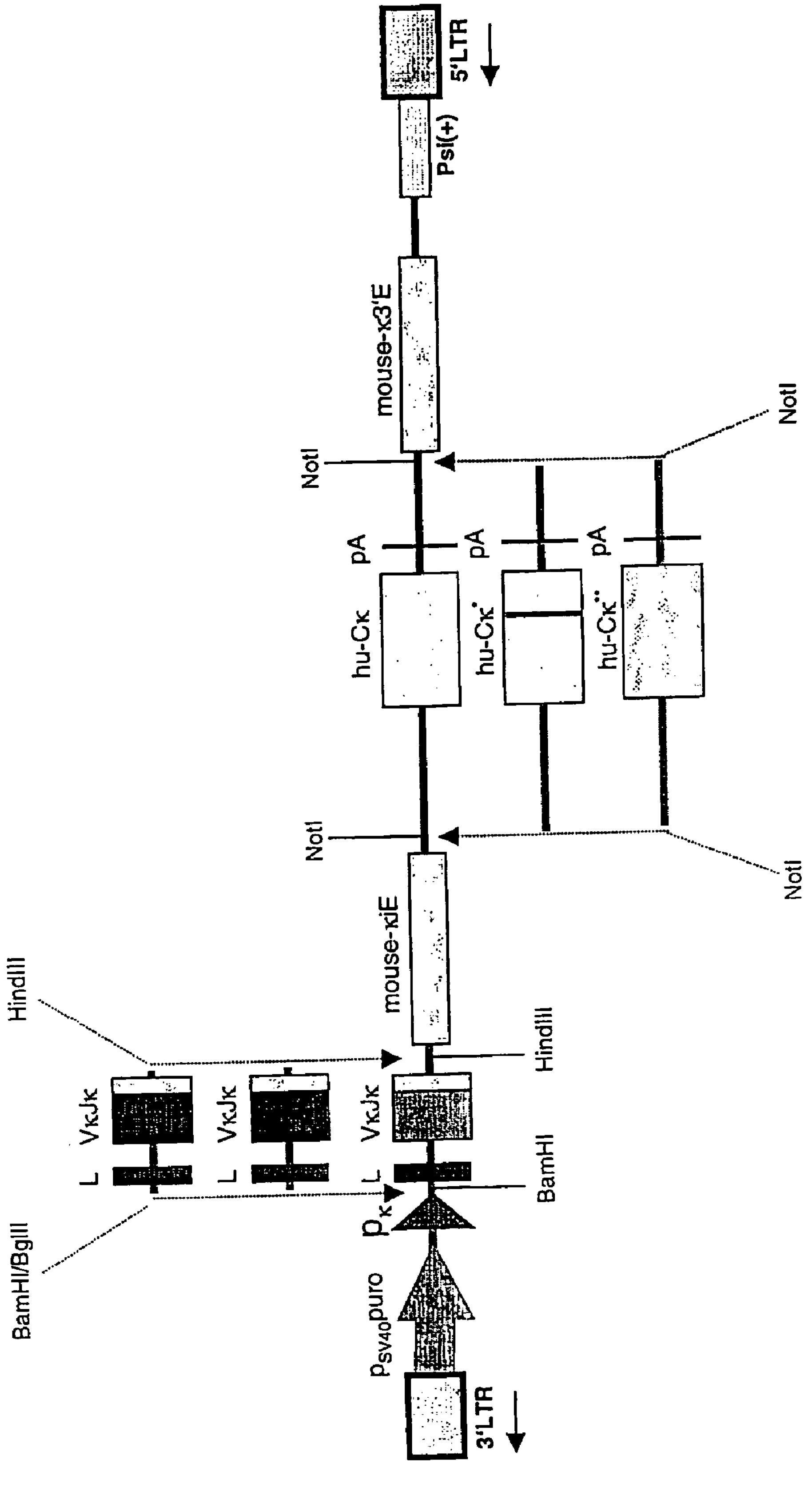
FIG. 7*b* shows the schematic organization of retroviral expression vectors for human IgκL chains. Like the vectors depicted in FIG. 7*a*, recombinant retroviral vectors allowing the expression of human IgκL chain proteins exhibit a similar modular design containing IgL chain specific locus promoter and enhancer elements, as well as coding regions for the variable and constant region domains of IgκL chains. The transcriptional orientation of the IgκL expression cassette is opposite to the retroviral 5'LTR promoter element, in order to confer a B cell specific expression pattern based on the Ig specific promoter and enhancer elements. The expression cassette contains a murine Vκ promoter, a leader (L) sequence with VJ exons encoding IgκL variable domains, the murine κ intron enhancer (κiE), exons encoding the constant region of heterologous IgL chains, and elements from the murine Ig κ3' enhancer (κ3'E), as indicated. In addition, retroviral IgκL chain expression vectors contain a complete puromycin expression cassette, allowing the selection of stably transduced preB cells. Different L-VJ regions, and even libraries of L-VJ regions may be cloned into the unique BamHI and HindIII restriction sites of the IgH expression vector using restriction enzymes generating compatible overhangs. Due to the modular design, modified constant region exons or enhancer elements may be replaced using simple molecular biology techniques (as indicated).

The annealed double loxP site containing DNA fragment is then ligated into SpeI linearized pBSL-DT4 resulting in vector pBSL-DT4-2loxP (FIG. 6*b*).

Expression cassettes for puromycin or hygromycinB resistance can be PCR amplified using plasmids pPur (Clontech) or pPGK-hygro (SEQ ID NO. 1) as PCR templates, respectively. The primers used for PCR amplification of the 1366 bp puromycin expression cassette from pPur (containing the puromycin ORF under control of the simian virus40 early promoter) are:

```
SEQ ID NO. 15 (P011)
5'-tcgACGCGTggaatgtgtgtcagttagggtgtggaaag-3'
and

SEQ ID NO. 16 (P012)
5'-tcgACGCGTttggacaaaccacaactagaatgcagtg-3'
```

Both primers contain recognition sites for the restriction endonuclease MluI (indicated in uppercase letters), such that the resulting PCR product can be cloned using this restriction enzyme.

After MluI digestion of the isolated PCR product the puromycin marker fragment is ligated into MluI linearized pBSL-DT4-2loxP generating the empty targeting vector pBSL-flpur-DT4 (FIG. 6*b*).

The primers used for PCR amplification of the 2007 bp hygromycin B expression cassette from pPGK-hygro (SEQ ID NO. 1; containing the hygromycinB ORF under control of the phospho glycerat kinase promoter) are:

```
SEQ ID NO. 17 (P013)
5'-tcgACGCGTgaattctaccgggtaggggaggcgcttttc-3'
and

SEQ ID NO. 18 (P014)
5'-tcgACGCGTggaattagaacttggcaaaacaatactgag-3'
```

Both primers contain recognition sites for the restriction endonuclease MluI (indicated in uppercase letters), such that the resulting PCR product can be digested and ligated using this restriction enzyme.

After MluI digestion of the isolated PCR product the hygromycinB marker fragment is ligated into MluI linearized pBSL-DT4-2loxP generating the empty targeting vector pBSL-flhyg-DT4 (FIG. 6*b*).

Step 4: Cloning of Final Targeting Vectors for Murine IgH and κL Chain Gene loci, as Well as for the RAG1 Gene As representative examples for cloning of targeting vectors for endogenous gene loci, the cloning strategies for gene targeting vectors useful for the cis-acting targeted mutation of the endogenous IgH and IgκL chain gene loci, and for the trans-acting mutation of the RAG1 gene in murine preB cells are described.

i) Construction of IgH Chain Targeting Vectors (FIG. 5*a*)

Inactivation of the endogenous murine IgH chain gene locus in preB cells can be achieved by generating many different cis-acting targeted deletions on both IgH chain alleles. One of IgH inactivating deletion is for instance the deletion of all $D_H$ and $J_H$ gene segments, which is described here as one of the possibilities to render the endogenous IgH alleles incapable of producing endogenous immunoglobulins. Targeting vector construction is presented here using a "floxed" neomycin targeting construct as an example (see FIG. 5*a*). For the cloning of gene targeting vectors containing other positive antibiotic selection marker, like e.g. puromycin or hygromycinB, similar strategies may be applied.

Stromal cell, IL7 dependent murine preB cells usually carry $DJ_H$ rearrangements on both alleles (see above). This fact needs to be taken into account for the design of targeting vectors. Regardless of the type of $DJ_H$ rearrangement, the DNA sequences intervening the variable gene segments and the D gene segment cluster, as well as the intervening sequences between the $J_H$ gene cluster and the Cμ coding region are still present on both IgH alleles in all preB cells. Targeting vectors for $DJ_H$ rearranged alleles therefore have to contain homology regions upstream of the most 5' located D element ($D_{FL16.1}$) and downstream of the most 3' located $J_H$ gene segment ($J_H4$).

The genomic organization of one possible $D_{FL16.1}$-$J_{H4}$ rearranged allele with surrounding genomic DNA sequences is depicted in FIG. 5*a*. As a general strategy for gene targeting, a short region of DNA sequence homology (1-1.5 kb) located upstream of the region or gene to be deleted is cloned into a unique restriction enzyme recognition site upstream of a "floxed" positive selection marker (here NotI), and a longer region of DNA sequence homology (>2.5 kb) located downstream of the region or gene to be deleted is cloned into a unique restriction enzyme recognition site located between the "floxed" positive selection marker and the diphtheria toxin α expression cassette (FIG. 5*a*) (here AscI). Expression of the negative selection marker (diphtheria toxin α) is therefore only prevented, if homologous recombination occurs in the long region of DNA sequence homology of the targeting vector and the endogenous gene locus, such that the DT-α expression cassette will be lost upon targeted integration of the targeting vector into the chromosomal DNA. If homologous recombination further occurs in the short homology arm, the region located between the double crossover will be replaced by the positive drug selection marker. Thus using antibiotic selection on preB cells transfected with the targeting construct results in strong selection for the targeted integration of the targeting vector by homologous recombination resulting in the deletion of the endogenous gene locus.

A short region of homology upstream of the most 5' located D element ($D_{FL16.1}$) can be PCR amplified from mouse genomic DNA using the following primers designed based on the published NCBI-Genbank sequence AF018146:

```
SEQ ID NO. 19 (P015)
5'-aatGCGGCCGCgaacctcctgtgttgcaagcacaaatggg-3',
and

SEQ ID NO. 20 (P016)
5'-aatGCGGCCGaggcagcacggttgagtttcagttgtcatc-3'
```

Nucleotides of the appended NotI restriction enzyme recognition sites introduced for cloning purposes are indicated in uppercase letters. The primers will amplify a 1465 bp genomic PCR fragment that can be digested with NotI restriction enzyme and ligated into NotI linearized pBSL-flneo-DT4 generating pBSL-5'$J_H$-flneo-DT4 (FIG. 5*a*). The long region of sequence homology downstream of the $J_H$ gene segment cluster, also comprising the EμH heavy chain intron enhancer, can be PCR amplified from mouse genomic DNA using the following primers designed based on published NCBI-Genbank sequence file J00440 (nucleotides of the appended AscI restriction enzyme recognition site are indicated in uppercase letters):

```
SEQ ID NO. 21 (P017)
5'-ttGGCGCGCCgtaagaatggcctctccaggtctttatttt-3'
and

SEQ ID NO. 22 (P018)
5'-ttGGCGCGCCagctcagctcagctcaccccagctcagctc-3'
```

Figure 5B:
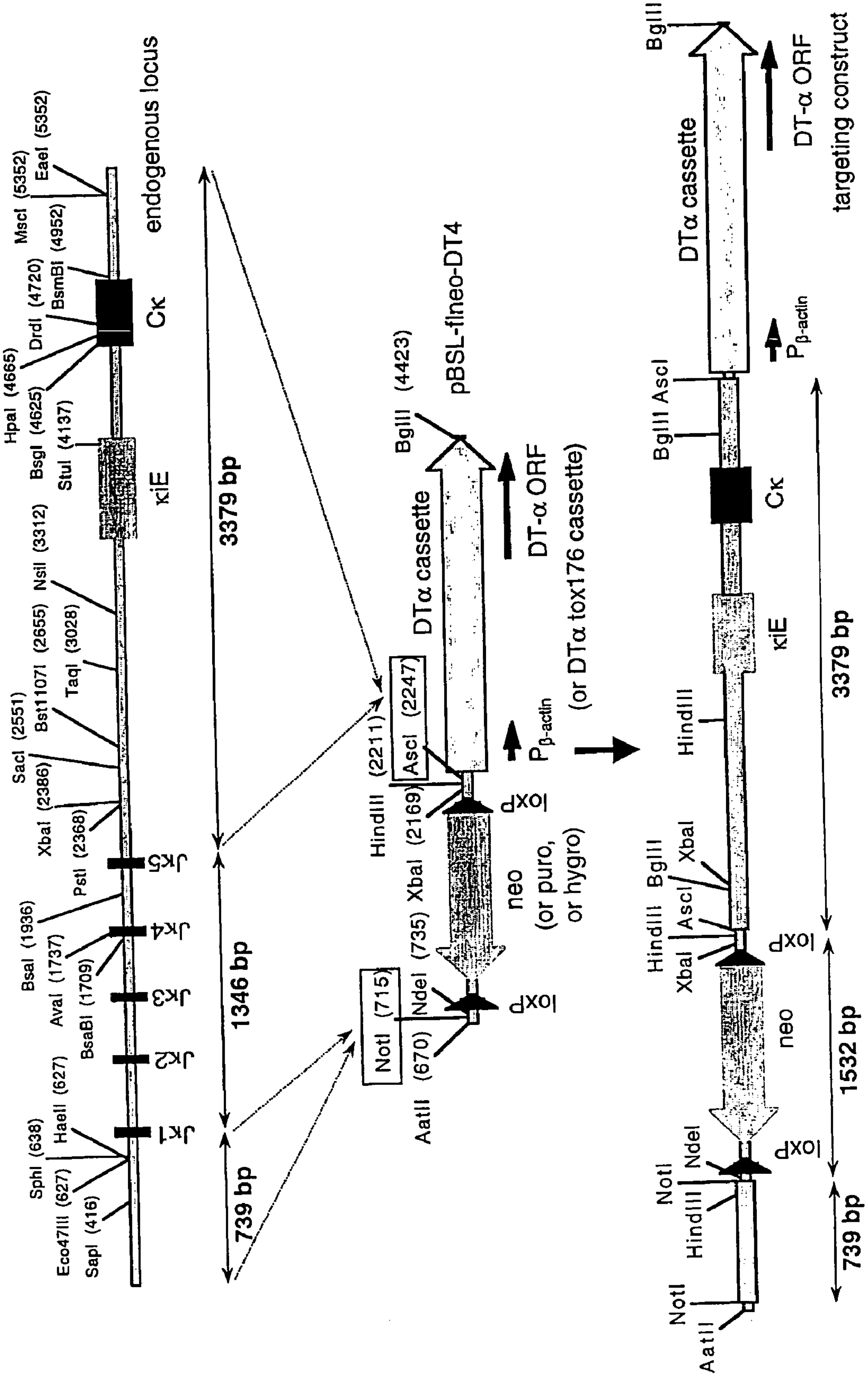
FIG. 5*b* illustrates the cloning strategy for the construction of an IgκL chain gene locus targeting vector. The detailed cloning strategy for the construction of one possible targeting construct for murine IgκL chain gene loci designed for the targeted deletion of all germline Jκ gene segments is depicted here. Unique restriction sites are indicated in the endogenous gene locus (top construct) and the regions of 739 and 3379 bp that are PCR cloned from genomic DNA into the empty positive-negative targeting vector pBSL-flneo-DT4 are indicated (see FIG. 6*b*, pBSL-flneo-DT4 was chosen as one example of various different empty targeting vectors). As in FIG. 5*a*, PCR primers for the short and the long arms are designed to contain Not I and Asc I restriction sites for cloning of the short and long arms into compatible restriction sites of pBSL-flneo-DT4. The organisation of the final targeting construct is depicted on the bottom, and positions of selected restriction sites are indicated.

The primers will PCR amplify a 3215 bp genomic PCR fragment from mouse genomic DNA that can be digested with AscI restriction enzyme and ligated into AscI linearized pBSL-5'$J_H$-flneo-DT4 generating the final $J_H$ targeting vector pBSL-5'$J_H$-flneo-3'$J_H$-DT4 that can be used to delete all remaining $D_H$ and $J_H$ gene segments in $DJ_H$ rearranged preB cells (FIG. 5*a*).

ii) Construction of κL Chain Targeting Vectors (FIG. 5*b*)

Like in the case of the IgH chain locus, the κL chain gene loci may be inactivated by several cis-acting mutations, including e.g. deletions of all of the $J_κ$ gene segments, the κL chain intron enhancer (κiE), the constant κL chain region ($C_κ$), or the 3'κ enhancer (3'κE). As an example, targeting constructs and methods are described here that can be used for the targeted deletion of all of the $J_κ$ gene segments. Furthermore, construction of targeting constructs described herein is presented only for targeting constructs containing a "floxed" neomycin resistance marker. Cloning of targeting constructs containing "floxed" puromycin or hygromycinB expression cassettes are performed in analogous fashion. A short region of homology upstream of the $J_κ$ gene segment cluster is PCR amplified from mouse genomic DNA using the following primers designed according to published NCBI-Genbank entry V00777 (nucleotides of the appended NotI restriction enzyme recognition site used for cloning purposes are printed in uppercase letters):

```
SEQ ID NO. 23 (P019)
5'-tatGCGGCCGCttatctttctcctttattaacggttgctg-3'
and

SEQ ID NO. 24 (P020)
5'-tatGCGGCCGCacagtggtagtactccactgtctggctg-3'
```

Primer P019 binds to position 1-30 and primer P020 to position 711-738 of NCBI-Genbank entry V00777. The resulting 738 bp PCR fragment is digested with NotI restriction enzyme and is ligated into NotI linearized empty targeting vector pBSL-flneo-DT4 generating pBSL-5'$J_κ$-flneo-DT4 (FIG. 5*b*). The long region of DNA sequence homology downstream of the $J_κ$ gene segment cluster comprising the κiE and the constant kL chain region (Ck) is PCR amplified from mouse genomic DNA using the following primers designed based on published NCBI-Genbank entry V00777 (nucleotides of the appended AscI restriction enzyme recognition site are printed in uppercase letters):

SEQ ID NO. 25 (P021)
5'-ttGGCGCGCCtgtgtaagacacaggttttcatgttaggag-3'
and

SEQ ID NO. 26 (P022)
5'-ttGGCGCGCCtgcttcgccaagtttactgggtaggttg-3'

Primer P021 will bind to position 2129-2158, and primer P022 to position 5456-5483 of NCBI-Genbank sequence V00777. The resulting 3379 bp PCR fragment is digested with AscI restriction enzyme and is ligated into AscI linearized vector pBSL-5'$J_\kappa$-flneo-DT4 generating pBSL-5'$J_\kappa$-flneo-3'$J_\kappa$-DT4 (FIG. 5*b*).

iii) Generation of a RAG Locus Targeting Vector (FIG. 5*c*):

As an alternative to inactivating the potential of preB cell to express endogenous immunoglobulins by introducing cis-acting mutations within the IgH and IgκL chain gene loci, preB cells can also be rendered incapable for rearrangement of their endogenous Ig genes, by introducing trans-acting mutations. This can for instance be achieved by targeting one of the two recombination activating (RAG) genes that are essential for Ig gene rearrangements. Murine preB cells with deletions in either the RAG-1, or the RAG-2 gene will be unable to rearrange immunoglobulin gene segments and are therefore unable to express endogenous immunoglobulins.

As an example, the construction of a targeting vector is described allowing the complete deletion of the ORF of the RAG-1 gene. A short arm of DNA sequence homology of about 1 kb of genomic sequence upstream of the RAG-1 coding region is amplified by the following primer pair designed based on published NCBI-Genbank sequence AC084753:

SEQ ID NO. 27 (P023)
5'-tataGCGGCCGCttctgctcctcttctttagtactggattc-3'
and

SEQ ID NO. 28 (P024)
5'-tataGCGGCCGCgttggctaagctacctgggaacaatggggg-3'

Figure 5C:
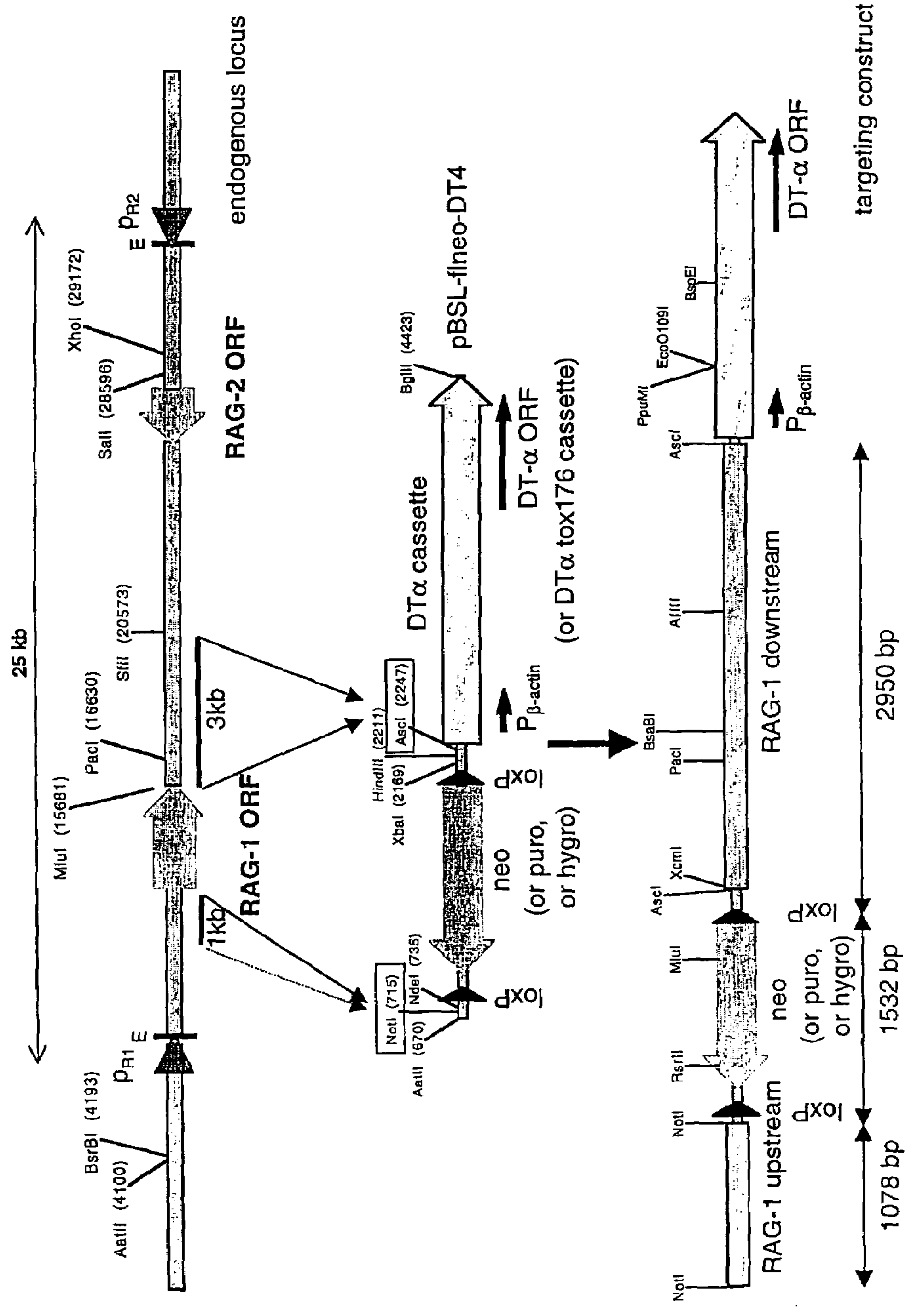
FIG. 5*c* illustrates the cloning strategy for the construction of a RAG gene locus targeting vector. The detailed cloning strategy for the construction of one possible targeting construct for the murine RAG gene locus designed for the targeted deletion of the RAG-1 gene is depicted here. The RAG gene locus in the mouse is located on chromosome 2 and contains the two very closely linked genes, RAG-1 and RAG-2, that are each essential for Ig gene rearrangements. The open reading frames (ORFs) of both genes are encoded by one single exon, but a short untranslated exon downstream of each promoter element (indicated by triangles) is spliced to one large exon containing the entire RAG ORFs. Unique restriction sites are indicated in the endogenous gene locus (top construct). Genomic regions of 1078 and of 2950 bp up and downstream of the RAG-1 ORF, respectively, are PCR cloned from genomic DNA into the empty positive-negative targeting vector pBSL-flneo-DT4, as indicated (see FIG. 6*b* for pBSL-flneo-DT4, which was chosen as one example of various different empty targeting vectors). As in FIG. 5*a*, PCR primers for the short and the long arms are designed to contain Not I and Asc I restriction sites for cloning of the short and long arms into compatible restriction sites of pBSL-flneo-DT4. The organisation of the final targeting construct is depicted on the bottom, and positions of selected restriction sites are indicated.

NotI cloning sites appended to the 5' end of each primer are highlighted in uppercase letters and are used for the cloning of a 1095 bp PCR fragment containing the genomic region upstream of the RAG-1 open reading frame (FIG. 5*c*). The PCR product is digested with NotI and ligated into the unique NotI site of a positive-negative targeting vector, e.g. pBSL-flneo-DT4. A plasmid clone containing the short arm of homology upstream of the RAG-1 coding region in correct orientation is isolated and designated pBSL-5'R1-flneo-DT4.

For the cloning of the long arm of a targeting construct for the RAG-1 gene, a genomic region of approximately 3 kb directly downstream of the RAG-1 coding region (FIG. 5*c*) is amplified by the following primer pair, designed based on Genbank sequence AC084753:

SEQ ID NO. 29 (P025)
5'-ttGGCGCGCCataggatctccacatagaagttggtatttgcc-3'
and

SEQ ID NO. 30 (P026)
5'-ttGGCGCGCCgtgggcacacatatgtcatcccagttaccc-3'

Recognition sequences for the AscI restriction enzyme are appended to the 5' end of each primer and are used for the cloning of the 2954 bp long PCR fragment containing the long arm of DNA sequence homogy downstream of the RAG-1 open reading frame. After AscI digestion, this PCR product is cloned into the unique AscI restriction site of the vector pBSL-5'R1-flneo-DT4. A plasmid clone containing the long arm of homology downstream of the RAG-1 coding region in the correct orientation is isolated and designated as pBSL-5'R1-flneo-3'R1-DT4 (FIG. 5*c*) and can be directly used for the targeted deletion of the endogenous RAG-1 gene in preB cells.

Step 5: Targeting of Endogenous Gene Loci in Long-Term Proliferating, Stromal Cell, IL7 Dependent Murine preB Cells For the sequential targeted deletion of both alleles of an endogenous gene locus, two different strategies can be applied. One strategy is to utilize targeting vectors with two different positive selection markers for the targeting of the two different alleles. Alternatively, another strategy is to use the same targeting construct twice for the sequential targeting of both endogenous alleles. However, in case of the latter strategy targeting of the first allele has to be followed by the transient expression of an expression vector for cre-recombinase into preB cells, which will lead to the permanent deletion of the loxP site flanked drug selection marker, such that the same antibiotic drug selection may be used for the second targeting of the other allele.

As an example, the experimental procedure for the sequential targeting of both alleles of an endogenous gene according to the first strategy, i.e. using targeting vectors with two different antibiotic resistance markers (puromycin and hygromycinB) is described.

For targeting of a gene locus on the first allele, 20 μg of linearized targeting vector with a puromycin resistance marker is transfected into $10^7$ preB cells resuspended in PBS by electroporation at 350V with 960 μF capacitance using a BioRad electroporator and a 0.4 cm electroporator cuvette. The cells are then plated in IL7 growth medium at a density of $5\times10^4$ cells/well into 96well plate cultures coated with a subconfluent layer of 3000 rad irradiated puromycin resistant ST-2 stromal cells. 30 hours post transfection puromycin is added at a final concentration of 2 μg/ml. Puromycin resistant colonies are isolated 7-10 days post transfection and expanded on fresh, irradiated and puromycin resistant ST-2 stromal cells under continued selection with 2 μg/ml puromycin. Individual puromycin resistant preB cell clones are analyzed for the targeted integration of the targeting vector into one allele by standard PCR and genomic southern blot hybridization analysis. PreB cell clones with a targeted integration of the targeting vector on one allele are again transfected, this time with 20 μg of linearized targeting vector containing a hygromycinB resistance marker under the same conditions as described above. Transfected preB cells are then plated in IL7 growth medium at a density of $5\times10^4$ cells/well into 96well plate cultures coated with a subconfluent layer of 3000 rad irradiated puromycin and hygromycinB double resistant ST-2 stromal cells. Double resistant preB cell clones are selected 30 hours post transfection by addition of 2 μg/ml puromycin and 400 μg/ml hygromycinB. Puromycin and hygromycin B double resistant colonies are isolated 7-10 days post transfection and expanded on fresh, irradiated and puromycin/hygromycinB double resistant ST-2 stromal cells under continued selection with 2 μg/ml puromycin and 400 μg/ml hygromycinB. Individual puromycin/hygromycinB double resistant preB cell clones are analyzed for the targeted integration of the targeting vector into the second allele again by standard genomic PCR and/or southern blot analysis.

Puromycin/hygromycinB double resistant preB cell clones with two targeted alleles may then transiently be transfected with a constitutive cre-recombinase expression vector in order to repeat gene targeting experiments on other gene loci and alleles. This can be done by transiently transfecting preB cells with 20 μg of supercoiled cre-recombinase expression vector by electroporation as described above. The transiently transfected cells are then plated under limiting dilution conditions in IL-7 growth medium into several 96 well plates onto 3000 rad irradiated, subconfluent ST-2 stromal cells. After 7 days of culture a set of 48 clones is replica plated onto normal ST-2 stromal cells for continued culture, and onto either puromycin resistant or hygromycinB single resistant ST-2 cells und the respective selection. Previously puromycin/hygromycinB double resistant preB cell clones that became sensitive two both antibiotic drugs have likely undergone cre-recombinase mediated deletion of both loxP flanked resistance markers. Once the cre-recombinase mediated deletion of the two resistance markers has been verified by southern blot analyses, the clones can be subjected to the additional gene targeting procedures for other endogenous gene loci and alleles.

Example 6

Construction of Retroviral Expression Constructs for Human Immuno-Globulin Polypeptides In order to re-program murine stromal cell, IL7 dependent preB cells for the production of human immunoglobulins, novel retroviral expression vectors encoding human antibody polypeptides can be used. Methods for the generation of recombinant retroviral vectors are described that allow the regulated expression of human IgH and L chain proteins, depending on the B cell differentiation stage, first as membrane-bound and later as secreted immunoglobulins. It should be noted that any type of heterologous binding protein can be cloned into these retroviral vectors allowing the expression of any type of heterologous and human binding protein. The description of the cloning of retroviral transfer vectors for the expression of human IgH and IgL chains described herein, should therefore only be viewed by way of illistration and not by way of exclusion. Recombinant retroviral vectors can accommodate up 7-10 kb of heterologous DNA sequences, which requires the design of separate constructs for IgH and L chain glycoproteins including all the required cell-type and differentiation stage specific promoter, enhancer and control elements, as well as endogenous Ig gene splice signals. These control elements are necessary to ensure proper expression, membrane deposition and secretion of immunoglobulins, their affinity maturation, in the various B cell differentiation stages, as well as high level secretion of heterologous antibodies in plasma cells. Individual retroviral constructs for IgH and L chains can be co-transduced into preB cells upon which the constructs stably integrate into the genome of the infected preB cells. If murine preB cells are used which are deprived of the potential express endogenous immunoglobulins (see description above), then only heterologous or human antibodies or binding proteins will be expressed in B lineage cells upon differentiation of the retrovirally transduced preB cells.

(a) Generation of Retroviral Constructs for the Regulated Expression of IgH Chains Because the retroviral constructs for the various IgH and L chain proteins will eventually be transduced into murine cells, the promoter and enhancer elements controlling Ig expression will be from murine origin in order to ascertain optimal interactions with B lineage specific murine transcription factors.

Figure 12A:
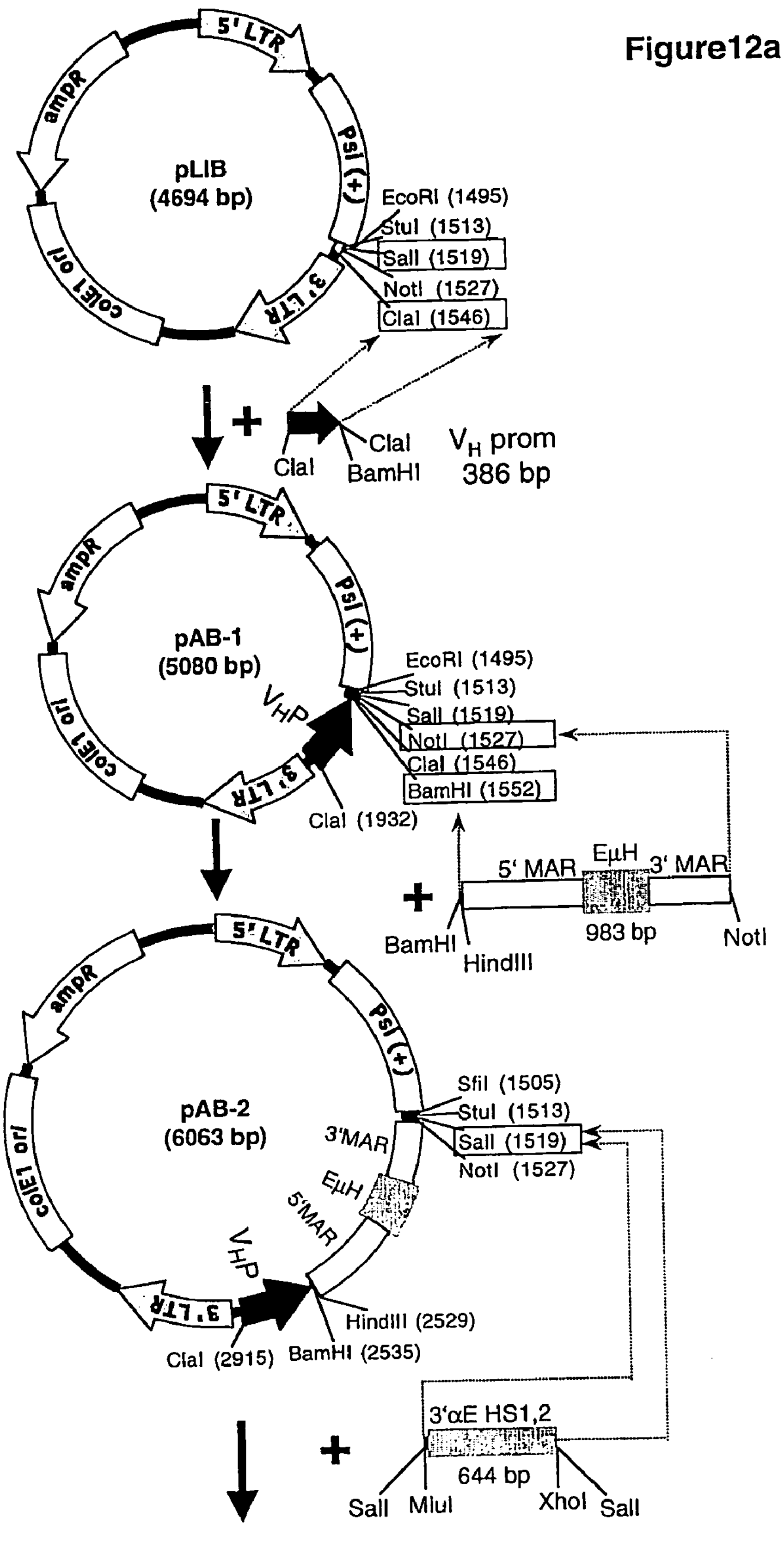
FIG. 12*a* examplifies the construction of retroviral expression vectors for the expression of human IgH chains (preparatory step I). The various IgH promoter and enhancer elements, as well as the coding regions for the different variable and constant region domains, are sequentially cloned into a retroviral transfer vector, like e.g. plasmid pLIB. This plasmid contains all elements required for retroviral packaging and provirus integration, i.e. a 5' LTR, a packaging signal, and a 3' LTR, cloned into a bacterial, ampicillin selectable plasmid backbone with a ColE1 origin of replication (as indicated). Depicted here are the first cloning steps for inserting a $V_H$promoter, the murine heavy chain intron enhancer (EμH), including flanking matrix attachmant regions (MAR) and the IgH chain 3'α enhancer (3'αE). Restriction enzymes incorporated at the termini of PCR amplified fragments, as well as unique compatible restriction enzyme sites in the plasmid backbone, which can be used in the various cloning steps, are highlighted.

The starting vector from which the retroviral expression constructs are generated is the empty retroviral cloning vector pLIB (Clontech) (FIG. 12*a*). The generation of a recombinant retroviral expression vector for human immunoglobulin heavy chains is a multistep cloning process, which involves the sequential cloning of promoter and enhancer elements, as well as the coding regions for the various variable and constant regions of human antibodies into the empty retroviral cloning vector pLIB. In a first step, a murine $V_H$ promoter is PCR cloned into the unique ClaI restriction site of the multiple cloning site of pLIB. This is done by PCR amplification of a mouse $V_H$ promoter element from mouse genomic DNA using the following primers designed based on the published NCBI-Genbank database accession number X71119.

```
SEQ ID NO. 31 (P027)
5'-ccATCGATtgactggatgcttgttaattctaataag-3',
and

SEQ ID NO. 32 (P028)
5'-ccATCGATGGATCCtgtgtgccagtaactgtagagagaac-3'
```

These primers will PCR amplifiy a 394 bp $V_H$ promoter fragment which will contain restriction enzyme recognition sites for ClaI (ATCGAT) at their 5' and 3' ends, because they are incorporated at the 5' ends of primers P027 and P028. In addition to ClaI sites in both primers, the reverse primer P028 contains an additional BamHI restriction site (GGATCC, underlined) introducing another unique restriction site into the PCR product (see FIG. 12*a*), which will be required for further cloning steps. After ClaI restriction enzyme digestion of the PCR fragment, the amplified $V_H$ promoter PCR fragment including the novel BamHI site is ligated into ClaI linearized pLIB vector. Ligation products containing the $V_H$ promoter in the desired orientation (opposite to the transcriptional orientation of the 5'LTR promoter) are identified by diagnostic restriction enzyme digestions and DNA sequencing and are designated pAB-1 (FIG. 12*a*).

The second step is the cloning of the murine intron heavy chain enhancer (EμH) with its flanking matrix attachment regions (MARs) into retroviral vector pAB-1. The EμH enhancer element with its flanking (MARs) is known to be required for the efficient expression of immunoglobulin proteins in B lineage cells. The cloning of the EμH enhancer element is performed by amplifying a 983 bp PCR fragment from mouse genomic DNA using the following primers designed according to published NCBI-Genbank sequence J00440:

```
SEQ ID NO. 33 (P029)
5'-cgGGATCCAAGCTTagagaggtctggtggagcctgcaaaagtcc-3'
and

SEQ ID NO. 34 (P030)
5'-
gatcGCGGCCGCtctagataattgcattcatttaaaaaaaaatatttc-
3'
```

Restriction sites (BamHI/HindIII for P029 and NotI for P030) appended to the 5' end each primer are highlighted in uppercase letters. The PCR product can then be digested with BamHI and NotI restriction enzymes and is directionally ligated into BamHI/NotI linearized retroviral vector pAB1, resulting in vector pAB-2. The sense primer P029 contains the sequence for an additional HindIII site (underlined), which will give rise to a unique restriction enzyme recognition site in pAB-2, required for later cloning steps.

Next, a DNA fragment containing the murine 3'α enhancer is added to the construct pAB-2. The 3'α enhancer is known to be required for optimal and high level expression and secretion of antibodies at the differentiation stage of plasma cells. The 3'α enhancer is known to contain four DNAseI hypersensitivity sites (HS1, HS2, HS3, and HS4) that comprises various binding sites for late B cell/plasma cell specific transcription factors. In reporter gene assays, it was shown that HS1 and 2, which are located within a 0.6 kb genomic DNA fragment, confer at least 80% of the 3'α enhancer activity with little contribution of HS3 and 4 that are highly homologous in DNA sequence.

All four 3'α enhancer components, HS1, 2, 3 and 4, constitute a so-called locus control region (LCR), which is able to regulate the transcriptional activity of a given gene locus independently of flanking DNA sequences. A basic retroviral expression vector for immunoglobulin heavy chains should therefore at least contain the HS1,2 regions of the 3'α enhancer which can be PCR amplified from mouse genomic DNA using primers designed according to the published NCBI-Genbank sequence entry X96607 (recognition sequences for additional restriction enzyme sites required for the cloning of the PCR fragment or later cloning steps are highlighted in uppercase letters):

```
SEQ ID NO. 35 (P031)
5'-
gcatGTCGACACGCGTgggggctcagatatcagtaccagaaacaagg-
3',
and

SEQ ID NO. 36 (P032)
5'-cgatGTCGACCTCGAGttggagtcacaggcctgtctccatgtgg-3'
```

Figure 12B:
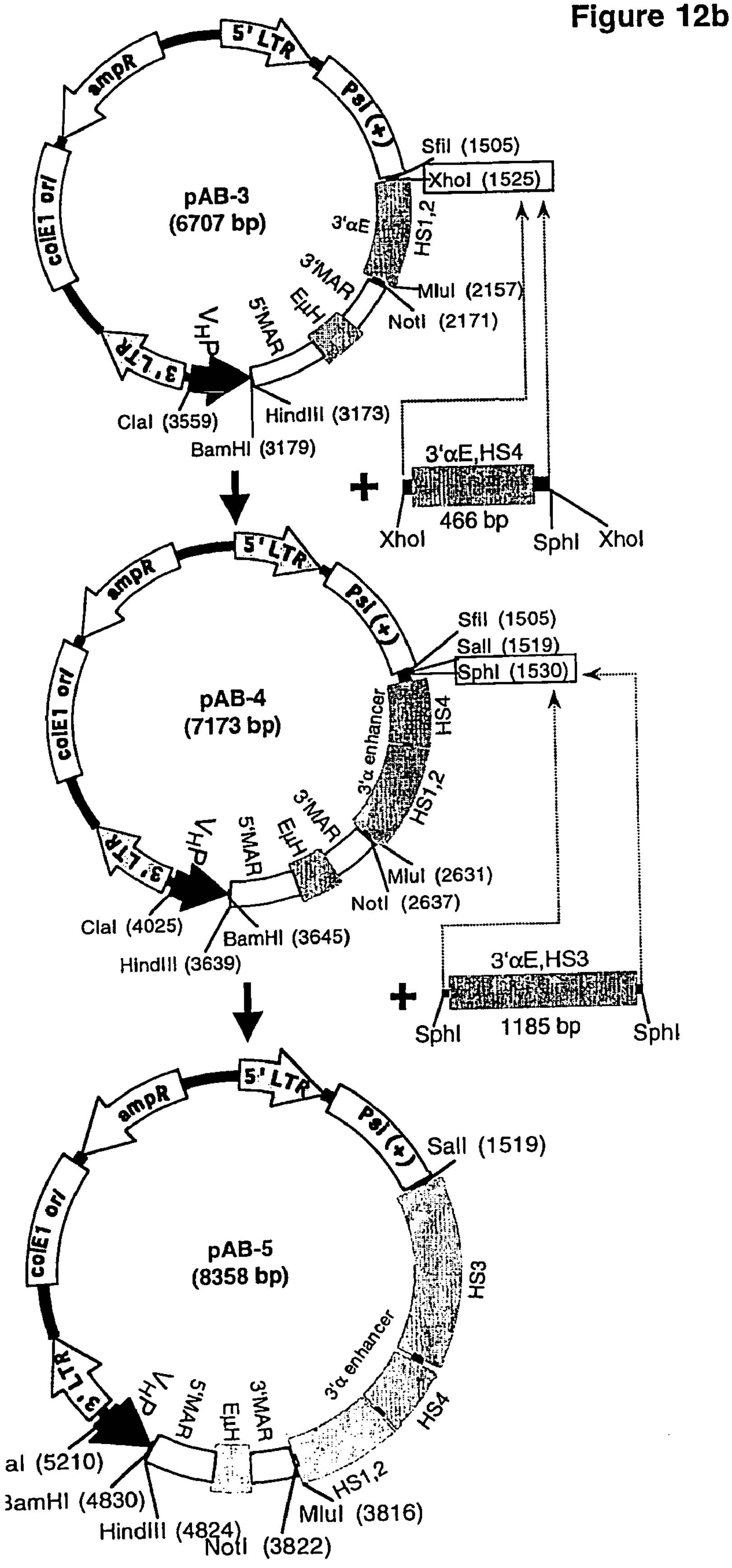
FIG. 12*b* exemplifies the construction of retroviral expression vectors for the expression of human IgH chains (preparatory step II). The IgH 3'α enhancer contains four functional regions, which upon activation of the enhancer during terminal B cell differentiation become sensitive to DNaseI digestion and are therefore referred to as hypersensitive regions HS 1, 2, 3, and 4. Each of these HS regions contributes to the enhancer activity of the 3'αE, but most of the enhancer activity is conferred by the HS1,2 regions. Although the HS1,2 region of the 3'αE alone is able to drive reporter gene expression to almost the same levels as the entire 3'αE region, it may be desirable for some retroviral IgH expression constructs to include the other functional regions of the 3'αE. Therefore, the cloning of the HS3 and HS4 regions of the 3'αE is depicted here. Restriction enzymes incorporated at the termini of genomic PCR fragments, as well as compatible restriction enzyme sites in the plasmid backbone, which can be used in the various cloning steps, are highlighted.

In addition to 5' terminal SalI sites (GTCGAC) in each of the primers, the sense primer P031 contains an additional MluI site (underlined) and the reverse primer P028 contains an additional XhoI site (underlined). Primers P031 and P032 will amplify a 644 bp PCR fragment that can be digested with SalI restriction enzyme and ligated into SalI linearized vector pAB-2. A clone with the insert in the desired orientation (see FIG. 12*b*) is determined by diagnostic restriction enzyme digestion and DNA sequencing, and is designated pAB-3 (FIG. 12*b*).

Optionally, the further 3'α enhancer components HS3 and 4 can be included in the retroviral vector constructs for IgH expression. For this a 466 bp fragment comprising the 3'α enhancer HS4 region can be PCR amplified from mouse genomic DNA as a template using the following primers designed according to published NCBI-Genbank sequence entry S74166:

```
SEQ ID NO. 37 (P033)
5'-gcaCTCGAGgggtagatgcagcctgtgttccgtttactg-3',
and

SEQ ID NO. 38 (P034)
5'-gctCTCGAGCATGCctgagcccaccaggaagtcctctgtg-3'
```

Restriction enzyme sites appended to the 5' termini of each primer are highlighted in uppercase letters. In addition to XhoI restriction sites (CTCGAG) present in both primers, the reverse primer P034 contains an additional SphI restriction site (GCATGC, underlined) containing an additional unique restriction site required for later cloning purposes. PCR amplification with primer pair P033 and P034 on genomic mouse DNA will result in a 466 bp PCR fragment that can be digested with the restriction enzyme XhoI and which is then ligated into XhoI linearized vector pAB-3. A clone with the HS4 insert in the desired orientation is determined by diagnostic restriction enzyme digestion and DNA sequencing, and is designated as vector construct pAB-4 (FIG. 12*b*).

The last 3'α enhancer fragment, HS3, can be PCR amplified using mouse genomic DNA as a template with the following primers designed according to published NCBI-Genbank sequence entry X96607 (recognition sequences for the restriction enzyme SphI are again highlighted in uppercase letters):

```
SEQ ID NO. 39 (P035)
5'-ttaaGCATGCaaccacatgcgatctaagggatattgggg-3'
and

SEQ ID NO.40 (P036)
5'-ttaaGCATGCgatcattgagctccggctctaacaactggg-3'
```

The PCR amplified HS3 3'α enhancer region is digested with SphI restriction enzyme and ligated into SphI linearized vector pAB-4 in order to generate pAB-5. Any of the vectors pAB-3, 4, or 5 can be used for inserting the coding regions for heterologous immunoglobulin heavy chains (FIG. 12*b*).

Each of the human immunoglobulin isotypes can be expressed as a membrane bound surface immunoglobulin or as a secreted antibody, which is regulated by alternative splicing events either maintaining or deleting the membrane spanning exons from the mRNA transcript. Although each immunoglobulin isotype has its own coding region for the membrane spanning exons, the membrane regions of all human IgG, IgA and IgE antibodies are virtually identical for the individual subtypes. Therefore, the same IgG membrane exons can be employed for membrane anchoring IgG1, IgG2, IgG3 and IgG4 antibodies, a different set of exons are used for both IgA1 and IgA2, and each different exons are required for each IgE and IgM antibodies.

Figure 12C:
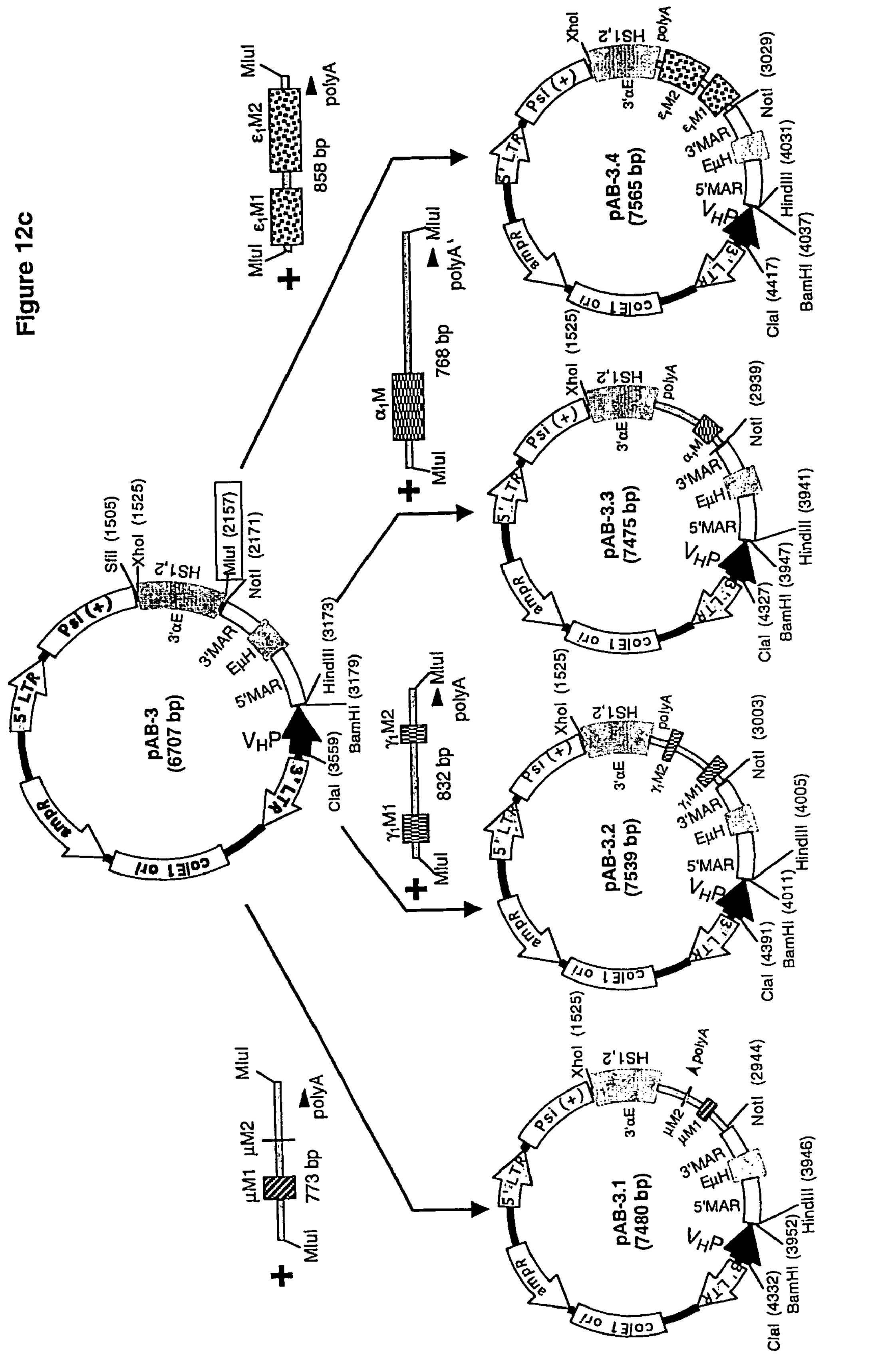
FIG. 12*c* shows the construction of retroviral expression vectors for the expression of human IgH chains (preparatory step III). Following the cloning of IgH promoter and enhancer elements into a retroviral transfer vector, coding regions for IgH chains need to be inserted. In order to be able to express membrane bound, as well as secreted forms of immunoglobulins, exons for the membrane spanning regions of IgH chains need to be included in the retroviral expression vectors. The membrane spanning regions differ significantly between different isotypes in length, primary sequence and exon/intron structure. Therefore, different membrane spanning regions for IgM, IgG, IgA and IgE heavy chains need to be cloned. As an example, the PCR cloning and insertion of the four respective different membrane spanning regions into plasmid pAB-3 is depicted. The same cloning procedures can be performed with vectors pAB-4 and pAB5, containing extended versions of the IgH 3'αE. Restriction enzymes incorporated at the termini of genomic PCR fragments, as well as compatible restriction enzyme sites in the plasmid backbone, which can be used in the various cloning steps, are highlighted.

Therefore, the next step in the cloning procedure towards the generation of recombinant retroviral Ig expression constructs is the insertion of the various membrane spanning regions for human IgG, IgA, IgM and IgE antibodies into any of the vectors pAB-3, 4, or 5. As a representative example, the further cloning procedures are described for the basic retroviral construct pAB-3 containing the $V_H$promoter, the EμH enhancer and the minimal 3'αE enhancer (HS1,2) elements (FIG. 12*c*).

The μH chain membrane spanning region is encoded by two exons, μM1 and μM2, located 1.85 kb downstream of the $C_\mu H$ constant region exons $C_\mu H_1$-$C_\mu H_4$. The μM1 and μM2 exons including the endogenous polyadenylation site are contained within a genomic fragment of 773 bp that can be amplified from mouse genomic DNA by PCR using the following primers designed based on published NCBI-Genbank contig sequence NT_010168:

```
SEQ ID NO. 41 (P037)
5'-catACGCGTcgctgcatcaggctttcaggggcccagccc-3'
and

SEQ ID NO. 42 (P038)
5'-catACGCGTccctcaccagaaagcagtttcatggataaaatg-3'
```

The MluI restriction sites appended to the 5' end of each primer are highlighted in uppercase letters. The resulting PCR product can be digested with MluI restriction enzyme and the resulting 773 bp fragment is ligated into MluI linearized vector pAB-3. A clone containing the μM1 and μM2 exons in correct orientation and DNA sequence as verified restriction enzyme mapping and by DNA sequencing is designated construct pAB-3.1 (FIG. 12*c*).

Membrane deposition of IgG antibodies can e.g. be accomplished by the membrane spanning exons of the $IgG_1$ gene. The $IgG_1$ membrane spanning region is encoded by two exons located 1.25 kb downstream of the $C_{\gamma 1}H$ exons spanning a region of 1.9 kb. In order to shorten the intron between γ1M1 and γ1M2, a single overlap extension (SOE) PCR approach is used, by which the two exons are fused to a smaller PCR fragment. Generally, the fusion of two PCR products can be achieved, if the reverse primer of the upstream PCR product and the sense primer of the downstream PCR product exhibit roughly 30-40 bp of complementarity. These regions of perfect complementarity can be appended as 15-20 nucleotides to the 5' ends of the reverse primer and forward primers used for the amplification of the upstream and the downstream PCR products, respectively. However, in case of the fusion of the two γ1M1 and γ1M2 exons, by coincidence, two completely identical sequences of 28 bp are present 78 bp downstream of γ1M1 and 256 bp upstream of γ1M2 exon. These sequences can be used to generate a shorter PCR fragment by SOE-PCR containing both the γ1M1 and γ1M2 exons for the membrane spanning region of γH chains. Therefore, two PCRs are performed in parallel on human genomic DNA using the following primers designed based on the published NCBI-Genbank sequence AL122127. A PCR fragment of 315 basepairs containing the γ1 membrane spanning exon 1 (γ1M1) is amplified from human genomic DNA using primers:

```
SEQ ID NO. 43 (P039)
5'-catACGCGTacagagggaatcacccccagaggcccaagccc-3'
and

SEQ ID NO. 44 (P040)
5'-gacagcgtcagggacaggtggggacagc-3',
```

with primer P039 binding to position 9710-9741, and primer P040 binding to position 9435-9462 of NCBI-Genbank sequence entry AL122127.

A 555 basepair PCR fragment containing the membrane spanning exon 2 (γ1M2) can be amplified from human genomic DNA using primers:

```
SEQ ID NO. 45 (P041)
5'-gctgtccccacctgtccctgacgctgtc-3',
and

SEQ ID NO. 46 (P042)
5'-
catACGCGTttatttggaaggggggcgtgtcaggtgtgtcagggtc-3'
```

with primer P041 binding to position 8137-8164, and primer P042 binding to position 7624-7654 of NCBI-Genbank sequence entry AL122127. The two PCR products can then be fused to a 822 bp PCR fusion product by mixing 1/100 of the γ1M1 exon PCR product with 1/100 of the γ1M2 exon PCR product and repeating a PCR with sense and reverse primers P039 and P042. In addition to MluI restriction enzyme recognition sites present in both primers P039 and P042 (highlighted in uppercase letters), which are required for the cloning of the SOE fusion PCR product, primer P042 additionally contains the complementary sequence of an artificial polyadenylation signal (underlined) allowing correct transcriptional termination of the immunoglobulin transcript in the final retroviral immunoglobulin expression vector. The 832 bp γ1M1γ1M2-polyA signal PCR fragment is then digested with MluI restriction enzyme and is ligated into vector pAB-3. A clone with the correct orientation of the insert verified by restriction enzyme mapping and DNA sequencing is designated clone pAB-3.2 (FIG. 12*c*).

Cloning of the α1 membrane spanning coding region can be achieved by PCR amplifying from human genomic DNA a fragment containing the single exon for α1M including its endogenous polyA site. The following primers can used for this PCR amplification, designed according to the published NCBI-Genbank sequence entry M60193:

```
SEQ ID NO. 47 (P043)
5'-atcACGCGTctcaggccttagatggggacccagaccc-3'
and

SEQ ID NO. 48 (P044)
5'-attACGCGTgacccccgtctcctcattcagagtctgtg-3'
```

Both primers contained MluI cloning sites appended to the 5' end of each primer (highlighted in uppercase letters) and will amplify a PCR product of 768 basepairs that can be digested with MluI restriction enzyme that is then ligated into MluI linearized pAB-3. A clone with correct orientation of the insert verified by restriction enzyme mapping and DNA sequencing is designated clone pAB-3.3.

For the expression of membrane bound IgE antibodies the membrane spanning region for $\epsilon_1H$ chains, which is encoded by two exons, $\epsilon_1M1$ and $\epsilon_1M2$ is PCR cloned. For this a 858 bp PCR product is amplified from human genomic DNA using the following primers designed according to published NCBI-Genbank sequence entry X63693:

```
SEQ ID NO. 49 (P045)
5'-catACGCGtcgggacctgggtgcccaccctcagggctgg-3'
and

SEQ ID NO. 50 (P046)
5'-
aatACGCGTttatttgtgccctgggctgggtgccgggccctccttgg-3'
```

Both primers contain MluI cloning sites appended to the 5' end of each primer (highlighted in uppercase letters) resulting in a 858 bp PCR product that can be digested with MluI restriction enzyme. In addition, the reverse primer P046 is designed to contain the complementary sequence of an artificial polyA signal (underlined) ensuring proper termination of mRNA transcription in the final expression construct. The MluI digested PCR fragment is ligated into MluI linearized pAB-3. A clone with correct orientation of the insert verified by restriction enzyme mapping and DNA sequencing is designated clone pAB-3.4.

Following cloning of the various membrane spanning exons for IgG, IgA, IgM and IgE isotypes, the exons for the various human constant regions have to be inserted into retroviral constructs pAB-3.1 to 3.4. For this, DNA fragments encoding the constant region exons are cloned into the unique NotI restriction enzyme recognition site of each of the pAB-3.1 to 4 constructs.

Figure 12D:
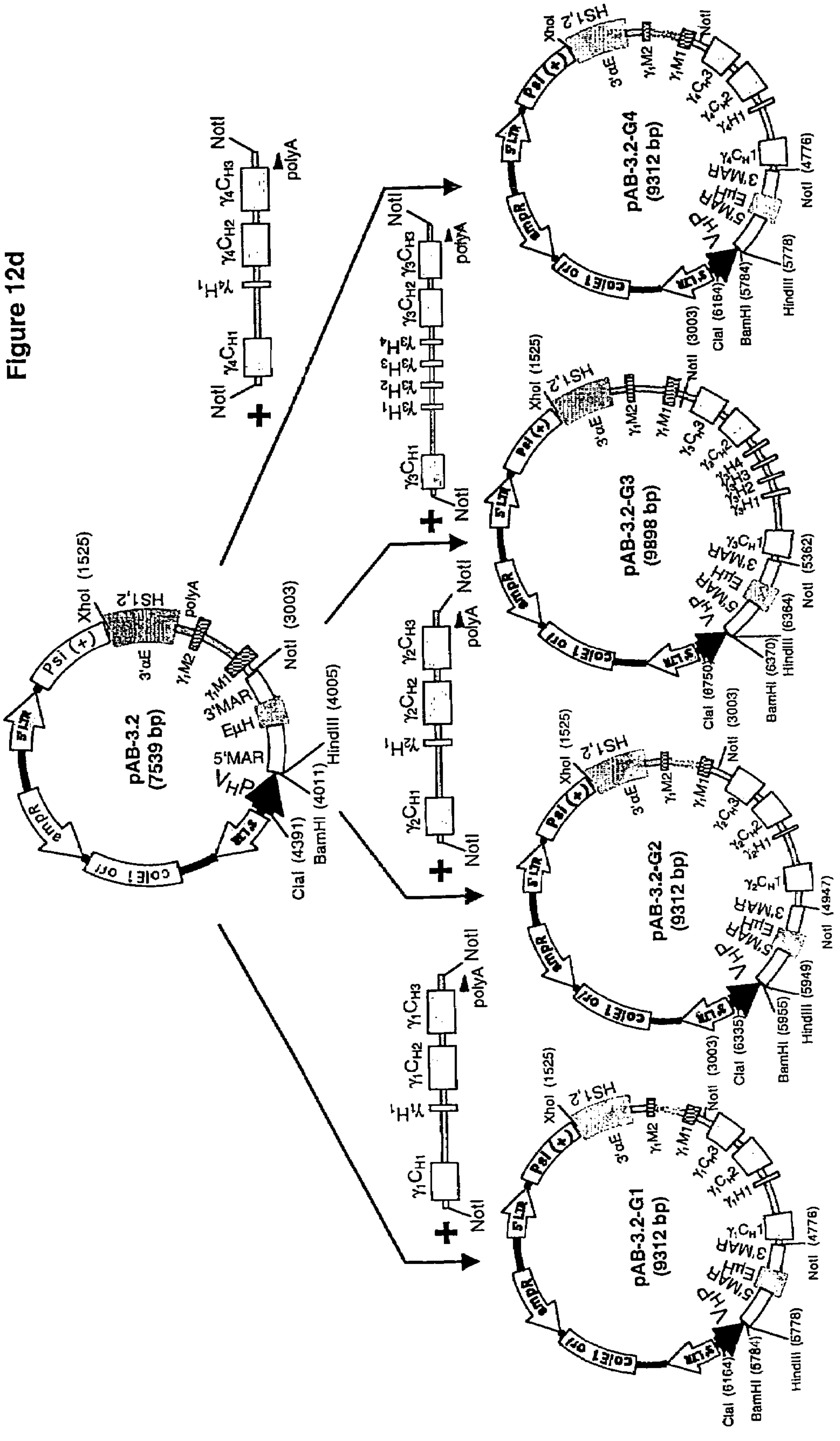
FIG. 12*d* illustrates the construction of retroviral expression vectors for the expression of human IgH chains (preparatory step IV). Human B lymphocytes are able to produce four different IgG isotypes, IgG1, IgG2, IgG3, and IgG4, that differ slightly in sequence and that exhibit different physiologic effector functions. The cloning of the constant region genes into an intermediate vector pAB-3.2, already containing IgG membrane spanning exons, is depicted here. The endogenous exon/intron organisation including the exons encoding the hinge (H) regions for the various IgG isotypes is indicated. Restriction enzymes incorporated at the termini of genomic PCR fragments, as well as unique compatible restriction enzyme sites in the plasmid backbone, which can be used in the various cloning steps, are indicated. Upon cloning of a VDJ rearranged variable domain exon, these constructs are capable of expressing complete IgG chains (see FIG. 15).

Cloning of retroviral expression vectors for all immunoglobulin H chain isotypes, γ1, γ2, γ3 and γ4 is depicted in FIG. 12*d*. The following primers can be used for the PCR amplification of the four different IgG heavy chain subtypes using human genomic DNA as a PCR template:

For γ1 (primers designed according to published NCBI-Genbank sequence AL122127):

SEQ ID NO. 51 (P047)
5'-gcatGCGGCCGCcctgggcccagctctgtcccacacc-3',
and

SEQ ID NO. 52 (P048)
5'-gcatGCGGCCGCtgggtgctttatttccatgctgggtg-3'

For γ2 (primers designed according to published NCBI-Genbank sequence J00230):

SEQ ID NO. 53 (P049)
5'-tataGCGGCCGCagggagtgggctaaggtgaggcaggtgg-3'
and

SEQ ID NO. 54 (P050)
5'-attaGCGGCCGCctcagactcggcctgacccacggaaagaac-3'

For γ3 (primers designed according to published NCBI-Genbank sequence AL122127):

SEQ ID NO. 55 (P051)
5'-gcatGCGGCCGCccagctctgtcccacaccgcagtcacatgg-3'
and

SEQ ID NO. 56 (P052)
5'-gctaGCGGCCGCtcgcaggggcccagggcagcgctgggtgctt-3'

For γ4 (primers designed according to published NCBI-Genbank sequence K01316):

SEQ ID NO. 57 (P053)
5'-attaGCGGCCGCggatagacaagaaccgaggggcctctg-3'
and

SEQ ID NO. 58 (P054)
5'-taatGCGGCCGCccagggcagtggtgggtgctttatttcc-3'

In each case, the PCR products of 1788 bp for $\gamma_1$H, of 1959 bp for $\gamma_2$H, of 2374 bp for $\gamma_3$H, and of 1820 bp for $\gamma_4$H can be digested with NotI restriction enzyme, upon which the digested fragment is ligated into NotI linearized pAB-3.2 (FIG. 12*d*). Constructs containing the inserts in correct orientation and without any mutations as determined by restriction enzyme mapping and DNA sequencing are designated pAB-3.2-G1, pAB-3.2-G2, pAB-3.2-G3, and pAB-3.2-G4, respectively.

Figure 12E:
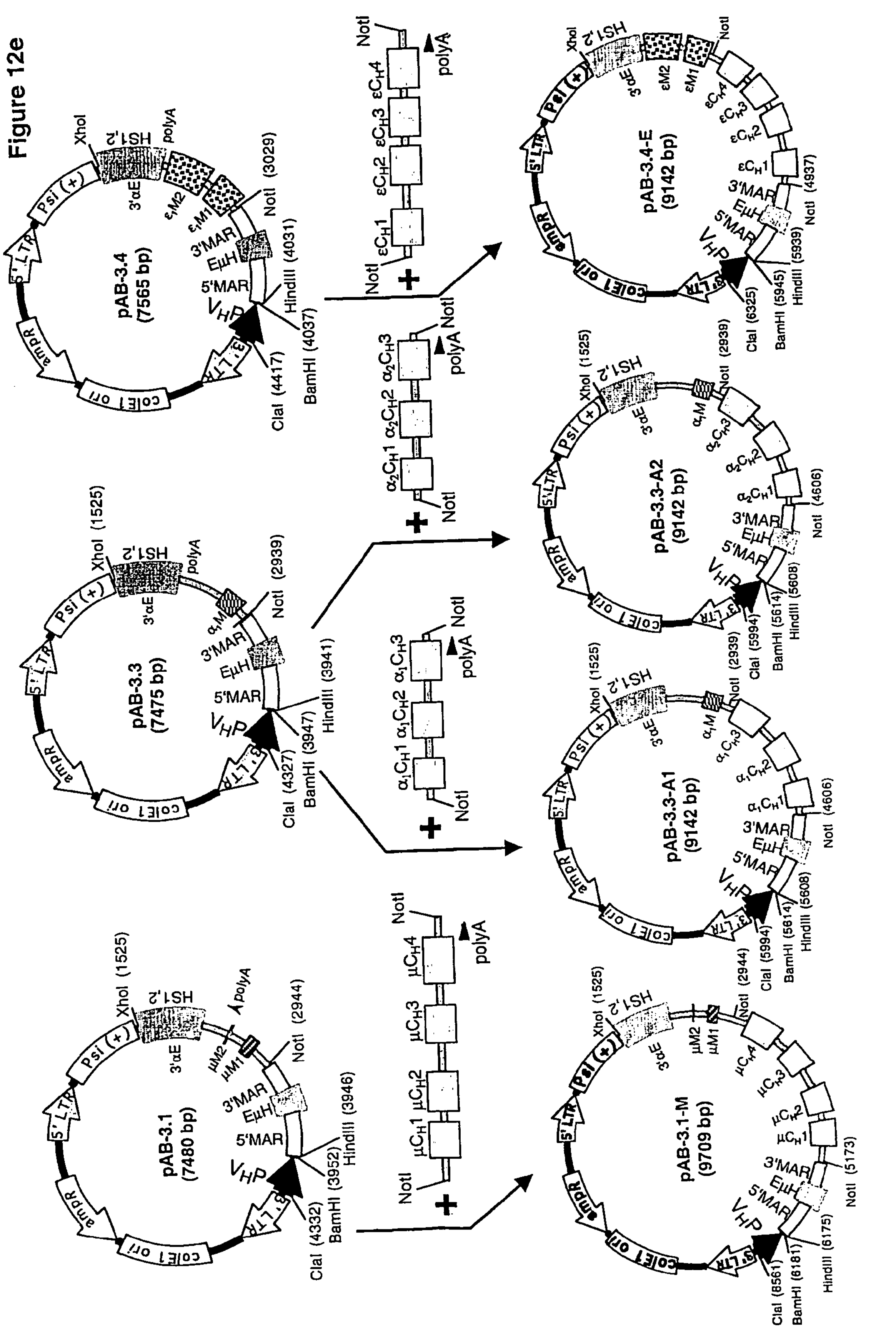
FIG. 12*e* shows the construction of retroviral expression vectors for the expression of human IgH chains (preparatory step V). The cloning of constant region genes for the remaining human Ig isotypes IgM, IgA1, IgA2, and IgE is depicted here. Similar to the cloning procedure for IgG constant region genes, depicted in FIG. 12*d*, the genomic regions for these isotypes are inserted as NotI digested PCR fragments into unique NotI restriction sites upstream of the respective membrane spanning exons for these isotypes. The endogenous exon/intron organisation including the exons encoding the hinge (H) regions for the various Ig isotypes is indicated. Restriction enzymes incorporated at the termini of genomic PCR fragments, as well as unique compatible restriction enzyme sites in the plasmid backbone, which can be used in the various cloning steps, are indicated. Upon cloning of a VDJ rearranged variable domain exon, these constructs are capable of expressing complete IgH chains of the respective isotype (see FIG. 15).

For the cloning of the constant region exons encoding μH, α1H, α2H, and ϵH chains, identical method are employed (FIG. 12*e*). The following primers are used for the PCR amplification of the different IgH isotypes using human genomic DNA as a template:

For μH (primers designed according to published NCBI-Genbank sequence AB019441):

SEQ ID NO. 59 (P055)
5'-attaGCGGCCGCcaccccagtaggccagagcatcgtgcac-3'
and

SEQ ID NO. 60 (P056)
5'-taatGCGGCCGCcacccctgatagccatgacagtctggg-3'

For $\alpha_1$H and $\alpha_2$H (primers designed according to published NCBI-Genbank sequences J00220, and J00221):

SEQ ID NO. 61 (P057)
5'-attaGCGGCCGCtgtcaccaggcctctctgtgctgggttcc-3'
and

SEQ ID NO. 62 (P058)
5'-tattGCGGCCGCcggatggaagcgtggggctgcttgggg-3'

For ϵH (primers designed according to published NCBI-Genbank sequence L00022):

SEQ ID NO. 63 (P059)
5'-taatGCGGCCGCcacggggtccccagctcccccatccagg-3'
and

SEQ ID NO. 64 (P060)
5'-atatGCGGCCGCtcccaagaatgggtgtactggggctc-3'

In each case, the PCR products of 2229 bp for μH, of 1667 bp for $\alpha_1$H and $\alpha_2$H, and of 1908 bp for ϵH can be digested with NotI restriction enzyme and can be ligated into NotI linearized pAB-3.1, pAB-3.3, and pAB-3.4, respectively (FIG. 12*e*). Constructs containing the inserts in correct orientation and without any mutations as determined by restriction enzyme mapping and DNA sequencing are designated pAB-3.1-M, pAB-3.3-A1, pAB-3.3-A2, and pAB-3.4-E, respectively.

The different retroviral H chain expression constructs controlled by natural IgH chain promoter and enhancer elements still require the insertion of a variable domain coding region, which will be presented after the description of the methods for cloning of the retroviral IgL chain expression vectors, because similar strategies for expressing unique or diverse specificities will be presented for both the complete retroviral IgH and IgL chain expression constructs.

(b) Generation of Retroviral Constructs for the Regulated Expression of IgκL Chains Similarly to the constructs designed for IgH chain expression, retroviral constructs designed for the differentiation stage specific expression of IgκL chains require the presence of defined κL chain locus specific promoter and enhancer elements. These include a $V_\kappa$ promoter, the κ light chain intron enhancer (κiE), and the κ3' enhancer (κ3'E) elements. The sequential cloning of these elements can be accomplished as follows (FIG. 13 *a,b*).

A mouse Vκ promoter is PCR amplified as a 290 bp PCR fragment from mouse genomic DNA using the following primers (designed according to the published NCBI-Genbank sequence entry X52768):

SEQ ID NO. 65 (P061)
5'-ccATCGATcctggtctacagtgtgaggtactggac-3',
and

SEQ ID NO. 66 (P062)
5'-
ccATCGATGGATCCtctgagagctggaagagaggatgctttattagg-3'

Figure 13A:
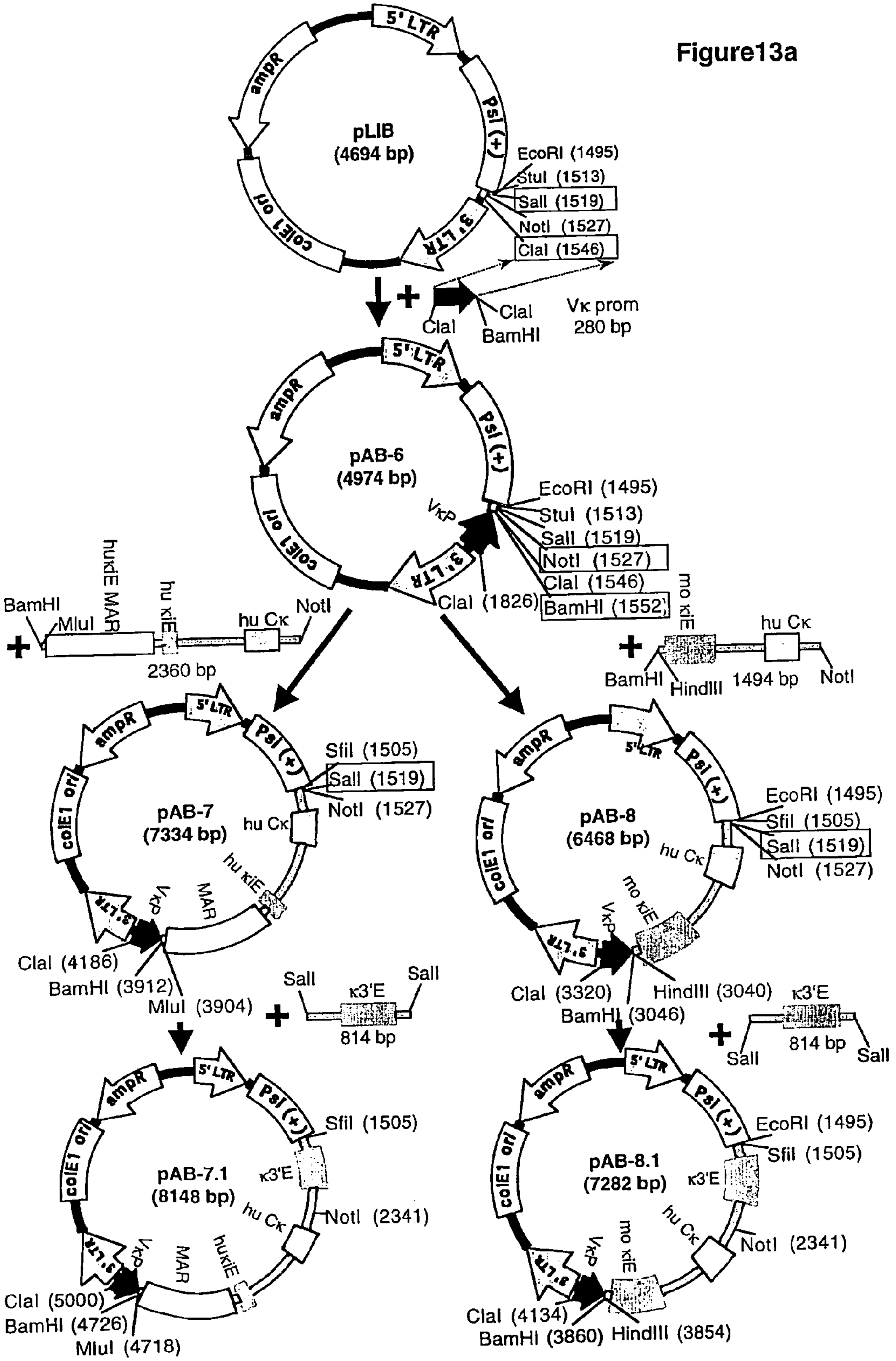
FIG. 13*a* shows the construction of retroviral expression vectors for the expression of human IgκL chains (preparatory step I). Similar to the construction of retroviral expression vectors for IgH chains, expression vectors for IgκL chains require the κL chain locus specific promoter and enhancer elements in addition to the coding regions for the κL chain proteins, which need to be sequentially cloned into a retroviral transfer vector. Starting from the basic retroviral vector pLIB, first, a Vκ promoter is cloned into pLIB, as indicated. This is followed by the insertion of a PCR product containing the human κ intron enhancer (κiE, with its upstream matrix associated region, MAR) and the human κL chain constant region gene (left side of the drawing), or, alternatively, by the insertion of a fusion PCR fragment of the mouse κiE with the human κL chain constant region gene (right side of the drawing), which is generated by a single overlap extension (SOE) PCR. Into both constructs, a PCR product containing the murine κ3' enhancer (κ3'E) is inserted. Restriction enzymes incorporated at the termini of the various genomic PCR fragments, as well as unique compatible restriction enzyme sites in the plasmid backbone, which can be used in the various cloning steps, are indicated.
Figure 13B:
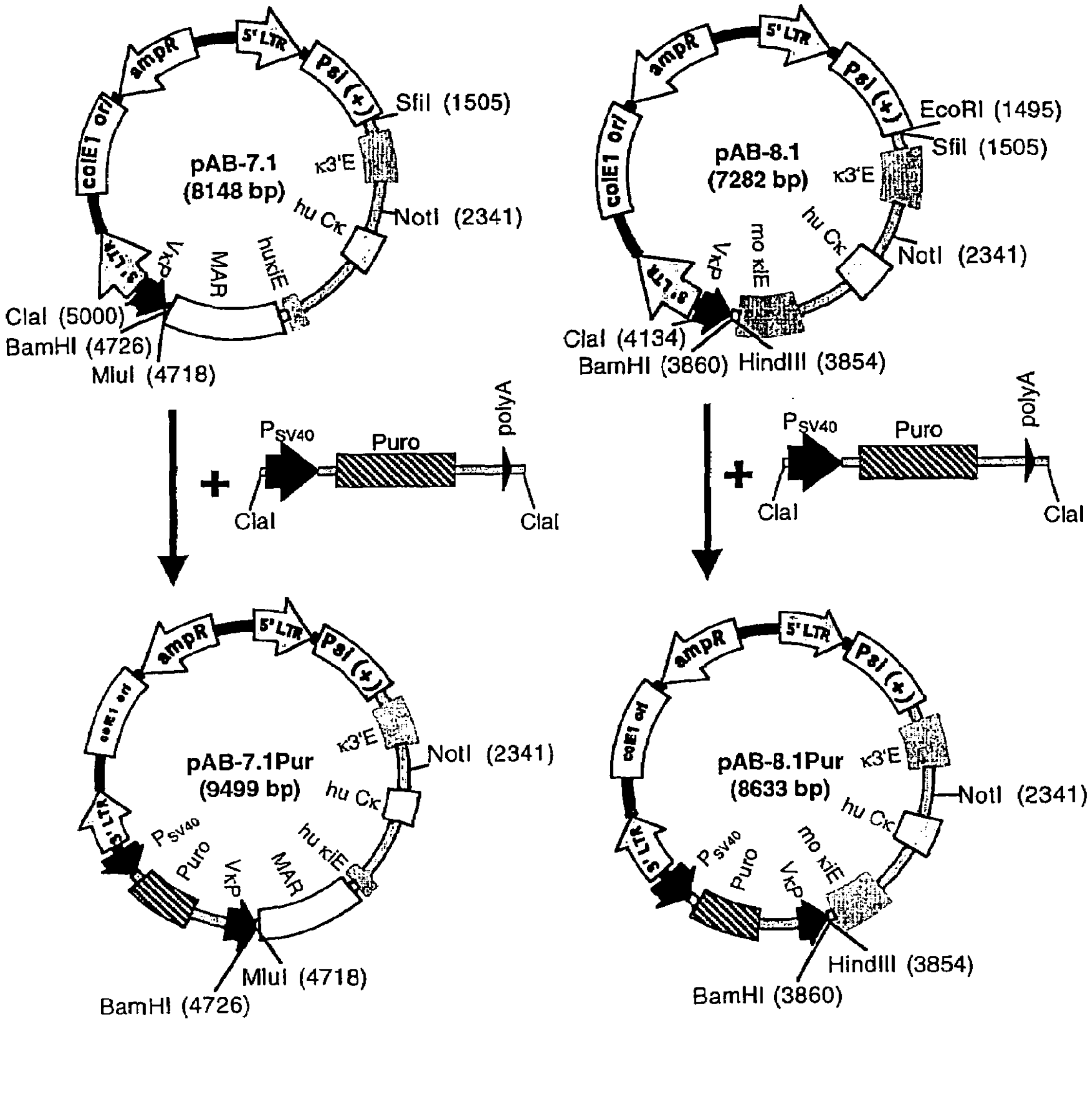
FIG. 13*b* illustrates the construction of retroviral expression vectors for the expression of human IgκL chains (preparatory step II). Retroviral expression constructs for human IgH and IgκL chains will be sequentially transduced into preB cells, and it is therefore desireable to be able to select for stably transduced cells after the first round of transduction with IgκL chain expressing vectors. For this reason a SV40 promoter driven puromycin expression cassette is inserted into the two possible IgκL chain retroviral transfer vector intermediates pAB-7.1 and pAB-8.1, as indicated. Upon cloning of a VκJκ rearranged variable domain exon into these vectors, these retroviral constructs are capable of expressing human IgκL chains (see FIG. 15).

Restriction sites appended to the 5' end each primer are highlighted by uppercase letters. In addition to ClaI sites present at the 5' ends of both primers, the reverse primer P062 contains an additional BamHI restriction site (GGATCC, underlined) introducing another unique restriction site into the PCR product which will be used for later cloning purposes. After ClaI restriction enzyme digestion of the PCR fragment, the amplified $V_\kappa$ promoter is ligated into ClaI linearized pLIB vector. Ligation products containing the $V_\kappa$ promoter in the desired orientation (opposite to the transcriptional orientation of the 5'LTR promoter) are identified by diagnostic restriction enzyme mapping and DNA sequencing giving rise to construct pAB-6 (FIG. 13*a*).

The κiE and the coding region for the κL chain constant domain are located in close proximity in both the human and the mouse κL chain gene locus and the enhancer appear to function across species. Therefore, the optional cloning procedures for two different retroviral expression vectors encoding κL chains is described, one utilizing the human, and the other utilizing the murine κ intron enhancer (κiE). It should be noted, that both constructs can be used interchangeably. Cloning of the construct containing the human κiE can be achieved by amplifying a PCR fragment from genomic human DNA containing both the human κiE and the human Cκ exon including a 5' located MAR using the following primers (designed based on published NCBI-Genbank sequence entry AF017732):

```
SEQ ID NO. 67 (P063)
5'-
cgGGATCCTGACGCGTaccagggagaagactgatttattagagatttc-
3',
and

SEQ ID NO. 68 (P064)
5'-gatGCGGCCGCaaagattcactttatttattcattctcc-3'
```

Additional restriction sites appended to the 5' end of each primer are again highlighted in uppercase letters (BamHI in primer P063 and NotI in P064). Primer P063 contains the sequence for an additional MluI restriction site used in later cloning steps. The PCR primers amplify a 2359 bp fragment that can be digested with BamHI and NotI, and which can then be directionally cloned into BamHI-NotI linerized pAB-6 generating retroviral construct pAB-7 (FIG. 13*a*).

For the construct utilizing the murine κiE a PCR product containing the murine κiE is fused to a PCR product containing the human Cκ region by the SOE-PCR approach described previously. For this, first PCR amplification of the murine κiE and the human Cκ region is performed in parallel, with the κiE reverse primer and the Cκ region forward primer exhibiting a 36 bp region of complementarity. In the second PCR, which is used to fuse these two PCR products, 1/100 of each PCR reaction is mixed and amplified with the κiE forward (P065) and the Cκ region reverse primer (P064) resulting in the fusion of the two PCR products at the region of 36 bp terminal complementarity.

The following primers can be used for the amplification of the murine κiE (designed based on the published NCBI-Genbank sequence entry V00777) using mouse genomic DNA as a template:

```
SEQ ID NO. 69 (P065)
5'-cgGGATCCAAGCTTgaaaaatgtttaactcagctactataatccc-
3'

SEQ ID NO. 70 (P066)
5'-gttttgttggagctcccctttgaagatattctcaggcttccttc-3'
```

The following primers can be used for the amplification of the human Cκ region (designed based on the published NCBI Genbank sequence entry AF017732) using human genomic DNA as a template:

```
SEQ ID NO. 71 (P067)
5'-
aatatcttcaaaggggagctccaacaaaacaatttagaactttattaag-
3'

SEQ ID NO. 68 (P064)
5'-gatGCGGCCGCaaagattcactttatttattcattctcc-3'
```

The regions of terminal complementarity in primers P066 und P067 are underlined, which mediate the fusion of the two PCR products in a second PCR carried out with primers P065 and P064 and a mixture of the two first PCR products as a template. The resulting murine κiE-human Cκ fusion PCR product of 1524 bp can be digested with BamHI and NotI and is then directionally cloned into BamHI-NotI linearized vector pAB-6 generating vector pAB-8 (FIG. 13*a*).

Next the murine κ3'E is cloned downstream of the human Cκ regions in both pAB-7 and pAB-8 generating constructs pAB-7.1 and pAB-8.1, respectively. The primers used for the PCR amplification for the κ3'E from mouse genomic DNA are as follows (designed based on published NCBI-Genbank sequence entry X15878):

```
SEQ ID NO. 72 (P068)
5'-acgcGTCGACtagaacgtgtctgggccccatgaaacatc-3',
and

SEQ ID NO. 73 (P069)
5'-cgatGTCGACagctcaaaccagcttaggctacacagagaaac-3'
```

Both primers contain SalI restriction sites (highlighted in uppercase letters), such that the resulting 827 bp PCR product can be cloned into the compatible SalI restriction sites of pAB-7 and pAB-8. Vector clones carrying the insert in the correct orientation and with the correct DNA sequence, as determined by restriction enzyme mapping and DNA sequencing, are designated pAB-7.1 and pAB-8.1 (FIG. 13*a*).

In a next cloning step, a puromycin resistance marker under control of a constitutive SV40 promoter is cloned into the retroviral κL chain expression constructs. The inclusion of an expression cassette for puromycin resistance is preferred, because both IgH and IgL chain retroviral constructs need to be stably co-transduced into murine preB cells in order to allow expression of complete heterologous antibodies. In order to increase the efficiency of retroviral cotransduction, retroviral IgL chain constructs are transduced first, and stably transduced cells are selected for the integration of the IgL chain constructs using puromycin selection. A secondary transduction of IgH chain retroviral vectors will then give rise to cells with the potential for antibody production in each cell that is transduced with an IgH chain retroviral vector.

The puromycin expression cassette can be cloned from the puromycin resistance vector pPur (Clontech) by SOE-PCR deleting some unwanted internal restriction enzyme sites and adding suitable ClaI cloning sites to the ends of the amplified PCR fragment.

The primers used for the SOE fusion PCR are:

```
SEQ ID NO. 74 (P070)
5'-ccATCGATctgtggaatgtgtgtcagttagggtgtgg-3'

SEQ ID NO.75 (P071)
5'-tcaggggatggtggcggccctaggcctccaaaaaagcctcctcactacttc-3'
```

-continued

SEQ ID NO. 76 (P072)
5'-cttttttggaggcctagggccgccaccatcccctgacccacgcccctgacc-3'

SEQ ID NO. 77 (P073)
5'-ccATCGATccagacatgataagatacattgatgag-3'

First, two PCR amplifications are performed in parallel with primer pairs P070/P071 and P072/P073 using the same pPur template for the PCRs. Reverse primer P071 and forward primer P072 are designed to contain a region of 36 bp perfect complementarity (underlined), which will allow the fusion of the two PCR products by a second PCR using aliquots of the previous PCR fragments in an additional PCR amplification using primers P070 and P073 alone. The latter primers contain ClaI restriction sites (uppercase letters) allowing the cloning of the resulting 1351 bp puromycin expression cassette into compatible ClaI sites of pAB-7.1 and pAB-8.1. This generates retroviral constructs pAB-7.1Pur and pAB-8.1Pur, respectively (FIG. 13*b*), which are the constructs into which single $VJ_\kappa$ regions or $VJ_\kappa$ region libraries encoding unique or diverse variable domains of κL chains, respectively, can be inserted. The procedure for cloning of the variable region exons will be presented further below together with the cloning of H chain and λL chain variable regions, after also the cloning of the retroviral expression vectors for heterologous, human λL chains have been described.

(c) Generation of Retroviral Constructs for the Regulated Expression of IgλL Chains In some cases it is desirable to produce heterologous antibodies containing λL chains instead of κL chains. Although it might be sufficient to replace the human Cκ coding region in the retroviral constructs pAB-7.1Pur and pAB-8.1Pur with any of the human Cλ coding regions, a perfect endogenous λL chain expression pattern will only be achieved by controlling the expression of λL chains by λL chain gene locus specific promoter and enhancer elements. This is particularly true in the murine system, where κL chain gene rearrangement and expression precedes the rearrangement and expression of λL chains during B cell differentiation.

The murine λL chain gene locus specific enhancer elements are the λ2-4 enhancer and the λ3-1 enhancer, which are located close to the Cλ2, Cλ4, and Cλ1, Cλ3 constant region exons and regulate the expression of λ2, λ4, and λ1, λ3 light chain isotypes, respectively.

As in the case of κL chain retroviral expression constructs (see above), retroviral λL chain expression vectors are designed to contain a puromycin resistance gene expression cassette. Therefore, in the first cloning step, a SV40 promoter controlled puromycin expression cassette is fused to a Vλ promoter by SOE-PCR using mouse genomic DNA and pAB-7.1Pur as templates for PCR amplification, respectively. The primers for the two parallel SOE-PCR reactions are as follows (with the Vλ promoter specific primers P076 and P077 designed based on the published NCBI-Genbank database sequence entry J00591):

SEQ ID NO. 78 (P074)
5'-ccATCGATctgtggaatgtgtgtcagttagggtgtgg-3'

SEQ ID NO. 79 (P075)
5'-gatgtcacgtgagatcccagacatgataagatacattgatgagttt g-3'

SEQ ID NO. 80 (P076)
5'-tcttatcatgtctgggatctcacgtgacatcttataataaacctg-

3'

-continued

SEQ ID NO. 81 (P077)
5'-ccATCGATACGCGTaattcacaaaccaagtctattatttcaata-

3'

As for the SOE fusion PCRs described earlier, first two PCR amplifications are performed in parallel, i.e. the puromycin expression cassette with primers P074 and P075 on pAB-7.1Pur as a template, and the Vλ promoter with primers P076 and P077 on mouse genomic DNA as a template. Each 1/100 volume aliquots of the first parallel PCRs are then mixed and amplified again with primers P074 and P077. The puromycin expression cassette is thereby fused to the 5'end of the Vλ promoter, because of the 36 bp designed perfect complementarity in reverse primer P075 and sense primer P076 (underlined) that is used for the first round parallel PCRs.

Figure 14A:
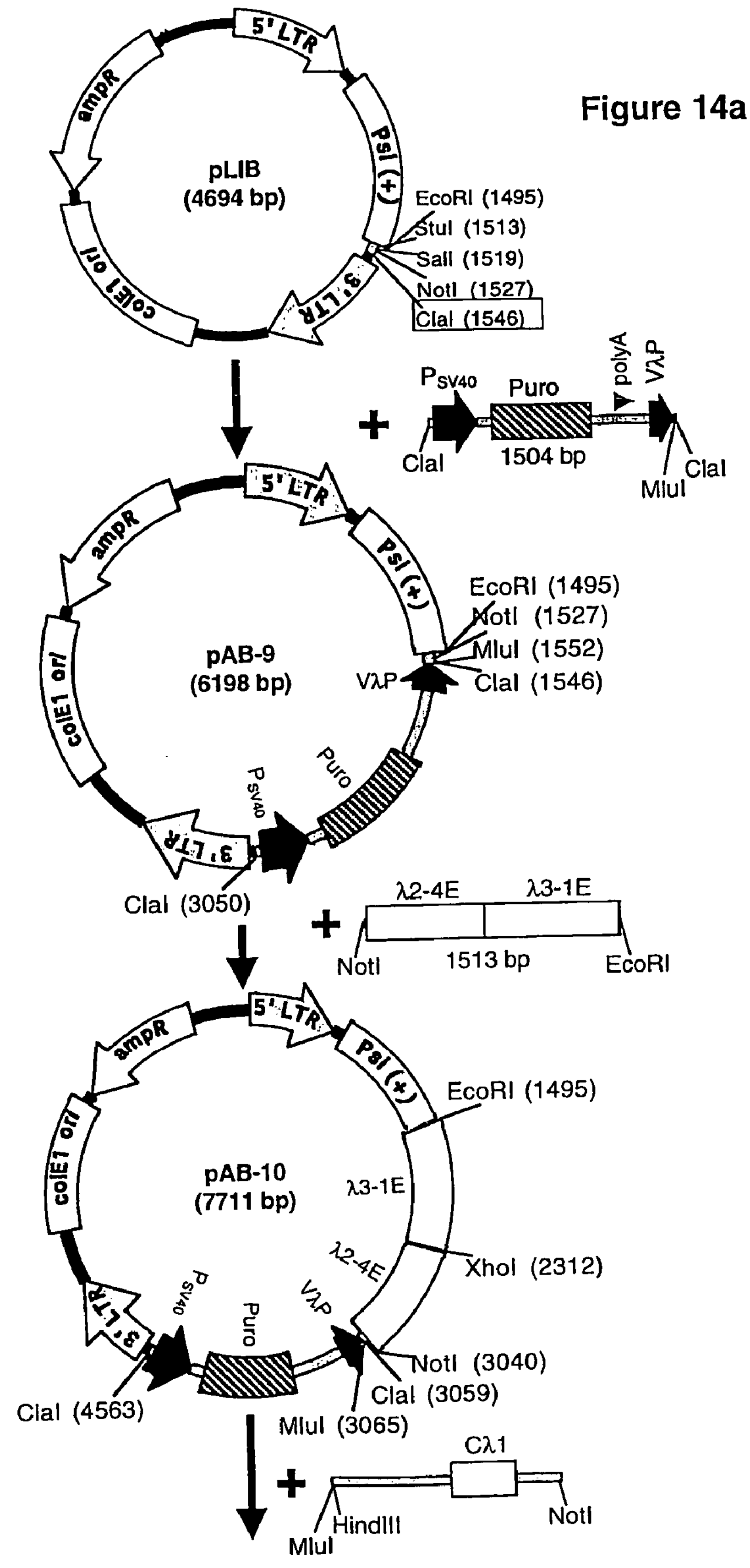
FIG. 14*a* shows the construction of retroviral expression vectors for the expression of human IgλL chains (preparatory step I). Retroviral expression constructs for human IgλL chains are cloned by first inserting a fusion PCR product of a puromycin cassette and a Vλ promoter into pLIB (the PCR fusion is performed by single overlap extension (SOE) PCR as described in the example section). In the next step, a SOE-PCR fusion construct of two murine λL chain enhancer elements, the λ2-4 and the λ3-1 enhancer, are inserted into the construct, as indicated. Finally, the coding region of the human Cλ1 region is inserted by PCR cloning into this retroviral cloning vector using the indicated restriction enzymes. Upon cloning of a VλJλ rearranged variable domain exon into these vectors, these retroviral constructs are capable of expressing human IgλL chains (see FIG. 15).

Both primers P074 and P077 contain ClaI restriction sites that can be used to clone the PCR fusion product into ClaI linearized pLIB. An additional MluI restriction site (underlined) is also incorporated into reverse primer P077 giving rise to an additional unique MluI site 3' of the Vλ promoter required for further cloning steps. A vector clone with the puromycin-Vλ promoter fusion PCR fragment inserted in pLIB in the correct orientation and with the correct DNA sequence, as verified by restriction enzyme mapping and DNA sequencing, is designated vector pAB-9 (FIG. 14*a*).

Next, the two murine λ2-4E and λ3-1E enhancer elements are PCR amplified from mouse genomic DNA, again followed by fusing both sequences by SOE-PCR. The following primers can be used (based on the published NCBI-Genbank sequences entries X54550 and X54608, respectively):

SEQ ID NO. 82 (P078)
5'-catGCGGCCGCgagtatccctgtgcagtggggatactcag-3'

SEQ ID NO. 83 (P079)
5'-
tctcaggagagaCTCGAGactcctttgtgctctgatagcacacatgac-
3'

SEQ ID NO. 84 (P080)
5'-
gcacaaaggagtCTCGAGtctctcctgagatggttcataggcctgcc-3'

SEQ ID NO.85 (P081)
5'-ggGAATTCtctagacataaggaacaaagtcagtgtgcc-3'

Like in the previous approach, first, two PCR fragments are amplified in parallel with primer pair P078/P079 and P080/P081 using mouse genomic DNA as a template, and in a second PCR round aliquots of these PCR products are used as a template and fused by PCR amplification with primers P078 and P081 due to the 36 bp complementarity of primers P079 and P080 (underlined).

The resulting 1513 bp PCR fusion product can be digested with NotI and EcoRI restriction enzymes (the respective recognition sites being incorporated into primers P078 and P081; highlighted in uppercase letters) and is directionally cloned into NotI/EcoRI linearized pAB-9. A vector clone with the correct DNA sequence, as verified by restriction enzyme mapping and DNA sequencing, is designated vector pAB-10 (FIG. 14*a*). The complementary regions in primers P079 and P080 are designed to contain an additional unique XhoI site (highlighted in uppercase letters), in order to allow the separate removal of each of the enhancer elements, if desired.

In a next step, any of the human Cλ regions is cloned into the retroviral construct pAB-10 using the following primers (designed based on published NCBI-Genbank sequences D87023 and D87017):

```
SEQ ID NO. 86 (P082)
5'-ccACGCGTaaaagcttgtctaggtggagcccactccttgcc-3'

SEQ ID NO. 87 (P083)
5'-catGCGGCCGccctgtaccccacactgagaaccccgggg-3'
```

Figure 14B:
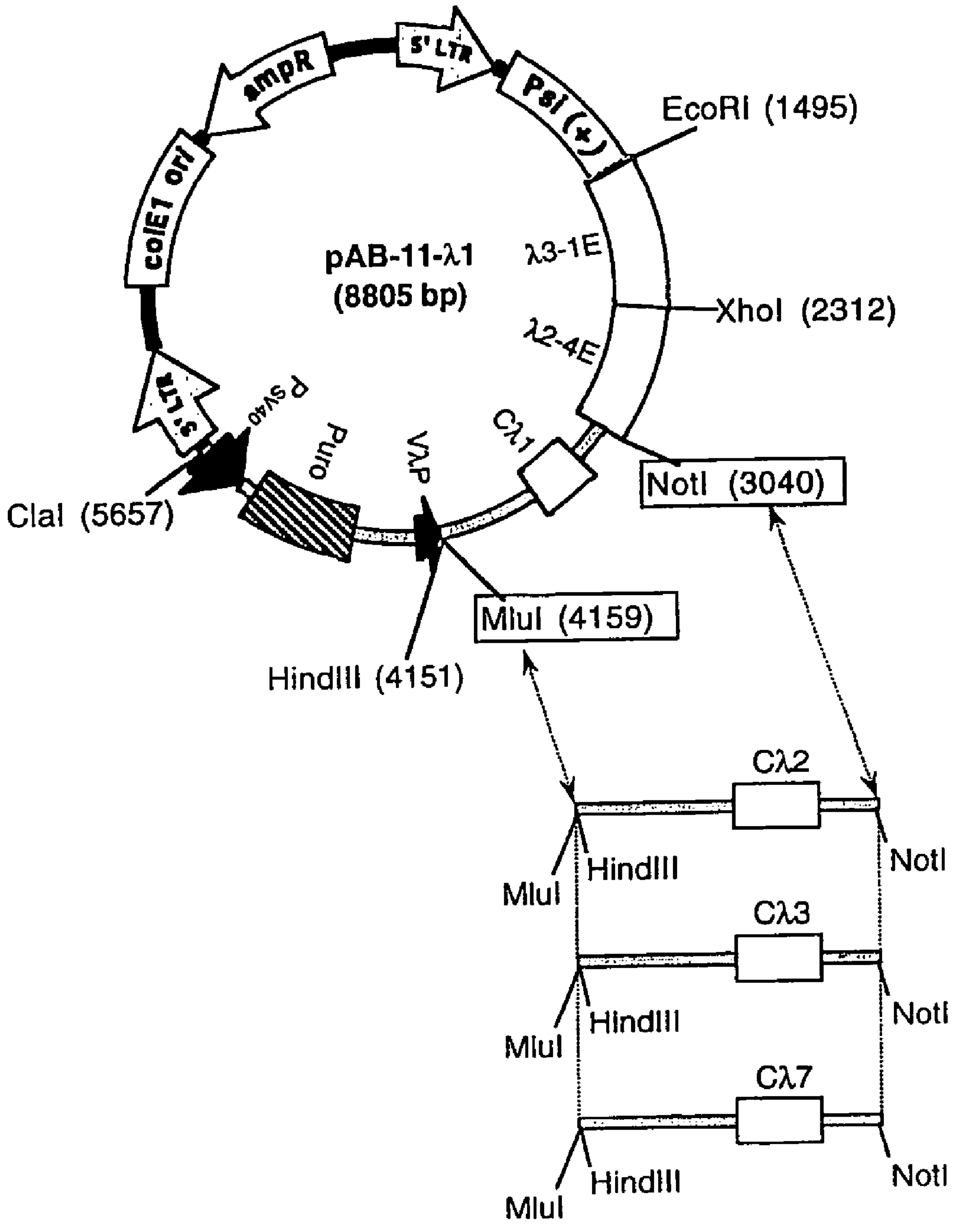
FIG. 14*b* illustrates the construction of retroviral expression vectors for the expression of human IgλL chains (preparatory step II). Other human IgλL chain constant region genes may be used to replace the Cλ1 coding region by simple cloning using the unique MluI-NotI restriction enzymes, as indicated. Upon cloning of VλJλ rearranged variable domain exons into these vectors, these retroviral constructs are capable of expressing the different human IgλL chain isotypes, as indicated (see FIG. 15).

These primers are able to amplify any of the functional human Cλ regions as 1094 bp PCR fragments if human genomic DNA is used as a template. Primers P082 and P083 contain restriction sites for ClaI and NotI, respectively, allowing ClaI-NotI double digestion of the PCR fragments and their directional ligation into pAB-10 in order to generate (depending on the amplified Cλ region) either pAB-11-λ1, pAB-11-λ2, pAB-11-λ3, or pAB-11-λ7 (FIG. 14*b*).

For the generation of a complete IgλL chain retroviral expression vector a VλJλ rearranged variable region exon has to be cloned into the unique MluI and HindIII sites of the various pAB-11 constructs, which is described in the following section, together with the generation of complete IgH and IgκL chain retroviral expression vectors.

Example 7

Figure 15:
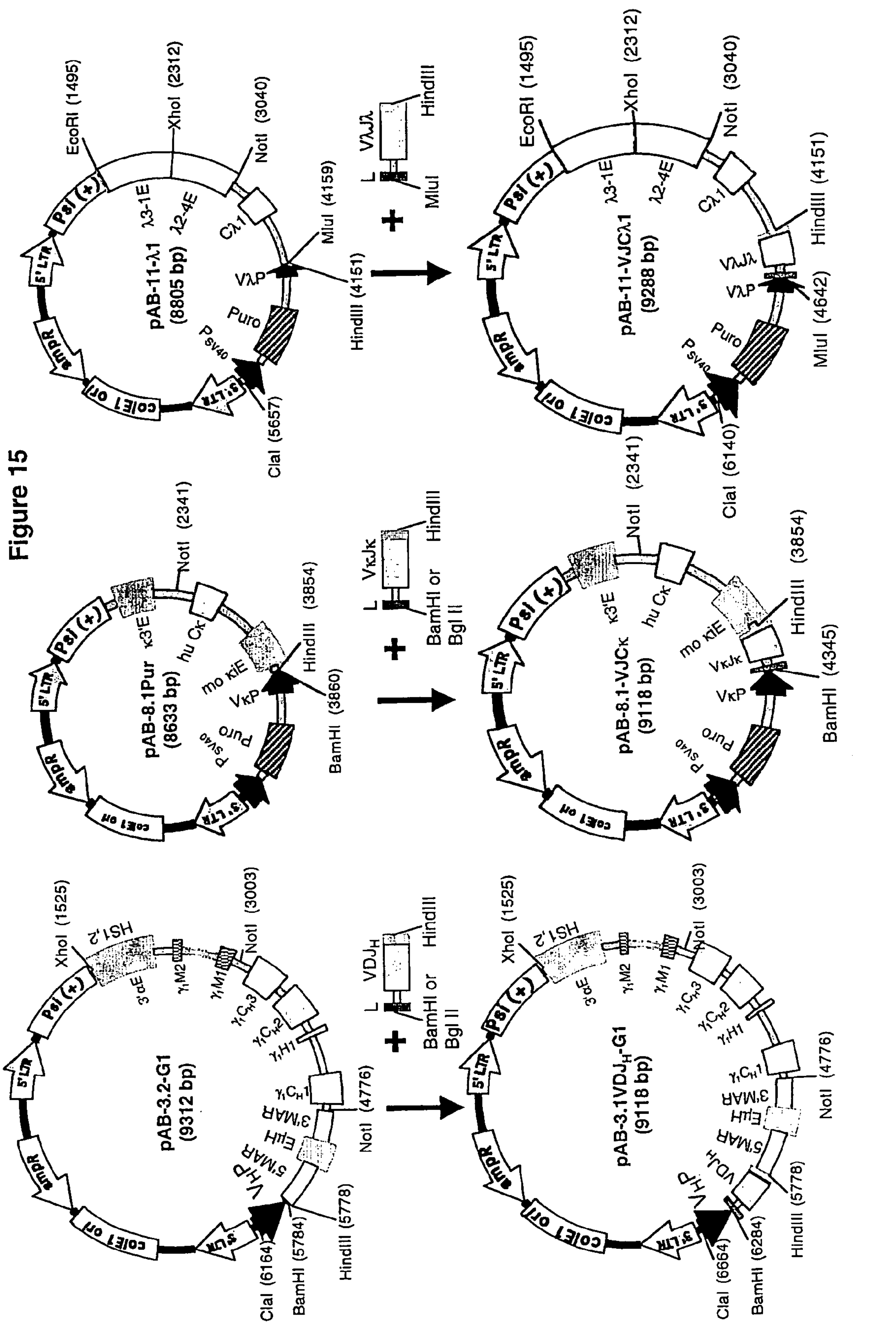
FIG. 15 shows the insertion of V-region genes into retroviral human IgH, IgκL and IgλL chain expression vectors. All retroviral expression constructs for human IgH and L chains that have been described so far did not contain coding regions for the variable domains. These can be isolated by PCR cloning from various sources (see e.g.

Cloning of $V_H DJ_H$ or $V_L J_L$ Variable Region Exons into Retroviral IgH and L Chain Expression Constructs The retroviral expression constructs for the different human IgH and IgL chains described so far contain all the coding regions and control elements for human antibody expression, with the exception of the coding regions for the variable domains. Diverse repertoires (libraries) of exons encoding variable region domains can e.g. be cloned from genomic DNA of human peripheral blood lymphocytes containing B lymphocytes with diverse $V_H DJ_H$ and $V_L J_L$ DNA rearrangements. These coding regions for the variable domains need to contain a common leader exon, located 5' of each $V_H DJ_H$ and $V_L J_L$ rearranged exon (FIG. 15), which is required for the proper transport of IgH and IgL chains through the endoplasmatic reticulum, the trans golgi network and eventually to the cell surface. Degenerate primers binding to the majority of leader sequences of the human IgH, IgκL and IgλL variable region leader sequences have been described and are used in combination with degenerate primers amplifying the various human $J_H$ and $J_L$ gene segments for the cloning of the $V_H DJ_H$ or $V_L J_L$ variable coding regions. Recognition sites for restriction enzymes used for the directional cloning of the PCR products (see FIG. 15) are appended to the 5' end of the degenerate primers and are highlighted in uppercase letters. Positions in the degenerate primers, which may contain more than only one nucleotide are indicated in parentheses.

Forward primers for the PCR amplification of human Ig heavy chain variable domains including leader sequences from human genomic DNA of peripheral B lymphocytes are as follows:

```
SEQ ID NO. 88 (P084)
5'-gcGGATCCatggactggacctggagg(ag)tc(ct)tct(gt)c-3'

SEQ ID NO. 89 (P085)
5'-gcGGATCCatggag(ct)ttgggctga(cg)ctgg(cg)ttc(ct)t-3'

SEQ ID NO. 90 (P086)
5'-gcGGATCCatgga(ac)(ac)(at)act(gt)tg(gt)(at)(cgt)c(at)(ct)(cg)ct(ct)ctg-3'
```

A forward primer for the amplification of human Igκ light chain variable domains including leader sequence from human genomic DNA of peripheral B lymphocytes is as follows:

```
SEQ ID NO 91 (P087)
5'-gcGGATCCatggacatg(ag)(ag)(ag)(agt)(ct)cc(act)(acg)g(ct)(gt)ca(cg)ctt-3'
```

A forward primer for the amplification of human Igλ light chain variable domains including leader sequence from human genomic DNA of peripheral B lymphocytes is as follows:

```
SEQ ID NO 92 (P088)
5'-gcACGCGTatg(ag)cctg(cg)(at)c(ct)cctctc(ct)t(ct)ct(cg)(at)(ct)-3'
```

Note, that instead of a BamHI restriction enzyme recognition site appended to the 5' end of primers P084-P087 for cloning purposes, a recognition site for the BglII restriction enzyme can be used instead (compare to FIG. 15), because BglII generates the same compatible overhangs, as BamHI. In case of cloning of VλJλ regions the forward primer P088 contains a MluI site, because the retroviral construct accepting the fragment already contains internal BamHI restriction sites. Alternatively, a primer similarly to P088 may be used containing an AscI site producing the same CGCG overhang as MluI restriction enzyme.

Reverse primers for the amplification of all six human IgH J chain gene segments: are as follows. HindIII sites, highlighted in uppercase letters, are appended to the 5' ends of the primers including some flanking nucleotides for cloning purposes.

A reverse primer for the PCR amplification of variable region exons containing $J_H1$, $J_H4$, and $J_H5$ gene segments using genomic DNA from human B lymphocytes is as follows:

```
SEQ ID NO 93 (P089)
5'-tatAAGCTTacctgaggagacggtgaccagggtgccctgg-3'
```

A degenerate reverse primer for the amplification of variable region exons containing $J_H2$, $J_H3$, and $J_H6$ gene segments using genomic DNA from human B lymphocytes is as follows:

```
SEQ ID NO 94 (P090)
5'-tatAAGCTTacctgaggagacggtgacca(tg)(tg)gt(gc)cc(ta)(tc)(gt)g-3'
```

A reverse degenerate primer for the amplification of variable κ region exons containing human Jκ1-4 gene segments using genomic DNA from human B lymphocytes is as follows:

```
SEQ ID NO 95 (P091)
5'-
tatAAGCTTacgtttgatctcca(cg)(ct)ttggtccct(tgc)ggcc-
3'
```

A reverse primer for the amplification of variable κ region exons containing the human Jκ5 gene segment using genomic DNA from human B lymphocytes is as follows:

```
SEQ ID NO 96 (P092)
5'-tatAAGCTTacgtttaatctccagtcgtgtcccttggcc-3'
```

A reverse degenerate primer for the PCR amplification of variable region IgλL exons containing Jλ1-3 gene segments using genomic DNA from human B lymphocytes is as follows:

```
SEQ ID NO 97 (P093)
5'-
tatAAGCTTacctaggacggtcagcttggtccc(ta)(cg)c(tg)cc-
3'
```

A reverse primer for the PCR amplification of variable region IgλL exons containing Jλ7 using genomic DNA from human B lymphocytes is as follows:

```
SEQ ID NO 98 (P094)
5'-tatAAGCTTaccgagggcggtcagctgggtgcctcctcc-3'
```

For the PCR amplification and cloning of variable domain exons contain rearranged $V_HDJ_H$ and $V_LJ_L$ gene segments with the above described primers P084-P094, equimolar amounts of primers are used, if more than one forward or reverse primer is indicated for a particular variable region. In case of cloning of variable regions for H and κL chains, the PCR fragments are digested with BamHI and HindIII and are directionally cloned into BamHI/HindIII double digested vectors for IgH and IgκL chain expression. In case of cloning of variable regions for λL chains, the PCR fragments are digested with MluI and HindIII and are directionally cloned into MluI/HindIII double digested vectors for IgλL chain expression.

Example 8

Sequential Transduction of Retroviral Expression Vectors for Heterologous

IgH and L chains into genetically modified murine preB cells The retroviral transduction of stromal cell and IL7 dependent murine preB cells has been described in detail in Example 3. For the sequential transduction of retroviral expression constructs encoding IgH and IgL chains, identical protocols are used for the transfection of the ecotropic packaging cells and the conditions to infect recombinant retroviruses into preB cells. The only difference is that two retroviral expression constructs are sequentially transduced by the protocol outlined below.

Stromal cell and IL7 dependent preB cells are first infected with supernatant from GPE packaging cells that have transiently been transfected with the retroviral construct encoding heterologous IgL chains. As described above, the IgL chain expression vectors additionally contain a puromycin resistance marker. Therefore, stably transduced cells can be selected by the addition of 2 μg/ml puromycin to the tissue culture medium 24 hours post transduction. Transduced cells are cultured and expanded for an additional period of 48 hours in puromycin containing medium. Non-transduced preB cells will be eliminated due to the puromycin selection and a 100% IgL chain transduced population of preB cells will be obtained after 48 hours of culture.

At this point, cells are incubated with supernatant of the ecotropic packaging cell line GPE that have transiently been transfected with retroviral vectors encoding heterologous IgH chains. These cells are then kept in culture for an additional period of 24 hours upon which they cease to proliferate due to the expression of the heterologous immunoglobulin heavy chains. The cells are then harvested and may be used for the transplantation of immunocompromised mice, where these cells can reconstitute B lineage compartments, and where they are able to participate within an immune response giving rise to heterologous antibody secreting cells.

Example 9

Transplantation of Long-Term Proliferating Murine Precursor B Cells into Mice for the Production of Heterologous Antibodies Stromal cell and IL7 dependent preB cells expressing heterologous IgH and L chains from stably transduced retroviral expression vectors are intravenously injected into either B cell deficient JHT mice, or together with $CD4^+$ T-helper cells into CB17 SCID, RAG-2 or RAG-2 deficient mice, such that the transplanted cells can mount T cell dependent or independent immune responses upon antigenic stimulation of the transplanted mice.

For this, 1.5 to 3 month old mice are sublethally irradiated with 300-600 rad γ-irradiaton and 4-6 hour post irradiation the mice are intravenously injected with $5\times10^6$ to $10^7$ preB cells resuspended in PBS. In case of additional transplantation of $CD4^+$ T-helper cells, $CD4^+$ cells are isolated from pooled cervical, axillary, mesenteric and inguinal lymph nodes of syngeneic mice by depletion of B cells and $CD8^+$ T cells by use of sheep-anti-mouse Ig antibody coated Dynabeads (Milan Analytica AG, La Roche, Switzerland). $10^6$ of these routinely more than 90% pure $CD4^+$ T-helper cells are coinjected with preB cells. Cell populations are allowed to reconstitute B and T cell compartments of the transplanted hosts for 6 weeks following transplantation.

Example 10

Immunization of preB Cell Grafted Mice

Immunizations of immunocompromised mice transplanted and reconstituted with HupreB cells and T helper cells is done essentially as described (Harlow and Lane, *Cold Spring Harbor Laboratory Press*, p. 150-173, 1988). In brief, 10-50 μg of antigen is dissolved in 250 μl PBS and vigorously mixed with 250 μl complete Freund's adjuvant and the antigen-adjuvant mixture is injected intraperitonally. After two weeks, mice are boosted intraperitonally with 5-20 μg of antigen, this time mixed with incomplete Freund's adjuvant. 10 days following the first boost, mice are analyzed for antigen specific heterologous antibodies in the serum. The best responders are boosted again four weeks afterwards with 5-20 μg of antigen in incomplete Freund's adjuvant both intraperitoneally and intravenously. 3 days later, spleen cells are isolated from mice and used for the generation of hybridoma cells secreting heterologous antigen-specific monoclonal antibodies.

Example 11

In Vitro Stimulation of HupreB Cells with for the Differentiation into Antibody Secreting Plasma Cells Stromal cell and IL7 dependent HupreB cells can also be differentiated into antibody secreting cells entirely in tissue culture in vitro. For this, continuously proliferating HupreB cell cultures are first differentiated into surface immunoglobulin positive B cell by withdrawal of IL7 from the tissue culture medium and the continued culture on irradiated stromal cells for two to three days. The absence of growth factors in the medium results in the arrest of proliferation and the induction of differentiation which is accompanied by the induction of apoptosis, unless an anti-apoptotic gene, like bcl-2 is expressed in the differentiating cells.

The differentiated cells are then harvested, and replated on fresh irradiated stromal cells e.g. in the presence of 100 U/ml rIL4 and 20 μg/ml of an agonistic anti-CD40 monoclonal antibody. Within 5-6 days of culture the cells differentiate into large proliferating cells of plasma cell phenotype, that are able to secrete large amounts of antibodies from the heterologous Ig gene loci and that can be used for generation of heterologous monoclonal antibody secreting hybridoma cell clones.

Example 12

Fusion of Myeloma Cells with Plasma Cells Derived from HupreB Cells for the Generation of Hybridomas Producing Human Monoclonal Antibodies For the immortalization of plasma cells derived from HupreB cells, either upon in vitro differentiation (Example 11), or after immunization of transplanted mice (Example 10), the plasma cells need to be fused with an immortal myeloma cell line. The myeloma cell lines that are used for the cell fusion lack the expression of the HGPRT gene, involved in the salvage pathway of nucleotide biosynthesis. While these cells grow indefinitively in regular tissue culture medium, they will die, if de novo nucleotide synthesis is blocked by addition of e.g. the drug aminopterine to the tissue culture medium. In contrast, cells expressing the HGPRT gene can survive a block of de novo nucleotide synthesis by aminopterine, especially, if additional thymidine and hypoxanthine are supplemented, because the HGPRT gene product can utilize these substances for the synthesis of pyrimidine and purine nucleotides, respectively. Thus, in HAT selection medium (containing hypoxanthine, aminopterine and thymidine), only those cells survive and proliferate, that resulted from a fusion of the mortal, but $HGPRT^+$, antibody secreting plasma cell and the immortal, but $HGPRT^-$, and therefore aminopterine sensitive myeloma cell. These cells are called hybridoma cells, and, if subcloned, will secrete a monoclonal antibody of the specificty encoded by the plasma cell fusion partner.

For the generation of hybridoma cells, either plasma cells from the spleen of immunized mice transplanted with HupreB cells, or plasma cells generated in vitro by anti-CD40 and IL4 stimulation are used. In each case a homogeneous cell suspension is generated and washed twice with IMDM medium without any supplements, by repeated centrifugation (500 g, 5 min) and resuspension steps.

$5\times10^6$ myeloma cells (Sp2/0 Köhler and Milstein, *Eur. J. Immunol.,* 6, p. 511-519, 1976; or X63Ag8.653 Kearney et al., *J. Immunol.,* 123, p. 1548-1550, 1979) and $5\times10^7$ spleen cells (or $5\times10^7$ in vitro differentiated plasma cells) are combined, mixed and centrifuged again at 500 g for 5 min. 1 ml of a 50% polyethylene glycol (PEG) 1500 dilution in IMDM medium is slowly added to the cell pellet, while the cells are resuspended by tapping. After 2 minutes incubation, 10 ml of DMEM medium without supplements are slowly added, and cells are eventually centrifuged at 500 g for 5 min. After removal of the supernatant, the cell pellet is resupended in 1 liter of IMDM based stroma cell growth medium (described in example 1), containing 100 U/ml recombinant IL6 and 1× concentrated HAT supplement. The cells are distributed in 50 96-well tissue culture plates and are incubated at 37° C. until individual hybridoma clones can be identified and isolated for further expansion and characterization in tissue culture.

The invention claimed is:

1. A method for the generation of vertebrate precursor B lymphocytes that can be used for the production of an antibody or an antigen-binding fragment(s) thereof, comprising:

(a) genetically modifying isolated vertebrate precursor B lymphocytes, which
  (i) are derived from primary lymphoid organs, and
  (ii) have the potential to differentiate into mature B lymphoid lineage cells, by introducing at least one exogenous genetic element encoding at least one antibody or antigen-binding fragment(s) thereof; and
(b) effecting differentiation of said genetically modified precursor B lymphocytes into mature lymphoid lineage cells either in vitro or in vivo, thereby generating B lymphocytes capable of producing an antibody or an antigen-binding fragment(s) thereof.

2. The method according to claim 1, further comprising the step of immortalizing the differentiated lymphocytes by:

(a) fusing the differentiated lymphocytes to myeloma cells for the generation of hybridoma cells;
(b) infecting the differentiated lymphocytes with transforming viruses; or
(c) transfecting the differentiated lymphocytes with a vector construct ensuring expression of at least one transforming oncogene;

thereby generating vertebrate precursor B lymphocytes capable of permanently producing said binding protein, or functional fragment(s) thereof.

3. The method according to claim 1, wherein the vertebrate precursor B lymphocytes are able to express at least one component of the lymphoid V(D)J recombination machinery and originate from jawed vertebrates comprising cartilaginous fish, bony fish, amphibians, reptilia, birds, and mammals including pigs, sheep, cattle, horses and rodents including mice, rats, rabbits and guinea pigs.

4. The method of claim 3, wherein said lymphocytes are murine precursor (pre) B lymphocytes.

5. The method according to claim 1, wherein said vertebrate precursor B lymphocytes are deprived of their potential to express endogenous antibodies or antigen-binding fragment(s) thereof, which is achieved by isolating/selecting vertebrate precursor B lymphocytes being deficient in expressing endogenous immunoglobulins or fragments thereof, and/or by introducing into said vertebrate precursor B lymphocytes at least one vector construct designed to functionally inactivate at least one allele of at least one genetic element, which is selected from the group consisting of:

(a) the coding regions of the immunoglobulin heavy chain gene locus, including all or parts of the V, D, and J gene segments, and any of the coding regions for the constant region exons for μ, δ, γ, ϵ and α heavy chains, with or without their membrane spanning exons;
(b) the coding regions of the immunoglobulin K and/or X light chain gene loci, including any of the V and J gene segment coding regions, as well as any of the constant region exons;
(c) the cis-acting immunoglobulin heavy chain gene locus enhancer elements, including the heavy chain intron enhancer and the 3'α enhancer;
(d) the cis-acting immunoglobulin light chain gene locus enhancer elements, including the κ light chain intron enhancer (κiE), the 3'κ enhancer, and the λ2-4 and λ3-1 enhancers;
(e) the trans-acting recombination activating genes, RAG-1 and RAG-2, including their promoter and enhancer elements, as well as their coding regions; and
(f) the trans-acting DNA repair genes essential for V(D)J recombination, including Ku70, Ku86, the catalytic subunit of DNA-dependent protein kinase (DNA-PKcs), DNA ligase IV, XRCC4 and Artemis, including their promoter and enhancer elements, as well as the coding regions of said genes.

6. The method according to claim 5, wherein said vector constructs include gene targeting vectors comprising regions of DNA sequence homology to said at least one genetic element enabling for homologous recombination.

7. The method according to claim 6, wherein said gene targeting vectors additionally comprise a pair of DNA recognition sequences for site-specific DNA recombination enzymes, flanking the positive selection marker, enabling deletion of said positive selection marker upon transfection and transient expression of nucleic acid sequences encoding at least one of the cognate recombinase enzymes.

8. The method according to claim 6, wherein said gene targeting plasmid vectors additionally comprise a negative selection marker enabling selection against transfectants in which said gene targeting vectors are randomly integrated into the genome by non-homologous recombination.

9. The method according to claim 6, wherein said regions of DNA sequence homology flank a positive selection marker enabling selection of positive transfectants.

10. The method according to claim 1, wherein said at least one exogenous genetic element encoding an antibody or functional fragment(s) thereof, is carried on a genetic construct selected from the group consisting of:

(a) recombinant retroviral DNA constructs comprising promoter, enhancer and coding nucleic acid sequences operably linked to allow expression of at least one antibody, or antigen-binding fragment thereof, being either wild-type or having (a) designed mutation(s) in the primary amino acid sequence(s) or being artificial;

(b) recombinant plasmid-based DNA constructs comprising promoter, enhancer and coding nucleic acid sequences operably linked to allow expression of at least one antibody, or antigen-binding fragment thereof, being either wild-type or having (a) designed mutation(s) in the primary amino acid sequence(s) or being artificial;

(c) recombinant plasmid-based mini-immunoglobulin gene loci with unrearranged V, D and J gene segments operably linked to allow V(D)J recombination and subsequent expression of at least one heterologous antibody, or antigen-binding fragment thereof, being either wild-type or having (a) designed mutation(s) in the primary amino acid sequence(s);

(d) bacterial, yeast or vertebrate artificial chromosomes comprising parts or all of immunoglobulin gene loci in germline configuration operably linked to allow V(D)J recombination and subsequent expression of at least one heterologous antibody or antigen-binding fragment thereof, being either wild-type or having (a) designed mutation(s) in the primary amino acid sequence(s);

(e) bacterial, yeast or vertebrate artificial chromosomes comprising parts or all of at least one heterologous immunoglobulin gene locus in modified arrangement designed to allow V(D)J recombination and subsequent expression of at least one heterologous antibody, or antigen-binding fragment thereof, being either wild-type or having (a) designed mutation(s) in the primary amino acid sequence(s); and (f) trans-chromosome elements which are fragments of heterologous chromosomes harboring parts or all of immunoglobulin gene loci in germline configuration allowing V(D)J recombination and subsequent expression of at least one heterologous antibody, being wild-type with respect to the primary amino acid sequence(s).

11. The method according to claim 1, wherein the at least one exogenous genetic element encodes a native or modified human antibody, or (an) antigen-binding fragment(s) thereof.

12. The method according to claim 1 wherein the at least one exogenous genetic element encodes a heterologous antibody or heterologous antigen-binding fragment thereof.

13. The method according to claim 1, wherein the differentiation of vertebrate precursor B lymphocytes is effected in vitro by:

(a) arresting proliferation of said vertebrate precursor B lymphocytes and inducing differentiation into mature lymphocyte lineage cells by cultivating in the absence of any precursor lymphocyte growth factor; and (b) inducing terminal lymphocyte differentiation by further cultivating said cells in the presence of at least one of the following components selected from:

(i) soluble T cell related stimulating factors, comprising interleukin-2, interleukin-4, interleukin-5, interleukin-6, interleukin-10, interleukin-13, TGF-β, and IFN-γ;

(ii) factors activating co-stimulatory receptors of B cells, comprising agonistic antibodies or active, recombinant ligands specific for CD40, B7-1 (CD80), B7-2 (CD86), complement receptors 1 (CD35) and 2 (CD21), LFA-1 (CD11a), LFA-3 (CD58), CD19, CD20, CD30, CD32, CD37, CD38, CD70, CD71, Igα (CD79α), Igβ (CD79β), TAPA-1 (CD81), Fas (CD95), TNF-receptor1 (p55, CD120a), TNF-receptor2 (p75, CD120b), Ox-40 (CD134), and lymphotoxin-β receptor; and (iii) B cell mitogenic factors, T cell independent antigens of type 1, and other polyclonal activators, including lipopolysaccharide (LPS), lipoproteins from gram negative bacteria, polyanions, poly-dIdC, pokeweed mitogen (PWM), and anti-immunoglobulin reagents;

and combinations thereof.

14. The method according to claim 1, wherein said differentiation in vivo is effected upon transplantation of said genetically modified precursor B lymphocytes into a suitable vertebrate host.

15. The method according to claim 14, wherein said lymphocytes are co-transplanted into said host with naïve or antigen primed T helper lymphocytes.

16. The method according to claim 14, wherein said differentiation in vivo is followed by immunization of said host with at least one desired immunogenic compound or composition.

17. The method according to claim 14, wherein said vertebrate host is a compatible host being deficient with respect to the generation of endogenous B cells, T cells, and/or NK (natural killer) cells, or a combination thereof.

18. The method according to claim 14, wherein the vertebrate host is selected from jawed vertebrates comprising cartilaginous fish, bony fish, amphibians, reptilia, birds, and mammals including pigs, sheep, cattle, horses and rodents including mice, rats, rabbits and guinea pigs.

19. The method according to claim 14, wherein said vertebrate host is mouse.

20. A method for the production of an antibody, antibodies or (an) antigen-binding fragment(s) thereof, comprising:

(a) genetically modifying vertebrate precursor B lymphocytes, which (i) are isolated from primary lymphoid organs, and (ii) have the potential to differentiate into mature B lymphoid lineage cells, by introducing at least one exogenous genetic element encoding at least one antibody or antigen-binding fragment(s) thereof;

or, alternatively, isolating genetically modified vertebrate precursor B lymphocytes from primary lymphoid organs, wherein said genetically modified vertebrate precursor B lymphocytes have the potential to differentiate into mature B lymphoid lineage cells, and carry at least one exogenous genetic element encoding at least one antibody or antigen-binding fragment thereof;

(b) effecting differentiation of said genetically modified precursor B lymphocytes into mature lymphoid lineage cells either in vitro or in vivo, thereby generating genetically modified and differentiated vertebrate B lymphocytes capable of producing an antibody or (an) antigen-binding fragment(s) thereof;

(c) effecting expression of the antibodies, antibody, or antigen-binding fragment(s) thereof.

21. The method according to claim 20, followed by the steps of:

(a) isolating from said differentiated lymphocytes the at least one exogenous genetic element, and (b) placing said genetic element(s) in an expression system enabling production of said at least one binding protein, or functional fragment(s) thereof.

22. The method according to claim 20, wherein a monoclonal antibody is produced.

23. The method according to claim 20, wherein polyclonal antibodies are produced.

24. The method of according to claim 20 wherein said antibodies, antibody or antigen-binding fragment(s) are at least partially human.

25. The method according to claim 20, wherein the antibodies, antibody, or antigen-binding fragment(s) thereof to be produced are selected from the group consisting of:

(a) antibodies being either membrane bound or secreted, and consisting of both heterologous heavy and light chain polypeptides in the stochiometric composition found in natural antibodies and consisting of any of the known heavy (μ, δ, γ, α, ϵ) and/or light (κ and λ) chain isotypes;

(b) antibodies with combinations of heavy and light chain polypeptides being completely human with respect to the primary amino acid sequence;

(c) hybrid antibodies containing heterologous heavy or light chain polypeptides from different vertebrate species;

(d) secreted Fab, scFv and F(ab')2 antibody fragments being either completely or partially heterologous; and (e) antigen-binding fragments of antibodies covalently coupled via linker peptides, resulting in bispecific or multispecific antibody fragments.

* * * * *

UNITED STATES PATENT AND TRADEMARK OFFICE

CERTIFICATE OF CORRECTION

PATENT NO. : 7,741,077 B2
APPLICATION NO. : 10/499631
DATED : June 22, 2010
INVENTOR(S) : Grawunder et al.

It is certified that error appears in the above-identified patent and that said Letters Patent is hereby corrected as shown below:

In claim 5 at column 108, line 26, "(b) the coding regions of the immunoglobulin K and/or X light chain gene loci, including any of the V and J gene segment coding regions, as well as any of the constant region exons;"

should be replaced with

--(b) the coding regions of the immunoglobulin κ and/or λ light chain gene loci, including any of the V and J gene segment coding regions, as well as any of the constant region exons;--

Signed and Sealed this

Twenty-first Day of September, 2010

David J. Kappos
*Director of the United States Patent and Trademark Office*